(12) United States Patent
Johnson

(10) Patent No.: US 7,842,697 B2
(45) Date of Patent: Nov. 30, 2010

(54) SOLUBLE AMIDE AND ESTER PYRAZINOYLGUANIDINE SODIUM CHANNEL BLOCKERS

(75) Inventor: Michael R. Johnson, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 0 days.

(21) Appl. No.: 12/049,993

(22) Filed: Mar. 17, 2008

(65) Prior Publication Data

US 2009/0076273 A1    Mar. 19, 2009

Related U.S. Application Data

(62) Division of application No. 10/920,391, filed on Aug. 18, 2004, now Pat. No. 7,399,766.

(51) Int. Cl.
A61K 31/4965    (2006.01)
(52) U.S. Cl. ................... 514/255.06; 544/407
(58) Field of Classification Search ............ 514/255.06; 544/407
See application file for complete search history.

(56) References Cited

U.S. PATENT DOCUMENTS

| | | | |
|---|---|---|---|
| 3,527,758 A * | 9/1970 | Jones et al. ............ 544/407 |
| 4,246,406 A * | 1/1981 | Cragoe et al. ............ 544/54 |
| 6,858,614 B2 | 2/2005 | Johnson |
| 6,858,615 B2 | 2/2005 | Johnson |
| 6,903,105 B2 | 6/2005 | Johnson |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,241,766 B2 | 7/2007 | Johnson |
| 7,247,636 B2 | 7/2007 | Johnson |
| 7,247,637 B2 | 7/2007 | Johnson et al. |
| 7,317,013 B2 | 1/2008 | Johnson |
| 7,332,496 B2 | 2/2008 | Johnson |
| 7,345,044 B2 | 3/2008 | Johnson |
| 7,368,447 B2 | 5/2008 | Johnson et al. |
| 7,368,450 B2 | 5/2008 | Johnson |
| 7,368,451 B2 | 5/2008 | Johnson et al. |
| 2005/0080092 A1 | 4/2005 | Johnson |
| 2005/0080093 A1 | 4/2005 | Johnson et al. |
| 2005/0090505 A1 | 4/2005 | Johnson et al. |
| 2005/0228182 A1 | 10/2005 | Johnson et al. |
| 2006/0040954 A1 | 2/2006 | Johnson |
| 2006/0142306 A1 | 6/2006 | Johnson |
| 2006/0142581 A1 | 6/2006 | Johnson |
| 2006/0205738 A1 | 9/2006 | Johnson et al. |
| 2007/0032509 A1 | 2/2007 | Johnson et al. |
| 2007/0265280 A1 | 11/2007 | Johnson |
| 2008/0076782 A1 | 3/2008 | Johnson |
| 2008/0090841 A1 | 4/2008 | Johnson et al. |
| 2008/0096896 A1 | 4/2008 | Johnson |
| 2008/0103148 A1 | 5/2008 | Johnson |

FOREIGN PATENT DOCUMENTS

| | | |
|---|---|---|
| WO | WO 03/070182 | 8/2003 |
| WO | WO 03/070184 | 8/2003 |
| WO | WO 2004/073629 | 9/2004 |
| WO | WO 2005/018644 | 3/2005 |
| WO | WO 2005/044180 | 5/2005 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
U.S. Appl. No. 12/501,654, filed Jul. 13, 2009, Boucher, et al.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.

(Continued)

Primary Examiner—James O Wilson
Assistant Examiner—Douglas M Willis
(74) Attorney, Agent, or Firm—Oblon, Spivak, McClelland, Maier & Neustadt, L.L.P.

(57) ABSTRACT

The present invention relates to pyrazinoylguanidine compounds represented by the formula:

$$\text{X} \underset{\text{Y}}{\overset{\text{N}}{\diagdown}} \underset{\text{N}}{\overset{\text{N}}{\diagup}} \underset{\text{NHR}^2}{\overset{\text{O}}{\diagdown}} \underset{\text{N}=\text{C}-\text{N}}{\overset{\text{NHR}^1}{\diagdown}} \overset{R^3}{\underset{R^4}{\diagdown}} \quad (I)$$

where the structural variables are defined herein. The compounds are useful as sodium channel blockers.

18 Claims, No Drawings

OTHER PUBLICATIONS

U.S. Appl. No. 60/909,818, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al.
U.S. Appl. No. 61/030,313, filed Feb. 21, 2008, Johnson.
U.S. Appl. No. 61/031,466, filed Feb. 26, 2008, Johnson.
U.S. Appl. No. 12/171,814, filed Jul. 11, 2008, Johnson. et al.
U.S. Appl. No. 12/171,867, filed Jul. 11, 2008, Johnson. et al.
U.S. Appl. No. 12/171,897, filed Jul. 11, 2008, Johnson. et al.
U.S. Appl. No. 12/190,022, filed Aug. 12, 2008, Johnson.
U.S. Appl. No. 61/079,989, filed Jul. 11, 2008, Boucher, et al.
U.S. Appl. No. 12/179,353, filed Jul. 24, 2008, Johnson.
U.S. Appl. No. 12/393,252, filed Feb. 26, 2009, Johnson.
U.S. Appl. No. 12/249,175, filed Oct. 10, 2008, Boucher, et al.
U.S. Appl. No. 12/304,006, filed Dec. 9, 2008, Johnson, et al.
U.S. Appl. No. 12/304,042, filed Dec. 9, 2008, Johnson.
U.S. Appl. No. 12/304,040, filed Dec. 9, 2008, Johnson.
U.S. Appl. No. 10/920,527, filed Aug. 18, 2004, Hopkins.
U.S. Appl. No. 11/573,413, filed Feb. 8, 2007, Johnson.
U.S. Appl. No. 11/573,421, filed Feb. 8, 2007, Johnson.
U.S. Appl. No. 11/696,003, filed Apr. 3, 2007, Johnson.
U.S. Appl. No. 11/852,003, filed Sep. 7, 2007, Johnson, et al.
U.S. Appl. No. 11/835,902, filed Aug. 8, 2007, Johnson, et al.
U.S. Appl. No. 12/049,946, filed Mar. 17, 2008, Johnson, et al.
U.S. Appl. No. 12/049,968, filed Mar. 17, 2008, Johnson, et al.
U.S. Appl. No. 12/049,894, filed Mar. 17, 2008, Johnson, et al.
U.S. Appl. No. 12/050,010, filed Mar. 17, 2008, Johnson.
U.S. Appl. No. 12/050,019, filed Mar. 17, 2008, Johnson.
U.S. Appl. No. 12/061,837, filed Apr. 3, 2008, Johnson, et al.
U.S. Appl. No. 12/061,864, filed Apr. 3, 2008, Johnson, et al.
U.S. Appl. No. 12/098,581, filed Apr. 7, 2008, Johnson.

* cited by examiner

SOLUBLE AMIDE AND ESTER PYRAZINOYLGUANIDINE SODIUM CHANNEL BLOCKERS

CROSS-REFERENCE TO RELATED APPLICATIONS

This application is a divisional of U.S. application Ser. No. 10/920,391, filed on Aug. 18, 2004, now U.S. Pat. No. 7,399,766.

BACKGROUND OF THE INVENTION

1. Field of the Invention

The present invention relates to sodium channel blockers. The present invention also includes a variety of methods of treatment using these inventive sodium channel blockers.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diurectics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete Cl— (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

Fifty million Americans and hundreds of millions of others around the world suffer from high blood pressure and the subsequent sequale leading to congestive heart failure and increasing mortality. It is the Western World's leading killer and there is a need there for new medicines to treat these diseases. Thus, in addition, some of the novel sodium channel blockers of this invention can be designed to target the kidney and as such they may be used as diuretics for the treatment of hypertension, congestive heart failure (CHF) and other cardiovascular diseases. These new agents may be used alone or in combination with beta-blockers, ACE inhibitors, HMG-CoA reductase inhibitors, calcium channel blockers and other cardiovascular agents.

SUMMARY OF THE INVENTION

It is an object of the present invention to provide compounds that are more potent and/or absorbed less rapidly from mucosal surfaces, and/or are less reversible as compared to known compounds.

It is another aspect of the present invention to provide compounds of formula (I) that are more potent and/or absorbed less rapidly and/or exhibit less reversibility, as compared to compounds such as amilorde, benzamil, and phenamil. Therefore, the compounds of formula (I) will give a prolonged pharmacodynamic half-life on mucosal surfaces as compared to known compounds.

It is another aspect of the present invention to provide compounds of formula (I) that are more soluble in aqueous solutions, especially in 0.12-0.9% saline, so that they can be conveniently administered to mucosal surfaces of a patient by suitable means such as a nebulizer, spay, mist or droplets. Therefore, the compounds of formula (I) are more soluble in aqueous solutions as compared to known compounds lacking the additional proanatable nitrogen(s) contained in compounds of Formula (I)

It is another object of the present invention to provide compounds of formula (I) which are (1) absorbed less rapidly from mucosal surfaces, especially airway surfaces, as compared to known compounds and; (2) when absorbed from musosal surfaces after administration to the mucosal surfaces, are converted in vivo into metabolic derivitives thereof which have reduced efficacy in blocking sodium channels as compared to the administered parent compound.

It is another object of the present invention to provide compounds of formula (I) that are more potent and/or absorbed less rapidly and/or exhibit less reversibility, as compared to compounds such as amiloride, benzamil, and phenamil. Therefore, the compounds of formula (I) will give a prolonged pharmacodynamic half-life on mucosal surfaces as compared to previous compounds.

It is another object of the present invention to provide compounds of formula (I) that target the kidney for use in the treatment of cardiovascular disease.

It is another object of the present invention to provide methods of treatment which take advantage of the properties described above.

The objects of the present invention may be accomplished with a class of pyrazinoylguanidine compounds represented by formula (I):

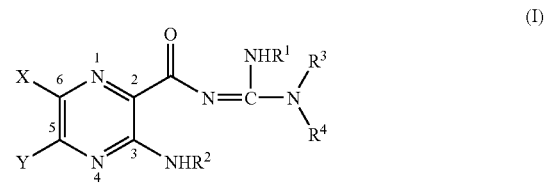

where X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl; Y is hydrogen, hydroxyl, mercapto, lower alkoxy, lower alkyl-thio, halogen, lower alkyl, unsubstituted or substituted mononuclear aryl, or $-N(R^2)_2$; $R^1$ is hydrogen or lower alkyl; each $R^2$ is, independently, $-R^7$, $-(CH_2)_m-OR^8$, $-(CH_2)_m-NR^7R^{10}$, $-(CH_2)_n(CHOR^8)_n(CHOR^8)_n-CH_2OR^8$, $-(CH_2CH_2O)_m-R^8$, $-(CH_2CH_2O)_m-CH_2CH_2NR^7R^{10}$, $-(CH_2)$, $-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

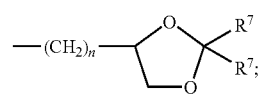

wherein when two $-CH_2OR^8$ groups are located 1,2- or 1,3- with respect to each other the $R^8$ groups may be joined to form a cyclic mono- or di-substituted 1,3-dioxane or 1,3-dioxolane; $R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

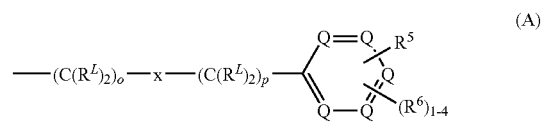

wherein
each $R^L$ is, independently, $-R^7-(CH_2)_n-OR^8$, $-O(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $(CH_2CH_2O)_m-$ CH$_2$CH$_2$NR$^7$R$^{10}$, —O—(CH$_2$CH$_2$O)$_m$—CH$_2$CH$_2$NR$^7$R$^{10}$, —(CH$_2$)$_m$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$-(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$—OSO$_3$H, —O-glucuronide, —O-glucose,

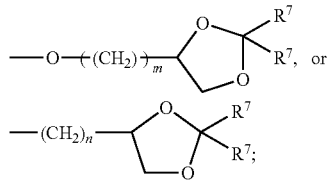

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each o is, independently, an integer from 0 to 10;

each p is an integer from 0 to 10;

with the proviso that the sum of o and p in each contiguous chain is from 1 to 10;

each x is, independently, O, NR$^{10}$, C(=O), CHOH, C(=N—R$^{10}$), CHNR$^7$R$^{10}$, or represents a single bond;

each R$^5$ is independently, —(CH$_2$)$_n$—CO$_2$R$^{13}$, Het-(CH$_2$)$_m$—CO$_2$R$^{13}$, —(CH$_2$)$_n$—Z$_g$—CO$_2$R$^{13}$, Het-(CH$_2$)$_m$—Z$_g$—CO$_2$R$^{13}$, —(CH$_2$)$_n$—NR$^{10}$—(CH$_2$)$_m$(CHOR$^8$)$_n$—CO$_2$R$^{13}$, Het-(CH$_2$)$_m$—NR$^{10}$—(CH$_2$)$_m$(CHOR$^8$)$_n$—CO$_2$R$^{13}$, —(CH$_2$)$_n$—(CHOR$^8$)$_m$—CO$_2$R$^{13}$, Het-(CH$_2$)$_m$—(CHOR$^8$)$_m$—CO$_2$R$^{13}$, —(CH$_2$)$_n$—(CHOR$^8$)$_m$Z$_g$—CO$_2$R$^{13}$, Het-(CH$_2$)$_n$—(CHOR$^8$)$_m$—Z$_g$—CO$_2$R$^{13}$, —(CH$_2$)$_n$—Z$_g$—(CH$_2$)$_m$—CO$_2$R$^{13}$, —(CH$_2$)$_n$—Z$_g$—(CH$_2$)$_m$—CO$_2$R$^{13}$, —(CH$_2$)$_n$—Z$_g$(CHOR$^8$)$_m$—Z$_g$—CO$_2$R$^{13}$, Het-(CH$_2$)$_n$—Z$_g$—(CHOR$^8$)$_m$—Z$_g$—CO$_2$R$^{13}$, —(CH$_2$)$_n$—CONH—C(=NR$^{13}$)—NR$^{13}$R$^{13}$, Het-(CH$_2$)$_n$—CO—NH—C(=NR$^{13}$)—NR$^{13}$R$^{13}$, (CH$_2$)$_n$—Z$_g$—CONH—C(=NR$^{13}$)—NR$^{13}$R$^{13}$, Het-(CH$_2$)$_n$—Z$_g$—CONH—C(=NR$^{13}$)—NR$^{13}$R$^{13}$, —(CH$_2$)$_n$—NR$^{10}$—(CH$_2$)$_m$(CHOR$^8$)$_n$—CONH—C(=NR$^{13}$)—NR$^{13}$R$^{13}$, Het-(CH$_2$)$_n$—NR$^{10}$—(CH$_2$)$_m$(CHOR$^8$)$_n$—CONH—C(=NR$^{13}$)—NR$^{13}$R$^{13}$, —(CH$_2$)$_n$—(CHOR$^8$)$_m$—CONH—C(=NR$^{13}$)—NR$^{13}$R$^{13}$, Het-(CH$_2$)$_n$—(CHOR$^8$)$_m$—CONH—C(=NR$^{13}$)—NR$^{13}$R$^{13}$, —(CH$_2$)$_n$—(CHOR$^8$)$_m$—Z$_g$—CONH—C(=NR$^{13}$)—NR$^{13}$R$^{13}$, Het-(CH$_2$)$_n$—(CHOR$^8$)$_m$—Z$_g$—CONH—C(=NR$^{13}$)—NR$^{13}$R$^{13}$, —(CH$_2$)$_n$—Z$_g$—(CH$_2$)$_m$CONH—C(=NR$^{13}$)—NR$^{13}$R$^{13}$, Het-(CH$_2$)$_n$—Z$_g$—(CH$_2$)$_m$CONH—C(=NR$^{13}$)—NR$^{13}$R$^{13}$, —(CH$_2$)$_m$—Z$_g$—(CHOR$^8$)$_m$—Z$_g$—CONH—C(=NR$^{13}$)—NR$^{13}$R$^{13}$, Het-(CH$_2$)$_n$—Z$_g$—(CHOR$^8$)$_m$—Z$_g$—CONH—C(=NR$^{13}$)—NR$^{13}$R$^{13}$, —(CH$_2$)$_n$—CONR$^7$—CONR$^{13}$R$^{13}$, Het-(CH$_2$)$_n$—CONR$^7$—CONR$^{13}$R$^{13}$, (CH$_2$)$_n$Z$_g$—CONR$^7$—CONR$^{13}$R$^{13}$, —(CH$_2$)$_n$—Z$_g$—CONR$^7$—CONR$^{13}$R$^{13}$, —(CH$_2$)$_n$—NR$^{10}$—(CH$_2$)$_m$(CHOR$^8$)$_n$—CONR$^7$—CONR$^{13}$R$^{13}$, Het-(CH$_2$)$_n$—NR$^{10}$—(CH$_2$)$_m$(CHOR$^8$)$_n$—CONR$^7$—CONR$^{13}$R$^{13}$, —(CH$_2$)$_n$—(CHOR$^8$)$_m$—CONR$^7$—CONR$^{13}$R$^{13}$, Het-(CH$_2$)$_n$—(CHOR$^8$)$_m$—CONR$^7$—CONR$^{13}$R$^{13}$, —(CH$_2$)$_n$—(CHOR$^8$)$_m$—Z$_g$—CONR$^7$—CONR$^{13}$R$^{13}$, Het-(CH$_2$)$_n$—(CHOR$^8$)$_m$—Z$_g$—CONR$^7$—CONR$^{13}$R$^{13}$, Z$_g$—CNR$^7$—CONR$^{13}$R$^{13}$, —(CH$_2$)$_n$—Z$_g$—(CH$_2$)$_m$CONR$^7$—CONR$^{13}$R$^{13}$, Het-(CH$_2$)$_n$—Z$_g$—(CH$_2$)$_m$CONR$^7$—CONR$^{13}$R$^{13}$, —(CH$_2$)$_n$—Z$_g$(CHOR$^8$)$_m$—Z$_g$—CONR$^7$—CONR$^{13}$R$^{13}$, Het-(CH$_2$)$_n$—Z$_g$(CHOR$^8$)$_m$—Z$_g$—CONR$^7$—CONR$^{13}$R$^{13}$, —(CH$_2$)$_n$—CONR$^7$SO$_2$NR$^{13}$R$^{13}$, Het-(CH$_2$)$_m$—CONR$^7$SO$_2$NR$^{13}$R$^{13}$, —(CH$_2$)$_n$—Z$_g$—CONR$^7$SO$_2$NR$^{13}$R$^{13}$, Het-(CH$_2$)$_m$—Z$_g$—CONR$^7$SO$_2$NR$^{13}$R$^{13}$, —(CH$_2$)$_n$—NR$^{10}$—(CH$_2$)$_m$(CHOR$^8$)$_n$—CONR$^7$SO$_2$NR$^{13}$R$^{13}$, Het-(CH$_2$)$_m$—NR$^{10}$—(CH$_2$)$_m$(CHOR$^8$)$_n$—CONR$^7$SO$_2$NR$^{13}$R$^{13}$, —(CH$_2$)$_n$—(CHOR$^8$)$_m$—CONR$^7$SO$_2$NR$^{13}$R$^{13}$, Het-(CH$_2$)$_m$—(CHOR$^8$)$_m$—CONR$^7$SO$_2$NR$^{13}$R$^{13}$, —(CH$_2$)$_n$—(CHOR$^8$)$_m$—Z$_g$—CONR$^7$SO$_2$NR$^{13}$R$^{13}$, Het-(CH$_2$)$_n$—(CHOR$^8$)$_m$—Z$_g$—CONR$^7$SO$_2$NR$^{13}$R$^{13}$, —(CH$_2$)$_n$—Z$_g$—(CH$_2$)$_m$CONR$^7$SO$_2$NR$^{13}$R$^{13}$, Het-(CH$_2$)$_n$—Z$_g$—(CH$_2$)$_m$CONR$^7$SO$_2$NR$^{13}$R$^{13}$, —(CH$_2$)$_n$—Z$_g$—(CHOR$^8$)$_m$—Z$_g$—CONR$^7$SO$_2$NR$^{13}$R$^{13}$, Het-(CH$_2$)$_n$—Z$_g$—(CHOR$^8$)$_m$—Z$_g$—CONR$^7$SO$_2$NR$^{13}$R$^{13}$, —(CH$_2$)$_n$—SO$_2$NR$^{13}$R$^{13}$, Het-(CH$_2$)$_m$—SO$_2$NR$^{13}$R$^{13}$, (CH$_2$)$_n$—Z$_g$—SO$_2$NR$^{13}$R$^{13}$, Het-(CH$_2$)$_m$—Z$_g$—SO$_2$NR$^{13}$R$^{13}$, —(CH$_2$)$_n$—NR$^{10}$—(CH$_2$)$_m$(CHOR$^8$)$_n$—SO$_2$NR$^{13}$R$^{13}$, Het-(CH$_2$)$_m$—NR$^{10}$—(CH$_2$)$_m$(CHOR$^8$)$_n$—SO$_2$NR$^{13}$R$^{13}$, —(CH$_2$)$_n$—(CHOR$^8$)$_m$—SO$_2$NR$^{13}$R$^{13}$, Het-(CH$_2$)$_m$—(CHOR$^8$)$_m$—SO$_2$NR$^{13}$R$^{13}$, —(CH$_2$)$_n$—(CHOR$^8$)$_m$—Z$_g$—SO$_2$NR$^{13}$R$^{13}$, Het-(CH$_2$)$_n$—(CHOR$^8$)$_m$—Z$_g$—SO$_2$NR$^{13}$R$^{13}$, —(CH$_2$)$_n$—Z$_g$—(CH$_2$)$_m$SO$_2$NR$^{13}$R$^{13}$, Het-(CH$_2$)$_n$—Z$_g$—(CH$_2$)$_m$SO$_2$NR$^{13}$R$^{13}$, —(CH$_2$)$_n$—Z$_g$—(CHOR$^8$)$_m$—Z$_g$—SO$_2$NR$^{13}$R$^{13}$, Het-(CH$_2$)$_n$—Z$_g$—(CHOR$^8$)$_m$—Z$_g$—SO$_2$NR$^{13}$R$^{13}$, —(CH$_2$)$_n$—CONR$^{13}$R$^{13}$, Het-(CH$_2$)$_m$—CONR$^{13}$R$^{13}$, (CH$_2$)$_n$—Z$_g$—CONR$^{13}$R$^{13}$, Het-(CH$_2$)$_m$—Z$_g$—CONR$^{13}$R$^{13}$, —(CH$_2$)$_n$—NR$^{10}$—(CH$_2$)$_m$(CHOR$^8$)$_n$—CONR$^{13}$R$^{13}$, Het-(CH$_2$)$_m$—NR$^{10}$—(CH$_2$)$_m$(CHOR$^8$)$_n$—CONR$^{13}$R$^{13}$, —(CH$_2$)$_n$—(CHOR$^8$)$_m$—CONR$^{13}$R$^{13}$, Het-(CH$_2$)$_m$—(CHOR$^8$)$_m$—CONR$^{13}$R$^{13}$, —(CH$_2$)$_n$—(CHOR$^8$)$_m$—Z$_g$—CONR$^{13}$R$^{13}$, Het-(CH$_2$)$_n$—(CHOR$^8$)$_m$—Z$_g$—CONR$^{13}$R$^{13}$, —(CH$_2$)$_n$—Z$_g$—(CH$_2$)$_m$CONR$^{13}$R$^{13}$, Het-(CH$_2$)$_n$—Z$_g$—(CH$_2$)$_m$CONR$^{13}$R$^{13}$, —(CH$_2$)$_n$—Z$_g$—(CHOR$^8$)$_m$—Z$_g$—CONR$^{13}$R$^{13}$, Het-(CH$_2$)$_n$—Z$_g$—(CHOR$^8$)$_m$—Z$_g$—CONR$^{13}$R$^{13}$, —(CH$_2$)$_n$—CONR$^7$COR$^{13}$, Het-(CH$_2$)$_m$—CONR$^7$COR$^{13}$, —(CH$_2$)$_n$—Z$_g$—CONR$^7$COR$^{13}$, Het-Het-(CH$_2$)$_m$—(CHOR$^8$)$_m$—CONR$^7$COR$^{13}$, —(CH$_2$)$_n$—(CHOR$^8$)$_m$—Z$_g$—CONR$^7$COR$^{13}$, Het-(CH$_2$)$_n$—(CHOR$^8$)$_m$—Z$_g$—CONR$^7$COR$^{13}$, —(CH$_2$)$_n$—Z$_g$—(CH$_2$)$_m$CONR$^7$COR$^{13}$, —(CH$_2$)$_n$—Z$_g$—(CH$_2$)$_m$CONR$^7$COR$^{13}$, Het-(CH$_2$)$_n$—Z$_g$—(CHOR$^8$)$_m$—Z$_g$—CONR$^7$COR$^{13}$, —(CH$_2$)$_n$—CONR$^7$CO$_2$R$^{13}$, —(CH$_2$)$_n$—Z$_g$—CONR$^7$CO$_2$R$^{13}$, Het-(CH$_2$)$_m$—Z$_g$—CONR$^7$CO$_2$R$^{13}$, —(CH$_2$)$_n$—NR$^{10}$—(CH$_2$)$_m$(CHOR$^8$)$_n$—CONR$^7$CO$_2$R$^{13}$, Het-(CH$_2$)$_m$—NR$^{10}$—(CH$_2$)$_m$(CHOR$^8$)$_n$—CONR$^7$CO$_2$R$^{13}$, —(CH$_2$)$_n$—(CHOR$^8$)$_m$—CONR$^7$CO$_2$R$^{13}$, Het-(CH$_2$)$_m$—(CHOR$^8$)$_m$—CONR$^7$CO$_2$R$^{13}$, (CH$_2$)$_n$—Z$_g$—(CH$_2$)$_n$CONR$^7$CO$_2$R$^{13}$, Het-(CH$_2$)$_n$—Z$_g$—(CH$_2$)$_m$CONR$^7$CO$_2$R$^{13}$, —(CH$_2$)$_n$—Z$_g$—(CHOR$^8$)$_m$—Z$_g$—CONR$^7$CO$_2$R$^{13}$, Het-(CH$_2$)$_n$—Z$_g$—(CHOR$^8$)$_m$—Z$_g$—CONR$^7$CO$_2$R$^{13}$, —(CH$_2$)$_n$—NH—C(=NR$^{13}$)—NR$^{13}$R$^{13}$, Het-(CH$_2$)$_m$—NH—C(=NR$^{13}$)—NR$^{13}$R$^{13}$, —(CH$_2$)$_n$—Z$_g$—NH—C(=NR$^{13}$)—NR$^{13}$R$^{13}$, Het-(CH$_2$)$_m$—Z$_g$—NH—C $(=NR^{13})-NR^{13}R^{13}$, $-(CH_2)_n-NR^{10}-(CH_2)_m(CHOR^8)_n-NH-C(=NR^{13})-NR^{13}R^{13}$, Het-$(CH_2)_m-NR^{10}-(CH_2)_m(CHOR^8)_n-NH-C(=NR^{13})-NR^{13}R^{13}$, $-(CH_2)_n-(CHOR^8)_m-NH-C(=NR^{13})-NR^{13}R^{13}$, Het-$(CH_2)_m-(CHOR^8)_m-NH-C(=NR^{13})-NR^{13}R^{13}$, $-(CH_2)_n-(CHOR^8)_m-Z_g-NH-C(=NR^{13})-NR^{13}R^{13}$, Het-$(CH_2)_n-(CHOR^8)_m-Z_g-NH-C(=NR^{13})-NR^{13}R^{13}$, $-(CH_2)_n-Z_g-(CH_2)_mNH-C(=NR^{13})-NR^{13}R^{13}$, Het-$(CH_2)_n-Z_g-(CH_2)_mNH-C(=NR^{13})-NR^{13}R^{13}$, $-(CH_2)_n-Z_g-(CHOR^8)_m-Z_g-NH-C(=NR^{13})-NR^{13}R^{13}$, Het-$(CH_2)_n-Z_g-(CHOR^8)_m-Z_g-NH-C(=NR^{13})-NR^{13}R^{13}$, $-(CH_2)_n-C(=NR^{13})-NR^{13}R^{13}$, Het-$(CH_2)_m-C(=NH)-NR^{13}R^{13}$, $-(CH_2)_n-Z_g-C(=NH)-NR^{13}R^{13}$, Het-$(CH_2)_m-Z_g-C(=NH)-NR^{13}R^{13}$, $(CH_2)_n-NR^{10}-(CH_2)_m(CHOR^8)_n-C(=NR^{13})-NR^{13}R^{13}$, Het-$(CH_2)_m-NR^{10}-(CH_2)_m(CHOR^8)_n-C(=NR^{13})-NR^{13}R^{13}$, $-(CH_2)_n-(CHOR^8)_m-C(=NR^{13})-NR^{13}R^{13}$, Het-$(CH_2)_m-(CHOR^8)_m-C(=NR^{13})-NR^{13}R^{13}$, $-(CH_2)_n-(CHOR^8)_m-Z_g-C(=NR^{13})-NR^{13}R^{13}$, Het-$(CH_2)_n-(CHOR^8)_m-Z_g-C(=NR^{13})-NR^{13}R^{13}$, $-(CH_2)_n-Z_g-(CH_2)_m-C(=NHC(=NR^{13})-NR^{13}R^{13}$, Het-$(CH_2)_n-Z_g-(CH_2)_m-C(=NR^{13})-NR^{13}R^{13}$, $-(CH_2)_n-Z_g-(CHOR^8)_m-Z_g-C(=NR^{13})-NR^{13}R^{13}$, Het-$(CH_2)_n-Z_g-(CHOR^8)_m-Z_g-C(=NR^{13})-NR^{13}R^{13}$;

wherein when two —$CH_2OR^8$ groups are located 1,2- or 1,3- with respect to each other the $R^8$ groups may be joined to form a cyclic mono- or di-substituted 1,3-dioxane or 1,3-dioxolane;

each $R^6$ is, independently, —$R^5$, —$R^7$, —$OR^8$, —$N(R^7)_2$, —$(CH_2)_m-OR^8$, —$O-(CH_2)_m-OR^8$, —$(CH_2)_n-NR^7R^{10}$, —$O-(CH_2)_m-NR^7R^{10}$, —$(CH_2)_n(CHOR^8)(CHOR^8)_n-CH_2OR^8$, —$O-(CH_2)_m(CHOR^8)(CHOR^8)_n-CH_2OR^8$, —$(CH_2CH_2O)_m-R^8$, —$O-(CH_2CH_2O)_m-R^8$, $(CH_2CH_2O)_m-CH_2CH_2NR^7R^{10}$, —$O-(CH_2CH_2O)_m-CH_2CH_2NR^7R^{10}$, —$(CH_2)_n-C(=O)NR^7R^{10}$, —$O-(CH_2)_m-C(=O)NR^7R^{10}$, —$(CH_2)_n-(Z)_g-R^7$, —$O-(CH_2)_m-(Z)_g-R^7$, —$(CH_2)_n-NR^{10}-CH_2(CHOR^8)(CHOR^8)_n-CH_2OR^8$, —$O-(CH_2)_m-NR^{10}-CH_2(CHOR^8)(CHOR^8)_n-CH_2OR^8$, —$(CH_2)_n-CO_2R^7$, —$O(CH_2)_m-CO_2R^7-OSO_3H$, —O-glucuronide, —O-glucose,

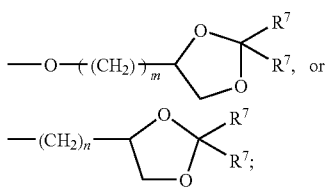

wherein when two $R^6$ are —$OR^{11}$ and are located adjacent to each other on a phenyl ring, the alkyl moieties of the two $R^6$ may be bonded together to form a methylenedioxy group, and wherein when two —$CH_2OR^8$ groups are located 1,2- or 1,3- with respect to each other the $R^8$ groups may be joined to form a cyclic mono- or di-substituted 1,3-dioxane or 1,3-dioxolane;

each $R^7$ is, independently, hydrogen lower alkyl, phenyl, substituted phenyl or —$CH_2(CHOR)^8_m-R^{10}$;

each $R^8$ is, independently, hydrogen, lower alkyl, —$C(=O)-R^{11}$, glucuronide, 2-tetrahydropyranyl, or

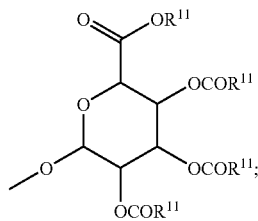

each $R^9$ is, independently, —$CO_2R^7$, —$CON(R^7)_2$, —$SO_2CH_3$, or —$C(=O)R^7$;

each $R^{10}$ is, independently, —H, —$SO_2CH_3$, —$CO_2R^7$, —$C(=O)NR^7R^9$, —$C(=O)R^7$, or —$(CH_2)_m-(CHOH)_n-CH_2OH$;

each Z is, independently, CHOH, C(=O), —$(CH_2)_n-$, $CHNR^7R^{10}$, C=$NR^{10}$, or $NR^{10}$;

each $R^{11}$ is, independently, lower alkyl;

each $R^{12}$ is independently, —$SO_2CH_3$, —$CO_2R^7$, —$C(=O)NR^7R^9$, —$C(=O)R^7$, or —$CH_2-(CHOH)_n-CH_2OH$;

each $R^{13}$ is, independently, hydrogen, $R^7$, $R^{10}$, —$(CH_2)_m-NR^7R^{10}$, —$(CH_2)_m-NR^7R^7$, —$(CH_2)_m$ —$(CH_2)_m-\overset{+}{N}R^{11}R^{11}R^{11}$, —$(CH_2)_m-(CHOR^8)_m-(CH_2)_mNR^7R^{10}$, —$(CH_2)_m-NR^{10}R^{10}$, —$(CH_2)_m-(CHOR^8)_m-(CH_2)_mNR^7R^7$, —$(CH_2)_m-(CHOR^8)_m-(CH_2)_m\overset{+}{N}R^{11}R^{11}R^{11}$,

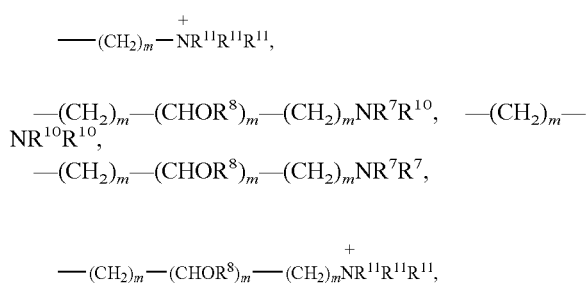

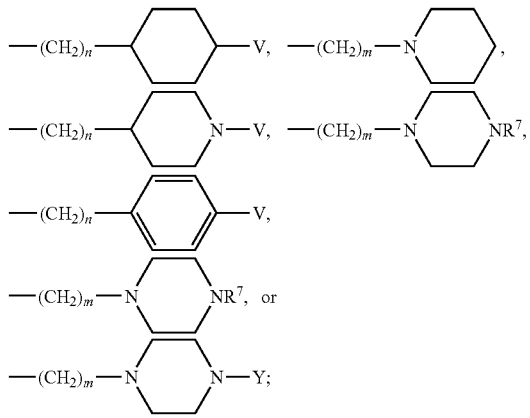

with the proviso that at least one $R^{13}$ must be a group other than hydrogen, $R^7$, or $R^{10}$;

with the further proviso that $NR^{13}R^{13}$ can be joined on itself to form a ring comprising one of the following:

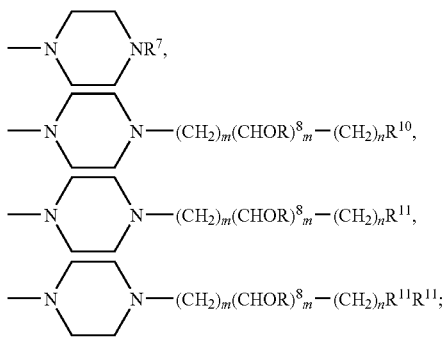

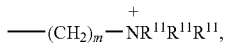

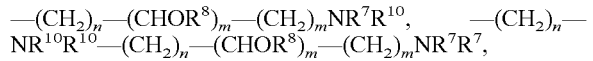

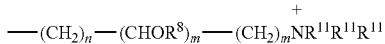

each Het is independently, —NR$^7$, —NR$^{10}$, —S—, —SO—, or —SO$_2$—; —O—, —SO$_2$NH—, —NHSO$_2$—, —NR$^7$CO—, or —CONR$^7$—;

each g is, independently, an integer from 1 to 6;
each m is, independently, an integer from 1 to 7;
each n is, independently, an integer from 0 to 7;
each Q is, independently, C—R$^5$, C—R$^6$, or a nitrogen atom, wherein at most three Q in a ring are nitrogen atoms;
each V is, independently, —(CH$_2$), —NR$^7$R$^{10}$, —(CH$_2$)$_m$—NR$^7$R$^7$, —(CH$_2$)$_m$—$\overset{+}{N}$R$^{11}$R$^{11}$R$^{11}$, —(CH$_2$)$_n$—(CHOR$^8$)$_m$—(CH$_2$)$_m$NR$^7$R$^{10}$, —(CH$_2$)$_n$—NR$^{10}$R$^{10}$—(CH$_2$)$_n$—(CHOR$^8$)$_m$—(CH$_2$)$_m$NR$^7$R$^7$, —(CH$_2$)$_n$—(CHOR$^8$)$_m$—$\overset{+}{N}$(CH$_2$)$_m$NR$^{11}$R$^{11}$R$^{11}$ with the proviso that when V is attached directly to a nitrogen atom, then V can also be, independently, R$^7$, R$^{10}$, or (R$^{11}$)$_2$;
wherein for any of the above compounds when two —CH$_2$OR$^8$ groups are located 1,2- or 1,3- with respect to each other the R$^8$ groups may be joined to form a cyclic mono- or di-substituted 1,3-dioxane or 1,3-dioxolane;
wherein any of the above compounds can be a pharmaceutically acceptable salt thereof, and wherein the above compounds are inclusive of all enantiomers, diastereomers, and racemic mixtures thereof.

In a preferred embodiment, each —(CH$_2$)$_n$—Z$_g$—C(=NH)—NR$^{13}$R$^{13}$ falls within the scope of the structures described above and is, independently, —(CH$_2$)$_n$—CHNH$_2$(C=N)—NR$^{13}$R$^{13}$.

In another preferred embodiment, each Het-(CH$_2$)$_m$—NH—C(=NH)—NR$^{13}$R$^{13}$ falls within the scope of the structures described above and is, independently, —(CH$_2$)$_n$—NH—C(=NH)NHR$^{13}$.

In another preferred embodiment, each —(CH$_2$)$_n$—Z$_g$—(CHOR$^8$)$_m$—Z$_g$—CONR$^{13}$R$^{13}$ falls within the scope of the structures described above and is, independently, (CH$_2$)$_n$—CONHCH$_2$(CHOH)$_m$—CONHR$^{13}$.

In another preferred embodiment, each Het-(CH$_2$)$_n$—Z$_g$—(CHOR$^8$)$_m$—Z$_g$—CONR$^{13}$R$^{13}$ falls within the scope of the structures described above and is, independently, —NH—C(=O)—CH$_2$—(CHOH)$_n$CH$_2$CONR$^{13}$R$^{13}$.

In another a preferred embodiment, each Het-(CH$_2$)$_m$—Z$_g$—C(=NH)—NR$^{13}$R$^{13}$ falls within the scope of the structures described above and is, independently, —O—(CH$_2$)$_m$—NH—C(=NH)—N(R$^{13}$)$_2$.

In another a preferred embodiment, each Het-(CH$_2$)$_m$—Z$_g$—CONR$^{13}$R$^{13}$ falls within the scope of the structures described above and is, independently, —O—(CH$_2$)$_m$—CHNH$_2$—CO$_2$NR$^{13}$R$^{13}$.

In another preferred embodiment, each R$^5$ falls within the scope of the structures described above and is, independently:
—O—CH$_2$CHOHCH$_2$CONR$^{13}$R$^{13}$
—OCH2CHOHCH2CO2R$^{13}$OCH$_2$CH$_2$CONR$^{13}$R$^{13}$
—OCH$_2$CH$_2$NHCOR$^{13}$
—CH$_2$CH$_2$CONR$^{13}$R$^{13}$
—OCH$_2$CH$_2$CONR$^{13}$R$^{13}$O—(CH$_2$)$_m$—CO$_2$R$^{13}$
—(CH$_2$)$_m$—CO$_2$R$^{13}$
—OCH$_2$CH$_2$CO$_2$R$^{13}$
—OCH$_2$CO$_2$R$^{13}$
—O—(CH$_2$)$_m$—NH—C(=NH)—NR$^{13}$)$_2$
—(CH$_2$)$_n$—NH—C(=NH)—N(R$^{13}$)$_2$
—NHCH$_2$(CHOH)$_2$—CONR$^{13}$R$^{13}$
—OCH$_2$CO$_2$R$^{13}$
—NHSO$_2$(CH$_2$)$_2$CONR$^{13}$R$^{13}$
—(CH$_2$)$_m$—NH—C(=O)—OR$^{13}$
—O—(CH$_2$)$_n$—NH—C(=O)—OR$^{13}$
—(CH$_2$)$_n$—NH—C(=O)—R$^{13}$
—O—(CH$_2$)$_m$—NH—C(=O)—R$^{13}$
—O—CH$_2$C(=ONR$^{13}$R$^{13}$
—CH$_2$NCO$_2$R$^{13}$—NHCO$_2$R$^{13}$
—OCH$_2$CH$_2$CH$_2$CH$_2$CONR$^{13}$R$^{13}$
—SO$_2$CH$_2$CH$_2$CONR$^{13}$R$^{13}$
—OCH$_2$CH$_2$CHOHCH$_2$CONR$^{13}$R$^{13}$
—OCH$_2$CH$_2$NHCO$_2$R$^{13}$
—NH—C(=NH2)—NR$^{13}$R$^{13}$
—OCH$_2$-(α-CHOH)$_2$—CONR$^{13}$R$^{13}$
—OCH$_2$CHOHCH$_2$CONHR$^{13}$
—(CH$_2$)$_m$—CHOH—CH$_2$—NHCO$_2$R$^{13}$
—O—(CH$_2$)$_m$—CHOH—CH$_2$—CO$_2$R$^{13}$
—(CH$_2$)$_m$—NHC(O)OR$^{13}$
—O—(CH$_2$)$_m$—NHC(O)OR$^{13}$
—OCH$_2$CH$_2$CH$_2$CONHR$^{13}$
—OCH$_2$CH$_2$NHCH$_2$(CHOH)$_2$CH$_2$CONHR$^{13}$
—OCH$_2$CH$_2$CONH(CH$_2$[(CHOH)$_2$CH$_2$NH$_2$)]$_2$
—(CH$_2$)$_4$—NHCO$_2$R$^{13}$
—(CH$_2$)$_4$—CONR$^{13}$R$^{13}$
—(CH$_2$)$_4$—CO$_2$R$^{13}$
—OCH$_2$CH$_2$CONHSOCH$_2$CH$_2$N(CH$_3$)$_2$
—O—(CH$_2$)$_m$—C(=NH)—N(R$^{13}$)$_2$
—(CH$_2$)$_n$—C(=NH)—N(R$^{13}$)$_2$
—(CH$_2$)$_3$—NHCO$_2$R$^{13}$—(CH$_2$)$_3$CONHCO$_2$R$^{13}$
—O—(CH$_2$)$_m$—NH—NH—C(=NH)—N(R$^{13}$)$_2$
—(CH$_2$)$_n$—NH—NH—C(=NH)—N(R$^{13}$)$_2$ or
—O—CH$_2$—CHOH—CH$_2$—NH—C(=NH)—N(R$^{13}$)$_2$.

The present invention also provides pharmaceutical compositions which contain a compound described above.

The present invention also provides a method of promoting hydration of mucosal surfaces, comprising:
administering an effective amount of a compound represented by formula (I) to a mucosal surface of a subject.

The present invention also provides a method of restoring mucosal defense, comprising:
topically administering an effective amount of compound represented by formula (I) to a mucosal surface of a subject in need thereof.

The present invention also provides a method of blocking ENaC, comprising:
contacting sodium channels with an effective amount of a compound represented by formula (I).

The present invention also provides a method of promoting mucus clearance in mucosal surfaces, comprising:
administering an effective amount of a compound represented by formula (I) to a mucosal surface of a subject.

The present invention also provides a method of treating chronic bronchitis, comprising:
administering an effective amount of a compound represented by formula (I) to a subject in need thereof.

The present invention also provides a method of treating cystic fibrosis, comprising:
administering an effective amount of compound represented by formula (I) to a subject in need thereof.

The present invention also provides a method of treating rhinosinusitis, comprising:
administering an effective amount of a compound represented by a formula (I) to a subject in need thereof.

The present invention also provides a method of treating nasal dehydration, comprising:
administering an effective amount of a compound represented by formula (I) to the nasal passages of a subject in need thereof.

In a specific embodiment, the nasal dehydration is brought on by administering dry oxygen to the subject.

The present invention also provides a method of treating sinusitis, comprising:
administering an effective amount of a compound represented by formula (I) to a subject in need thereof.

The present invention also provides a method of treating pneumonia, comprising:
administering an effective amount of a compound represented by formula (I) to a subject in need thereof.

The present invention also provides a method of preventing ventilator-induced pneumonia, comprising:
administering an effective compound represented by formula (I) to a subject by means of a ventilator.

The present invention also provides a method of treating asthma, comprising:
administering an effective amount of a compound represented by formula (I) to a subject in need thereof.

The present invention also provides a method of treating primary ciliary dyskinesia, comprising:
administering an effective amount of a compound represented by formula (I) to a subject in need thereof.

The present invention also provides a method of treating otitis media, comprising:
administering an effective amount of a compound represented by formula (I) to a subject in need thereof.

The present invention also provides a method of inducing sputum for diagnostic purposes, comprising: administering an effective amount of compound represented by formula (I) to a subject in need thereof.

The present invention also provides a method of treating chronic obstructive pulmonary disease, comprising:
administering an effective amount of a compound represented by formula (I) to a subject in need thereof.

The present invention also provides a method of treating emphysema, comprising:
administering an effective amount of a compound represented by formula (I) to a subject in need thereof.

The present invention also provides a method of treating dry eye, comprising:
administering an effective amount of a compound represented by formula (I) to the eye of the subject in need thereof.

The present invention also provides a method of promoting ocular hydration, comprising:
administering an effective amount of a compound represented by formula (I) to the eye of the subject.

The present invention also provides a method of promoting corneal hydration, comprising:
administering an effective amount of a compound represented by formula (I) to the eye of the subject.

The present invention also provides a method of treating Sjögren's disease, comprising:
administering an effective amount of compound represented by formula (I) to a subject in need thereof.

The present invention also provides a method of treating vaginal dryness, comprising:
administering an effective amount of a compound represented by formula (I) to the vaginal tract of a subject in need thereof.

The present invention also provides a method of treating dry skin, comprising:
administering an effective amount of a compound represented by formula (I) to the skin of a subject in need thereof.

The present invention also provides a method of treating dry mouth (xerostomia), comprising:
administering an effective amount of compound represented by formula (I) to the mouth of the subject in need thereof.

The present invention also provides a method of treating distal intestinal obstruction syndrome, comprising:
administering an effective amount of compound represented by formula (I) to a subject in need thereof.

The present invention also provides a method of treating esophagitis, comprising:
administering an effective amount of a compound represented by formula (I) to a subject in need thereof.

The present invention also provides a method of treating constipation, comprising:
administering an effective amount of a compound represented by formula (I) to a subject in need thereof. In one embodiment of this method, the compound is administered either orally or via a suppository or enema.

The present invention also provides a method of treating chronic diverticulitis comprising:
administering an effective amount of a compound represented by formula (I) to a subject in need thereof.

The present invention also provides a method of treating hypertension, comprising administering the compound represented by formula (I) to a subject in need thereof.

The present invention also provides a method of reducing blood pressure, comprising administering the compound represented by formula (I) to a subject in need thereof.

The present invention also provides a method of treating edema, comprising administering the compound represented by formula (I) to a subject in need thereof.

The present invention also provides a method of promoting diuresis, comprising administering the compound represented by formula (I) to a subject in need thereof.

The present invention also provides a method of promoting natriuresis, comprising administering the compound represented by formula (I) to a subject in need thereof.

The present invention also provides a method of promoting saluresis, comprising administering the compound represented by formula (I) to a subject in need thereof.

DETAILED DESCRIPTION OF THE INVENTION

The present invention is based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels as compared to the parent administered compound, after they are absorbed from mucosal surfaces after administration. This important property means that the compounds will have a lower tendency to cause undesired side-effects by blocking sodium channels located at untargeted locations in the body of the recipient, e.g., in the kidneys.

The present invention is also based on the discovery that certain compounds embraced by formula (I) are more soluble in aqueous solutions, especially in 0.12-0.9% saline, so that they can be conveniently administered to mucosal surfaces of a patient by suitable means such as a nebulizer, spay, mist or droplets. Therefore, the compounds of formula (I) are more soluble in aqueous solutions as compared to known compounds lacking an additional proatonateable nitrogen. The solubility of the compounds in the saline solutions described above may be 0.1 to 7% by weight. The preferred range is 0.1 to 0.9% by weight.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or —$N(R^2)_2$. The alkyl moiety of the lower alkoxy groups is the same as described above. Examples of mononuclear aryl include phenyl groups. The phenyl group may be unsubstituted or substituted as described above. The preferred identity of Y is —$N(R^2)_2$. Particularly preferred are such compounds where each $R^2$ is hydrogen.

$R^1$ may be hydrogen or lower alkyl. Hydrogen is preferred for $R^1$.

Each $R^2$ may be, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—$C(=O)NR^7R^{10}$, —$(CH_2)_n$—$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

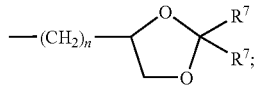

Hydrogen and lower alkyl, particularly $C_1$-$C_3$ alkyl are preferred for $R^2$. Hydrogen is particularly preferred.

$R^3$ and $R^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^3$ and $R^4$ is a group represented by formula (A).

Preferred compounds are those where one of $R^3$ and $R^4$ is hydrogen and the other is represented by formula (A).

In formula (A), the moiety —$(C(R^L)_2)_o$-x-$(C(R^L)_2)_p$— defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, C(=O), CHOH, C(=N—$R^{10}$), $CHNR^7R^{10}$, or represents a single bond;

Therefore, when x represents a single bond, the alkylene chain bonded to the ring is represented by the formula —$(C(R^L)_2)_{o+p}$—, in which the sum o+p is from 1 to 10.

Each $R^L$ may be, independently, —$R^7$, —$(CH_2)_n$—$OR^8$, —O—$(CH_2)_m$—$OR^8$, —$(CH_2)_n$—$NR^7R^{10}$, —O—$(CH_2)$, —$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

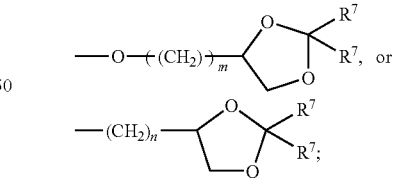

The preferred $R^L$ groups include —H, —OH, —$N(R^7)_2$, especially where each $R^7$ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula —$CHR^L$—. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula $$-(CH_2)_o-x-(CH_2)_p-.$$

There is one $R^5$ present on the ring in formula (A). Each $R^5$ may be, independently, $-(CH_2)_n-CO_2R^{13}$, Het-$(CH_2)_m-CO_2R^{13}$, $-(CH_2)_n-Z_g-CO_2R^{13}$, Het-$(CH_2)_m-Z_g-CO_2R^{13}$, $-(CH_2)_n-NR^{10}-(CH_2)_m(CHOR^8)_n-CO_2R^{13}$, Het-$(CH_2)_m-NR^{10}-(CH_2)_m(CHOR^8)_n-CO_2R^{13}$, $-(CH_2)_n-(CHOR^8)_m-CO_2R^{13}$, Het-$(CH_2)_m-(CHOR^8)_m-CO_2R^{13}$, $-(CH_2)_n-(CHOR^8)_mZ_g-CO_2R^{13}$, Het-$(CH_2)_n-(CHOR^8)_m-Z_g-CO_2R^{13}$, $-(CH_2)_n-Z_g-(CH_2)_m-CO_2R^{13}$, $-(CH_2)_n-Z_g-(CH_2)_m-CO_2R^{13}$, $-(CH_2)_n-Z_g(CHOR^8)_m-Z_g-CO_2R^{13}$, Het-$(CH_2)_n-Z_g-(CHOR^8)_m-Z_g-CO_2R^{13}$, $-(CH_2)_n-CONH-C(=NR^{13})-NR^{13}R^{13}$, Het-$(CH_2)_n-CO-NH-C(=NR^{13})-NR^{13}R^{13}$, $-(CH_2)_n-Z_g-CONH-C(=NR^{13})-NR^{13}R^{13}$, Het-$(CH_2)_n-Z_g-CONH-C(=NR^{13})-NR^{13}R^{13}$, $-(CH_2)_n-NR^{10}-(CH_2)_m(CHOR^8)_n-CONH-C(=NR^{13})-NR^{13}R^{13}$, Het-$(CH_2)_n-NR^{10}-(CH_2)_m(CHOR^8)_n-CONH-C(=NR^{13})-NR^{13}R^{13}$, $-(CH_2)_n-(CHOR^8)_m-CONH-C(=NR^{13})-NR^{13}R^{13}$, Het-$(CH_2)_n-(CHOR^8)_m-CONH-C(=NR^{13})-NR^{13}R^{13}$, $-(CH_2)_n-(CHOR^8)_m-Z_g-CONH-C(=NR^{13})-NR^{13}R^{13}$, Het-$(CH_2)_n-(CHOR^8)_m-Z_g-CONH-C(=NR^{13})-NR^{13}R^{13}$, $-(CH_2)_n-Z_g-(CH_2)_m-CONH-C(=NR^{13})-NR^{13}R^{13}$, Het-$(CH_2)_n-Z_g-(CH_2)_mCONH-C(=NR^{13})-NR^{13}R^{13}$, $-(CH_2)_n-Z_g-(CHOR^8)_m-Z_g-CONH-C(=NR^{13})-NR^{13}R^{13}$, Het-$(CH_2)_n-Z_g-(CHOR^8)_m-Z_g-CONH-C(=NR^{13})-NR^{13}R^{13}$, $-(CH_2)_n-CONR^7-CONR^{13}R^{13}$, Het-$(CH_2)_n-CONR^7-CONR^{13}R^{13}$, $-(CH_2)_n-Z_g-CONR^7-CONR^{13}R^{13}$, $-(CH_2)_n-Z_g-CONR^7-CONR^{13}R^{13}$, $-(CH_2)_n-NR^{10}-(CH_2)_m(CHOR^8)_n-CONR^7-CONR^{13}R^{13}$, Het-$(CH_2)_n-NR^{10}-(CH_2)_m(CHOR^8)_n-CONR^7-CONR^{13}R^{13}$, $-(CH_2)_n-(CHOR^8)_m-CONR^7-CONR^{13}R^{13}$, Het-$(CH_2)_n-(CHOR^8)_m-CONR^7CONR^{13}R^{13}$, $-(CH_2)_n-(CHOR^8)_m-Z_g-CONR^7-CONR^{13}R^{13}$, Het-$(CH_2)_n-(CHOR^8)_m-Z_g-CNR^7-CONR^{13}R^{13}$, $-(CH_2)_n-Z_g-(CH_2)_m-CONR^7NR^{13}R^{13}$, Het-$(CH_2)_n-Z_g-(CH_2)_m-CONR^7-CONR^{13}R^{13}$, $-(CH_2)_n-Z_g(CHOR^8)_m-Z_g-CONR^7-CONR^{13}R^{13}$, Het-$(CH_2)_n-Z_g(CHOR^8)_m-Z_g-CONR^7-CONR^{13}R^{13}$, $-(CH_2)_n-CONR^7SO_2NR^{13}R^{13}$, Het-$(CH_2)_m-CONR^7SO_2NR^{13}R^{13}$, $-(CH_2)_n-Z_g-CONR^7SO_2NR^{13}R^{13}$, Het-$(CH_2)_m-Z_g-CONR^7SO_2NR^{13}R^{13}$, $-(CH_2)_n-NR^{10}-(CH_2)_m-(CHOR^8)_n-CONR^7SO_2NR^{13}R^{13}$, Het-$(CH_2)_m-NR^{10}-(CH_2)_m(CHOR^8)_n-CONR^7SO_2NR^{13}R^{13}$, $-(CH_2)_n-(CHOR^8)_n-CONR^7SO_2NR^{13}R^{13}$, Het-$(CH_2)_m-(CHOR^8)_m-CONR^7SO_2NR^{13}R^{13}$, $-(CH_2)_n-(CHOR^8)_m-Z_g-CONR^7SO_2NR^{13}R^{13}$, Het-$(CH_2)_n-(CHOR^8)_m-Z_g-CONR^7SO_2NR^{13}R^{13}$, $-(CH_2)_n-Z_g-(CH_2)_mCONR^7SO_2NR^{13}R^{13}$, Het-$(CH_2)_n-Z_g-(CH_2)_mCONR^7SO_2NR^{13}R^{13}$, $-(CH_2)_n-Z_g-(CHOR^8)_m-Z_g-CONR^7SO_2NR^{13}R^{13}$, Het-$(CH_2)_n-Z_g-(CHOR^8)_m-Z_g-CONR^7SO_2NR^{13}R^{13}$, $-(CH_2)_n-SO_2NR^{13}R^{13}$, Het-$(CH_2)_m-SO_2NR^{13}R^{13}$, $-(CH_2)_n-Z_g-SO_2NR^{13}R^{13}$, Het-$(CH_2)_m-Z_g-SO_2NR^{13}R^{13}$, $-(CH_2)_n-NR^{10}-(CH_2)_m(CHOR^8)_n-SO_2NR^{13}R^{13}$, Het-$(CH_2)_m-NR^{10}-(CH_2)_m(CHOR^8)_n-SO_2NR^{13}R^{13}$, $-(CH_2)_n-(CHOR^8)_m-SO_2NR^{13}R^{13}$, Het-$(CH_2)_m-(CHOR^8)_m-SO_2NR^{13}R^{13}$, $-(CH_2)_n-(CHOR^8)_m-Z_g-SO_2NR^{13}R^{13}$, Het-$(CH_2)_n-(CHOR^8)_m-Z_g-SO_2NR^{13}R^{13}$, $-(CH_2)_n-Z_g-(CH_2)_mSO_2NR^{13}R^{13}$, Het-$(CH_2)_n-Z_g-(CH_2)_mSO_2NR^{13}R^{13}$, $-(CH_2)_n-Z_g-(CHOR^8)_m-Z_g-SO_2NR^{13}R^{13}$, Het-$(CH_2)_n-Z_g-(CHOR^8)_m-Z_g-SO_2NR^{13}R^{13}$, $-(CH_2)_n-CONR^{13}R^{13}$, Het-$(CH_2)_m-CONR^{13}R^{13}$, $-(CH_2)_n-Z_g-CONR^{13}R^{13}$, Het-$(CH_2)_m-Z_g-CONR^{13}R^{13}$, $-(CH_2)_n-NR^{10}-(CH_2)_m(CHOR^8)_n-CONR^{13}R^{13}$, Het-$(CH_2)_m-NR^{10}-(CH_2)_m(CHOR^8)_n-CONR^{13}R^{13}$, $-(CH_2)_n-(CHOR^8)_m-CONR^{13}R^{13}$, Het-$(CH_2)_m-(CHOR^8)_m-CONR^{13}R^{13}$, $-(CH_2)_n-(CHOR^8)_m-Z_g-CONR^{13}R^{13}$, Het-$(CH_2)_m-(CHOR^8)_m-Z_g-CONR^{13}R^{13}$, $-(CH_2)_n-Z_g-(CH_2)_mCONR^{13}R^{13}$, Het-$(CH_2)_n-Z_g-(CH_2)_mCONR^{13}R^{13}$, $-(CH_2)_n-Z_g-(CHOR^8)_m-Z_g-CONR^{13}R^{13}$, Het-$(CH_2)_n-Z_g-(CHOR^8)_m-Z_g-CONR^{13}R^{13}$, $-(CH_2)_n-CONR^7COR^{13}$, Het-$(CH_2)_m-CONR^7COR^{13}$, $-(CH_2)_n-Z_g-CONR^7COR^{13}$, Het-$(CH_2)_m-Z_g-CONR^7COR^{13}$, $-(CH_2)_n-NR^{10}-(CH_2)_m(CHOR^8)_n-CONR^7COR^{13}$, Het-$(CH_2)_m-NR^{10}-(CH_2)_m(CHOR^8)_n-CONR^7COR^{13}$, $-(CH_2)_n-(CHOR^8)_m-CONR^7COR^{13}$, Het-$(CH_2)_m-(CHOR^8)_m-CONR^7COR^{13}$, $-(CH_2)_n-(CHOR^8)_m-Z_g-CONR^7COR^{13}$, Het-$(CH_2)_n-(CHOR^8)_m-Z_g-CONR^7COR^{13}$, $-(CH_2)_n-Z_g-(CH_2)_mCONR^7COR^{13}$, Het-$(CH_2)_n-Z_g-(CHOR^8)_m-Z_g-CONR^7COR^{13}$, $-(CH_2)_n-CONR^7CO_2R^{13}$, $-(CH_2)_n-Z_g-CONR^7CO_2R^{13}$, Het-$(CH_2)_m-Z_g-CONR^7CO_2R^{13}$, $-(CH_2)_n-NR^{10}-(CH_2)_m(CHOR^8)_n-CONR^7CO_2R^{13}$, Het-$(CH_2)_m-NR^{10}-(CH_2)_m(CHOR^8)_n-CONR^7CO_2R^{13}$, $-(CH_2)_n-(CHOR^8)_m-CONR^7CO_2R^{13}$, Het-$(CH_2)_m-(CHOR^8)_m-CONR^7CO_2R^{13}$, $-(CH_2)_n-(CHOR^8)_m-Z_g-CONR^7CO_2R^{13}$, Het-$(CH_2)_n-(CHOR^8)_m-Z_g-CONR^7CO_2R^{13}$, $-(CH_2)_n-Z_g-(CH_2)_mCONR^7CO_2R^{13}$, Het-$(CH_2)_n-Z_g-(CH_2)_mCONR^7CO_2R^{13}$, $-(CH_2)_n-Z_g-(CHOR^8)_m-Z_g-CONR^7CO_2R^{13}$, Het-$(CH_2)_n-Z_g-(CHOR^8)_m-Z_g-CONR^7CO_2R^{13}$, $-(CH_2)_n-NH-C(=NR^{13})-NR^{13}R^{13}$, Het-$(CH_2)_m-NH-C(=NR^{13})-NR^{13}R^{13}$, $-(CH_2)_n-Z_g-NH-C(=NR^{13})-NR^{13}R^{13}$, Het-$(CH_2)_m-Z_g-NH-C(=NR^{13})-NR^{13}R^{13}$, $-(CH_2)_n-NR^{10}-(CH_2)_m(CHOR^8)_n-NH-C(=NR^{13})-NR^{13}R^{13}$, Het-$(CH_2)_m-NR^{10}-(CH_2)_n(CHOR^8)_n-NH-C(=NR^{13})-NR^{13}R^{13}$, $-(CH_2)_n-(CHOR^8)_m-NH-C(=NR^{13})-NR^{13}R^{13}$, Het-$(CH_2)_m-(CHOR^8)_m-NH-C(=NR^{13})-NR^{13}R^{13}$, $-(CH_2)_n-(CHOR^8)_m-Z_g-NH-C(=NR^{13})-NR^{13}R^{13}$, Het-$(CH_2)_n-(CHOR^8)_m-Z_g-NH-C(=NR^{13})-NR^{13}R^{13}$, $-(CH_2)_n-Z_g-(CH_2)_mNH-C(=NR^{13})NR^{13}R^{13}$, Het-$(CH_2)_n-Z_g-(CH_2)_mNH-C(=NR^{13})-NR^{13}R^{13}$, $-(CH_2)_n-Z_g-(CHOR^8)_m-Z_g-NH-C(=NR^{13})-NR^{13}R^{13}$, Het-$(CH_2)_n-Z_g-(CHOR^8)_m-Z_g-NH-C(=NR^{13})-NR^{13}R^{13}$, $-(CH_2)_n-C(=NR^{13})-NR^{13}R^{13}$, Het-$(CH_2)_m-C(=NH)-NR^{13}R^{13}$, $(CH_2)_n-Z_g-C(=NH)-NR^{13}R^{13}$, Het-$(CH_2)_m-Z_g-C(=NH)-NR^{13}R^{13}$, $-(CH_2)_n-NR^{10}-(CH_2)_m(CHOR^8)_n-C(=NR^{13})-NR^{13}R^{13}$, Het-$(CH_2)_m-NR^{10}-(CH_2)_m(CHOR^8)_n-C(=NR^{13})-NR^{13}R^{13}$, $-(CH_2)_n-(CHOR^8)_m-C(=NR^{13})-NR^{13}R^{13}$, Het-$(CH_2)_m-(CHOR^8)_m-C(=NR^{13})-NR^{13}R^{13}$, Het-$(CH_2)_m-(CHOR^8)_m-C (=NR$^{13}$)—NR$^{13}$R$^{13}$, —(CH$_2$)$_n$—(CHOR$^8$)$_m$—Z$_g$—C(=NR$^{13}$)—NR$^{13}$R$^{13}$, Het-(CH$_2$)$_n$—(CHOR$^8$)$_m$—Z$_g$—C(=NR$^{13}$)—NR$^{13}$R$^{13}$, —(CH$_2$)$_n$—Z$_g$—(CH$_2$)$_m$—C(=NHC(=NR$^{13}$)—NR$^{13}$R$^{13}$, Het-(CH$_2$)$_n$—Z$_g$—(CH$_2$)$_m$—C(=NR$^{13}$)—NR$^{13}$R$^{13}$, —(CH$_2$)$_n$—Z$_g$—(CHOR$^8$)$_m$—Z$_g$—C(=NR$^{13}$)—NR$^{13}$R$^{13}$, Het-(CH$_2$)$_n$—Z$_g$—(CHOR$^8$)$_m$—Z$_g$—C(=NR$^{13}$)—NR$^{13}$R$^{13}$;

with the proviso wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

In a preferred embodiment, each —(CH$_2$)$_n$—Z$_g$—C(=NH)—NR$^{13}$R$^{13}$ falls within the scope of the structures described above and is, independently, —(CH$_2$)$_n$—CHNH(C=N)—NR$^{13}$R$^{13}$.

In another preferred embodiment, each Het-(CH$_2$)$_m$—NH—C(=NH)—NR$^{13}$R$^{13}$ falls within the scope of the structures described above and is, independently, —(CH$_2$)$_n$—NH—C(=NH)NHR$^{13}$.

In another preferred embodiment, each —(CH$_2$)$_n$—Z$_g$—(CHOR$^8$)$_m$—Z$_g$—CONR$^{13}$R$^{13}$ falls within the scope of the structures described above and is, independently, —(CH$_2$)$_n$—CONHCH$_2$(CHOH)$_m$—CONHR$^{13}$.

In another preferred embodiment, each Het-(CH$_2$)$_n$—Z$_g$—(CHOR$^8$)$_m$—Z$_g$—CONR$^{13}$R$^{13}$ falls within the scope of the structures described above and is, independently, —NH—C(=O)—CH$_2$—(CHOH)$_n$CH$_2$CONR$^{13}$R$^{13}$.

In another a preferred embodiment, each Het-(CH$_2$)$_m$—Z$_g$—C(=NH)—NR$^{13}$R$^{13}$ falls within the scope of the structures described above and is, independently, —O—(CH$_2$)$_m$—NH—C(=NH)—N(R$^{13}$)$_2$.

In another a preferred embodiment, each Het-(CH$_2$)$_m$—Z$_g$—CONR$^{13}$R$^{13}$ falls within the scope of the structures described above and is, independently, —O—(CH$_2$)$_m$—CHNH$_2$—CO$_2$NR$^{13}$R$^{13}$.

In another preferred embodiment, each R$^5$ falls within the scope of the structures described above and is, independently, —O—CH$_2$CHOHCH$_2$CONR$^{13}$R$^{13}$
—OCH$_2$CHOHCH$_2$CO$_2$R$^{13}$OCH$_2$CH$_2$CONR$^{13}$R$^{13}$
—OCH$_2$CH$_2$NHCOR$^{13}$
—CH$_2$CH$_2$CONR$^{13}$R$^{13}$
—OCH$_2$CH$_2$CONR$^{13}$R$^{13}$O—(CH$_2$)$_m$—CO$_2$R$^{13}$
—(CH$_2$)$_m$—CO$_2$R$^{13}$
—OCH$_2$CH$_2$CO$_2$R$^{13}$
—OCH$_2$CO$_2$R$^{13}$
—O—(CH$_2$)$_m$—NH—C(=NH)—NR$^{13}$)$_2$
—(CH$_2$)$_n$—NH—C(=NH)—N(R$^{13}$)$_2$
—NHCH$_2$(CHOH)$_2$—CONR$^{13}$R$^{13}$
—OCH$_2$CO$_2$R$^{13}$
—NHSO$_2$(CH$_2$)$_2$CONR$^{13}$R$^{13}$
—(CH$_2$)$_m$—NH—C(=O)—OR$^{13}$
—O—(CH$_2$)$_m$—NH—C(=O)—OR$^{13}$
—(CH$_2$)$_n$—NH—C(=O)—R$^{13}$
—O—(CH$_2$)$_m$—NH—C(=O)—R$^{13}$
—O—CH$_2$C(=ONR$^{13}$R$^{13}$
—CH$_2$NCO$_2$R$^{13}$
—NHCO$_2$R$^{13}$
—OCH$_2$CH$_2$CH$_2$CH$_2$CONR$^{13}$R$^{13}$
—SO$_2$CH$_2$CH$_2$CONR$^{13}$R$^{13}$
—OCH$_2$CH$_2$CHOHCH$_2$CONR$^{13}$R$^{13}$
—OCH$_2$CH$_2$NHCO$_2$R$^{13}$
—NH—C(=NH$_2$)—NR$^{13}$R$^{13}$
—OCH$_2$-(α-CHOH)$_2$—CONR$^{13}$R$^{13}$
—OCH$_2$CHOHCH$_2$CONHR$^{13}$
—(CH$_2$)$_m$—CHOH—CH$_2$—NHCO$_2$R$^{13}$
—O—(CH$_2$)$_m$—CHOH—CH$_2$—CO$_2$R$^{13}$
—(CH$_2$)$_m$—NHC(O)OR$^{13}$
—O—(CH$_2$)$_m$—NHC(O)OR$^{13}$
—OCH$_2$CH$_2$CH$_2$CONHR$^{13}$
—OCH$_2$CH$_2$NHCH$_2$(CHOH)$_2$CH$_2$CONHR$^{13}$
—OCH$_2$CH$_2$CONH(CH$_2$[(CHOH)$_2$CH$_2$NH$_2$)]$_2$
—(CH$_2$)$_4$—NHCO$_2$R$^{13}$
—(CH$_2$)$_4$—CONR$^{13}$R$^{13}$
—(CH$_2$)$_4$—CO$_2$R$^{13}$
—OCH$_2$CH$_2$CONHSOCH$_2$CH$_2$N(CH$_3$)$_2$
—O—(CH$_2$)$_m$—C(=NH)—N(R$^{13}$)$_2$
—(CH$_2$)$_n$—C(=NH)—N(R$^{13}$)$_2$
—(CH$_2$)$_3$—NHCO$_2$R$^{13}$—(CH$_2$)$_3$CONHCO$_2$R$^{13}$
—O—(CH$_2$)$_m$—NH—NH—C(=NH)—N(R$^{13}$)$_2$
—(CH$_2$)$_n$—NH—NH—C(=NH)—N(R$^{13}$)$_2$, or
—O—CH$_2$—CHOH—CH$_2$—NH—C(=NH)—N(R$^{13}$)$_2$;

There are four R$^6$ groups present on the ring in formula (A). Each R$^6$ may be each, independently, —R$^7$, —OR$^{11}$, —N(R$^7$)$_2$, —(CH$_2$)$_m$, —OR$^8$,
—O—(CH$_2$)$_m$—OR$^8$, —(CH$_2$)$_n$—NR$^7$R$^{10}$, —O—(CH$_2$)$_m$—NR$^7$R$^{10}$,
—(CH$_2$)$_n$(CHOR$^8$)(CHOR$^8$)$_n$—CH$_2$OR$^8$, —O—(CH$_2$)$_m$(CHOR$^8$)(CHOR$^8$), —CH$_2$OR$^8$,
—(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$,
—O—(CH$_2$CH$_2$O), —CH$_2$CH$_2$NR$^7$R$^{10}$, —(CH$_2$)$_n$—C(=O)NR$^7$R$^{10}$,
—O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$,
—(CH$_2$)$_n$—NR$^{10}$—CH$_2$(CHOR$^8$)(CHOR$^8$)$_n$—CH$_2$OR$^8$,
—O—(CH$_2$)$_m$—NR$^{10}$—CH$_2$(CHOR$^8$)(CHOR$^8$)$_n$—CH$_2$OR$^8$,
—(CH$_2$)$_n$—CO$_2$R$^7$, —O—(CH$_2$)$_m$—CO$_2$R$^7$, —OSO$_3$H, —O-glucuronide, —O-glucose, or

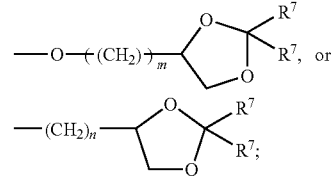

In addition, one of more of the R$^6$ groups can be one of the R$^5$ groups which fall within the broad definition of R$^6$ set forth above.

When two R$^6$ are —OR$^{11}$ and are located adjacent to each other on a phenyl ring, the alkyl moieties of the two R$^6$ groups may be bonded together to form a methylenedioxy group, i.e., a group of the formula —O—CH$_2$—O—.

As discussed above, R$^6$ may be hydrogen. Therefore, 1, 2, 3, or 4 R$^6$ groups may be other than hydrogen. Preferably at most 3 of the R$^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n maybe 0, 1, 2, 3, 4, 5, 6, or 7.

Each Q in formula (A) is C—R$^5$, C—R$^6$, or a nitrogen atom, where at most three Q in a ring are nitrogen atoms. Thus, there may be 1, 2, or 3 nitrogen atoms in a ring. Preferably, at most two Q are nitrogen atoms. More preferably, at most one Q is a nitrogen atom. In one particular embodiment, the nitrogen atom is at the 3-position of the ring. In another embodiment of the invention, each Q is either C—R$^5$ or C—R$^6$, i.e., there are no nitrogen atoms in the ring.

More specific examples of suitable groups represented by formula (A) are shown in formulas (B)-(E) below:

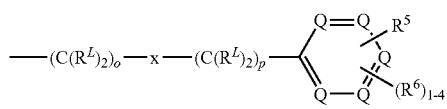
(A)

where o, x, p, $R^5$, and $R^6$, are as defined above;

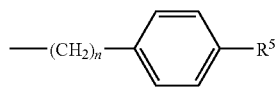
(C)

where n is an integer from 1 to 10 and $R^5$ is as defined above;

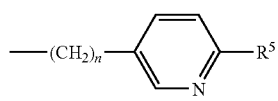
(D)

where n is an integer from 1 from 10 and $R^5$ is as defined above;

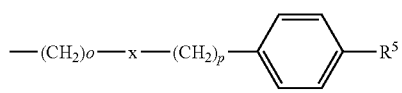
(E)

where o, x, p, and $R^5$ are as defined above.

In a preferred embodiment of the invention, Y is —$NH_2$.
In another preferred embodiment, $R^2$ is hydrogen.
In another preferred embodiment, $R^1$ is hydrogen.
In another preferred embodiment, X is chlorine.
In another preferred embodiment, $R^3$ is hydrogen.
In another preferred embodiment, $R^L$ is hydrogen.

In another preferred embodiment, o is 4.
In another preferred embodiment, p is 0.
In another preferred embodiment, the sum of o and p is 4.
In another preferred embodiment, x represents a single bond.
In another preferred embodiment, $R^6$ is hydrogen.
In another preferred embodiment, at most one Q is a nitrogen atom.
In another preferred embodiment, no Q is a nitrogen atom.
In a preferred embodiment of the present invention:
X is halogen;
Y is —$N(R^7)_2$;
$R^1$ is hydrogen or $C_1$-$C_3$ alkyl;
$R^2$ is —$R^7$, —$OR^7$, $CH_2O^7$, or —$CO_2R^7$;
$R^3$ is a group represented by formula (A); and
$R^4$ is hydrogen, a group represented by formula (A), or lower alkyl;

In another preferred embodiment of the present invention:
X is chloro or bromo;
Y is —$N(R^7)_2$;
$R^2$ is hydrogen or $C_1$-$C_3$ alkyl;
at most three $R^6$ are other than hydrogen as described above;
at most three $R^L$ are other than hydrogen as described above; and
at most 2 Q are nitrogen atoms.

In another preferred embodiment of the present invention:
Y is —$NH_2$;

In another preferred embodiment of the present invention:
$R^4$ is hydrogen;
at most one $R^L$ is other than hydrogen as described above;
at most two $R^6$ are other than hydrogen as described above; and
at most 1 Q is a nitrogen atom.

In another preferred embodiment of the present invention the compound of formula (1) is represented by the formula:

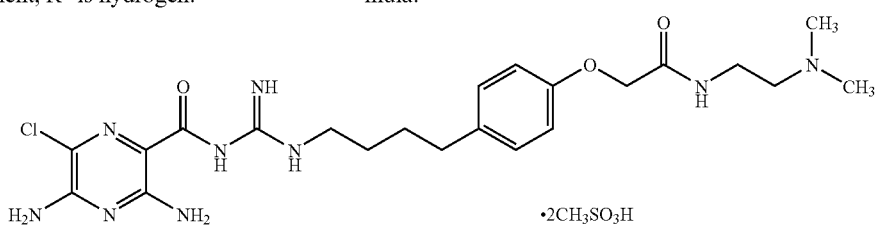

In another preferred embodiment of the present invention the compound of formula (1) is represented by the formula:

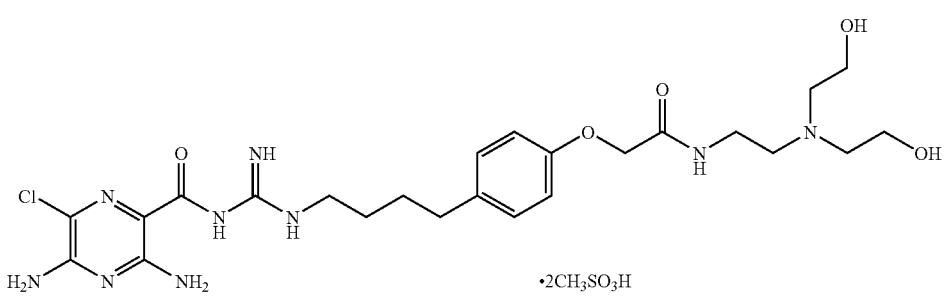

In another preferred embodiment of the present invention the compound of formula (1) is represented by the formula:

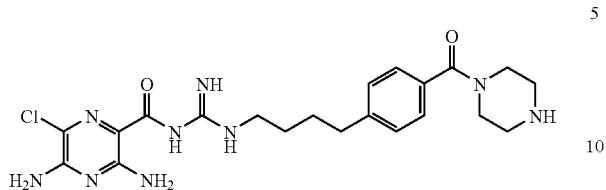

In another preferred embodiment of the present invention the compound of formula (1) is represented by the formula:

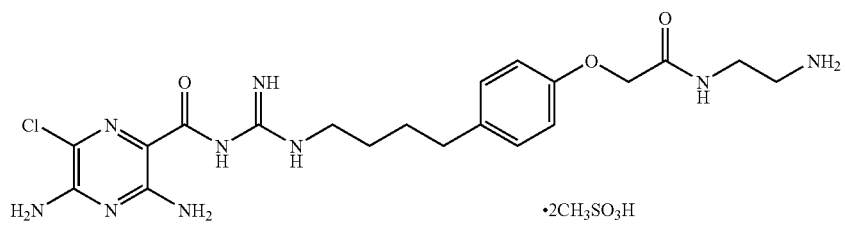

·2CH$_3$SO$_3$H

In another preferred embodiment of the present invention the compound of formula (1) is represented by the formula:

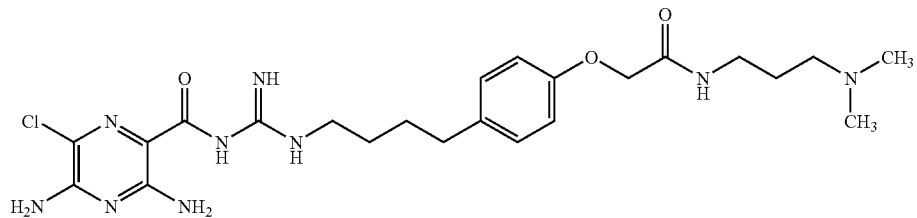

In another preferred embodiment of the present invention the compound of formula (1) is represented by the formula:

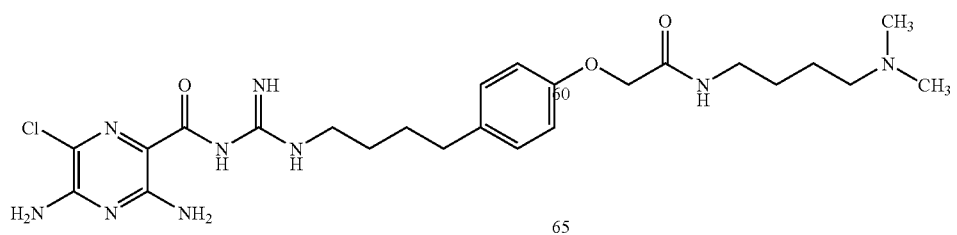

In another preferred embodiment of the present invention the compound of formula (1) is represented by the formula:

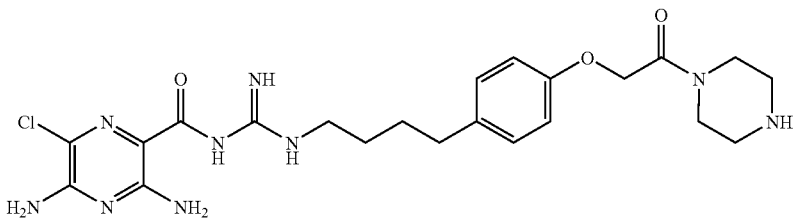

In another preferred embodiment of the present invention the compound of formula (1) is represented by the formula:

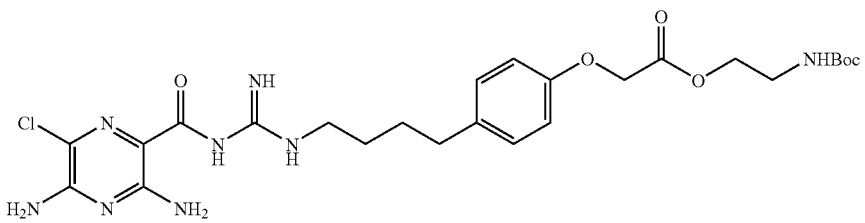

In another preferred embodiment of the present invention the compound of formula (1) is represented by the formula:

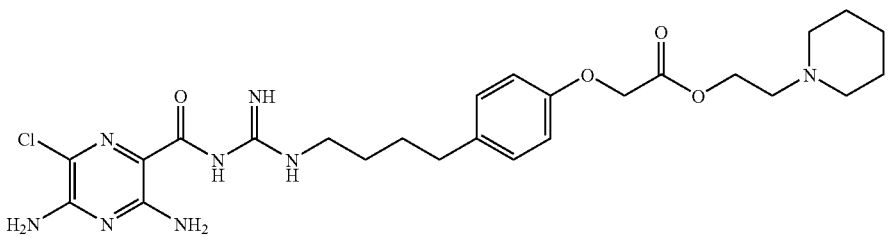

In another preferred embodiment of the present invention the compound of formula (1) is represented by the formula:

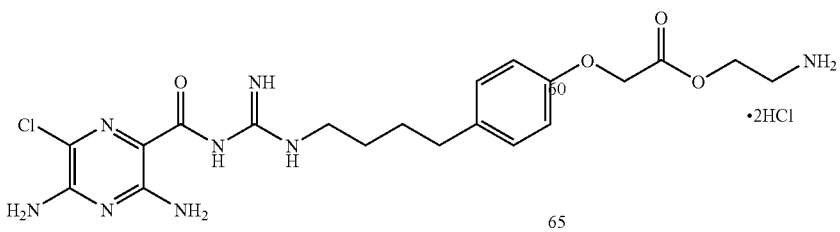

In another preferred embodiment of the present invention the compound of formula (1) is represented by the formula:

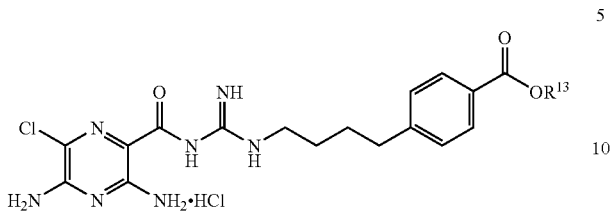

In another preferred embodiment of the present invention the compound of formula (1) is represented by the formula:

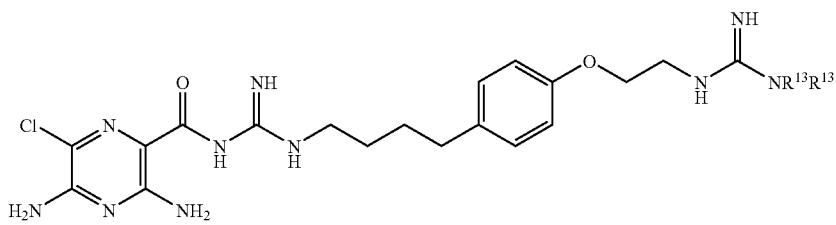

In another preferred embodiment of the present invention the compound of formula (1) is represented by the formula:

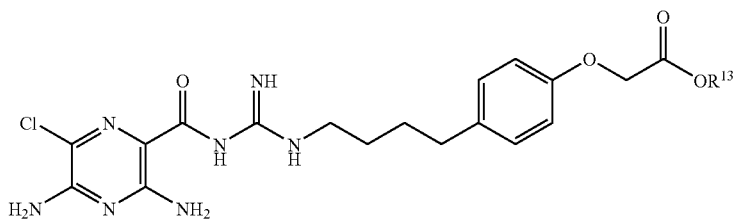

In another preferred embodiment of the present invention the compound of formula (1) is represented by the formula:

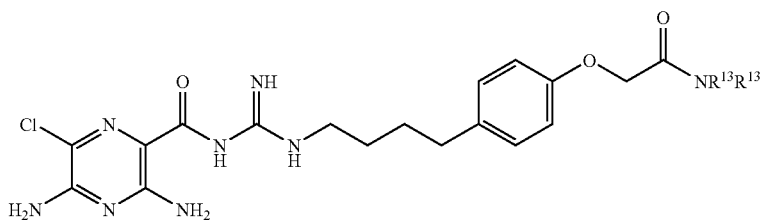

In another preferred embodiment of the present invention the compound of formula (1) is represented by the formula:

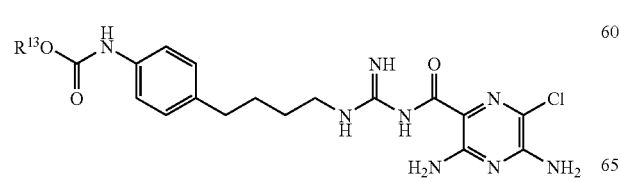

In another preferred embodiment of the present invention the compound of formula (1) is represented by the formula:

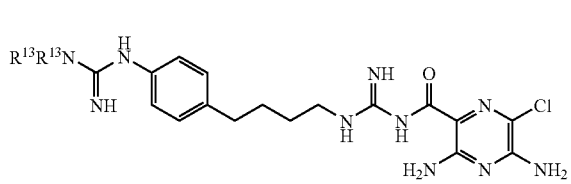

In another preferred embodiment of the present invention the compound of formula (1) is represented by the formula:

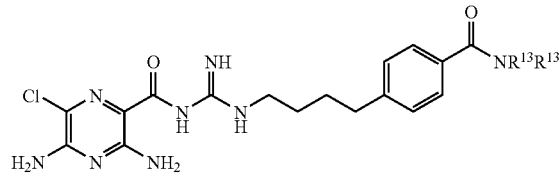

In another preferred embodiment of the present invention the compound of formula (1) is represented by the formula:

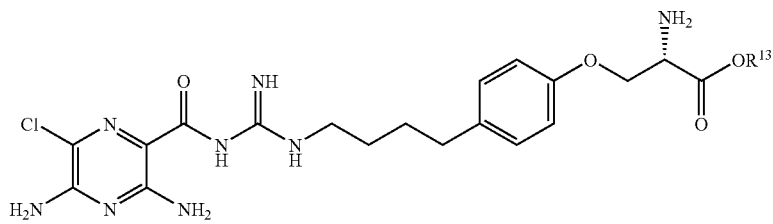

In another preferred embodiment of the present invention the compound of formula (1) is represented by the formula:

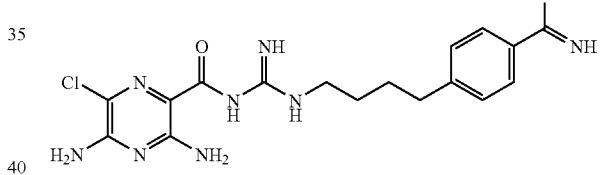

In another preferred embodiment of the present invention the compound of formula (1) is represented by the formula:

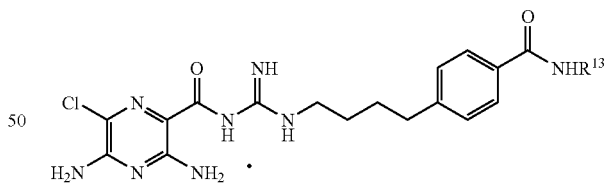

In another preferred embodiment of the present invention the compound of formula (1) is represented by the formula:

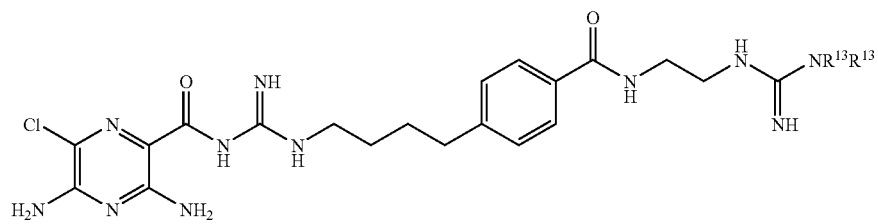

In another preferred embodiment of the present invention the compound of formula (1) is represented by the formula:

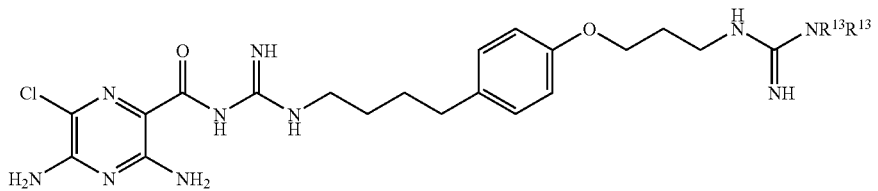

In another preferred embodiment of the present invention the compound of formula (1) is represented by the formula:

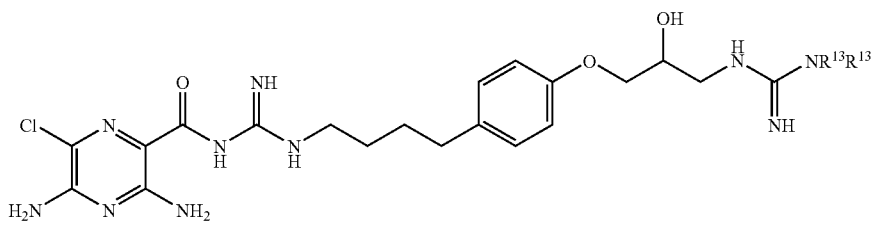

In another preferred embodiment of the present invention the compound of formula (1) is represented by the formula:

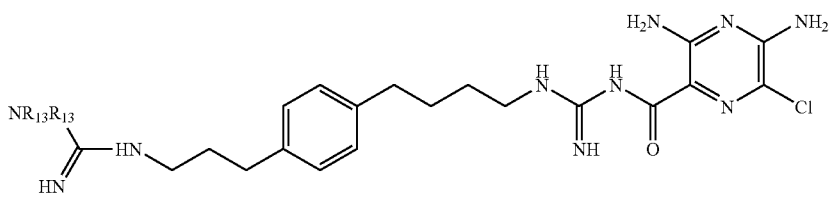

In another preferred embodiment of the present invention the compound of formula (1) is represented by the formula:

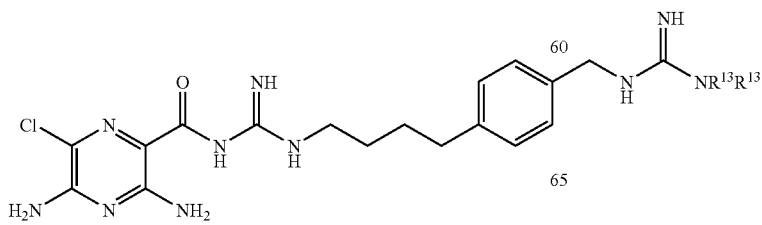

In another preferred embodiment of the present invention the compound of formula (1) is represented by the formula:

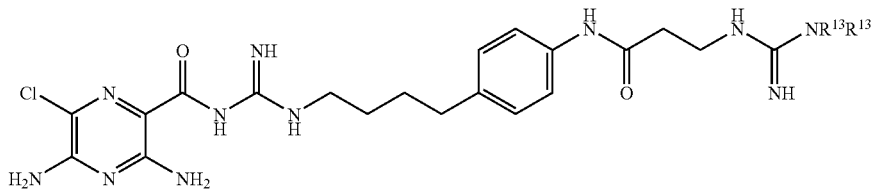

In another preferred embodiment of the present invention the compound of formula (1) is represented by the formula:

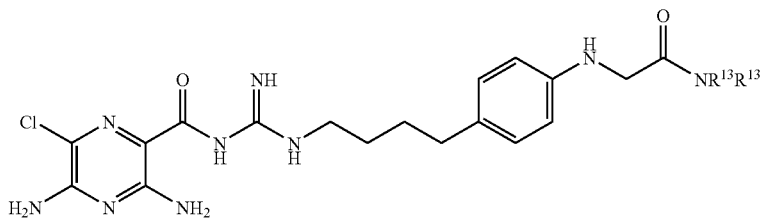

In another preferred embodiment of the present invention the compound of formula (1) is represented by the formula:

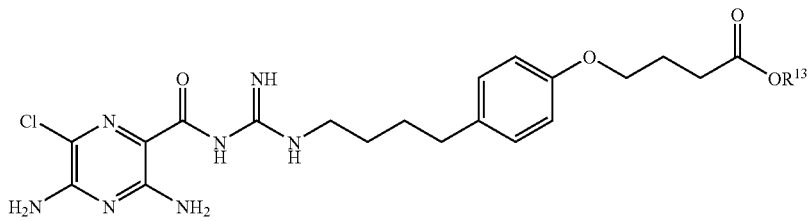

In another preferred embodiment of the present invention the compound of formula (1) is represented by the formula:

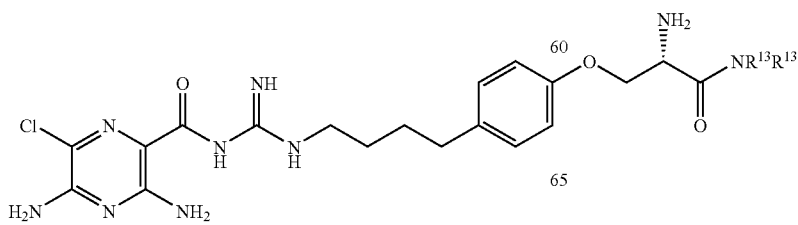

In another preferred embodiment of the present invention the compound of formula (1) is represented by the formula:

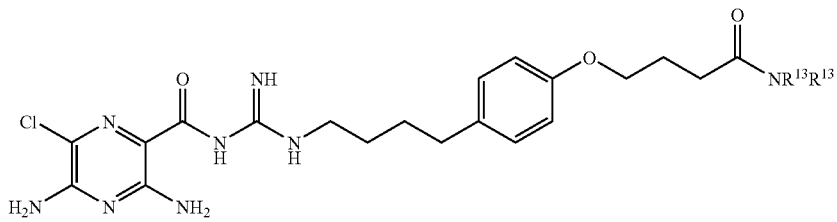

In another preferred embodiment of the present invention the compound of formula (1) is represented by the formula:

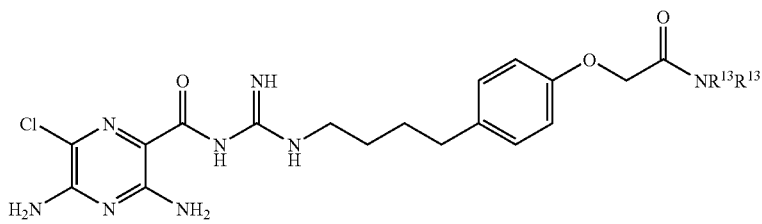

In another preferred embodiment of the present invention the compound of formula (1) is represented by the formula:

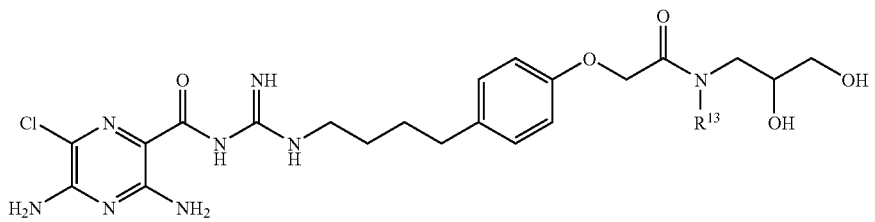

In another preferred embodiment of the present invention the compound of formula (1) is represented by the formula:

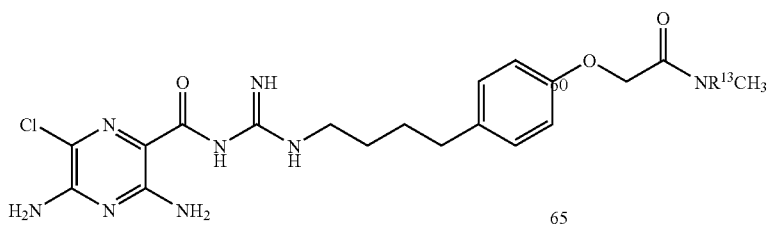

In another preferred embodiment of the present invention the compound of formula (1) is represented by the formula:

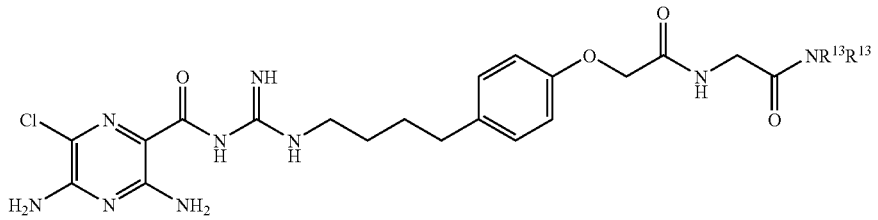

In another preferred embodiment of the present invention the compound of formula (1) is represented by the formula:

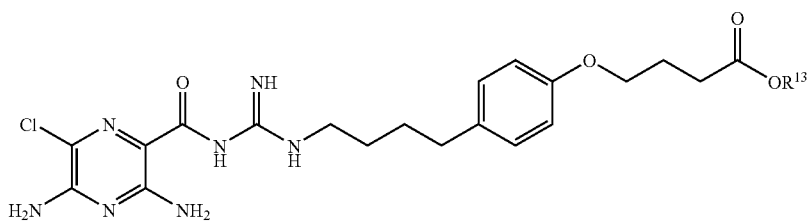

In another preferred embodiment of the present invention the compound of formula (1) is represented by the formula:

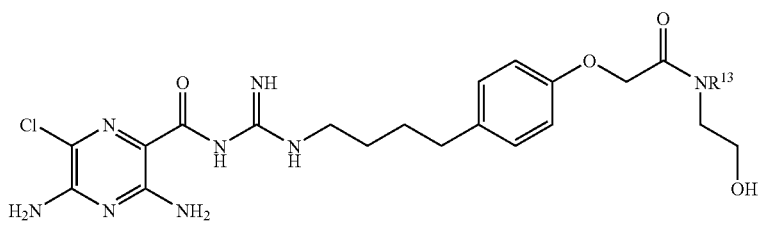

In another preferred embodiment of the present invention the compound of formula (1) is represented by the formula:

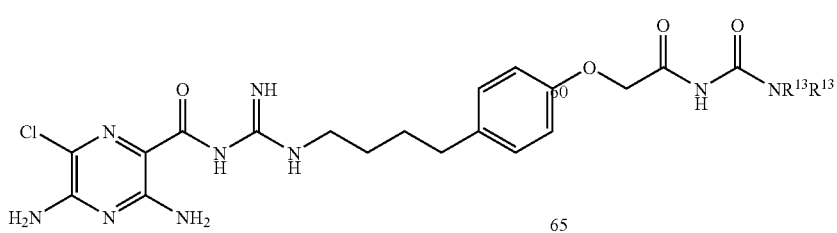

In another preferred embodiment of the present invention the compound of formula (1) is represented by the formula:

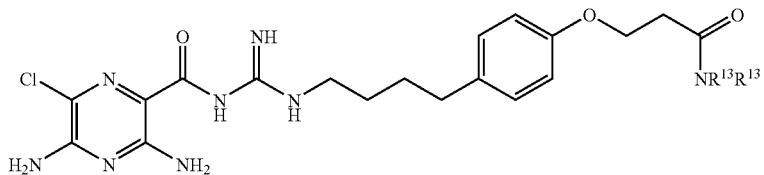

In another preferred embodiment of the present invention the compound of formula (1) is represented by the formula:

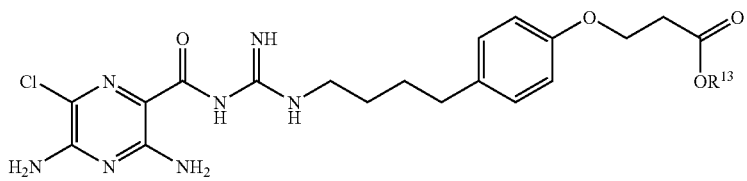

In another preferred embodiment of the present invention the compound of formula (1) is represented by the formula:

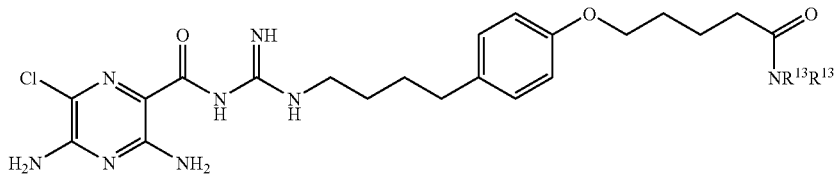

In another preferred embodiment of the present invention the compound of formula (1) is represented by the formula:

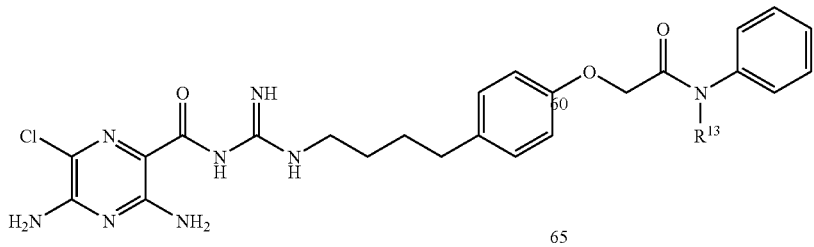

In another preferred embodiment of the present invention the compound of formula (1) is represented by the formula:

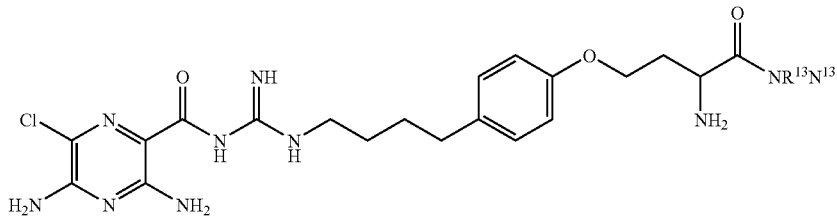

In another preferred embodiment of the present invention the compound of formula (1) is represented by the formula:

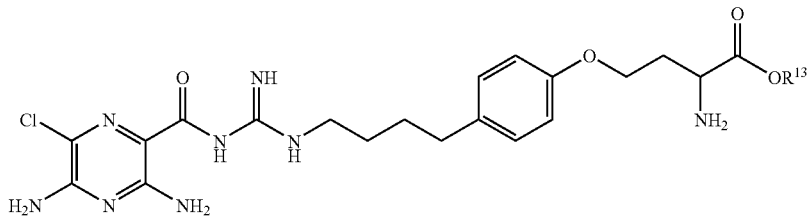

In another preferred embodiment of the present invention the compound of formula (1) is represented by the formula:

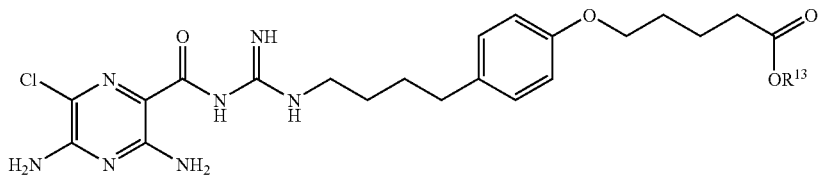

In another preferred embodiment of the present invention the compound of formula (1) is represented by the formula:

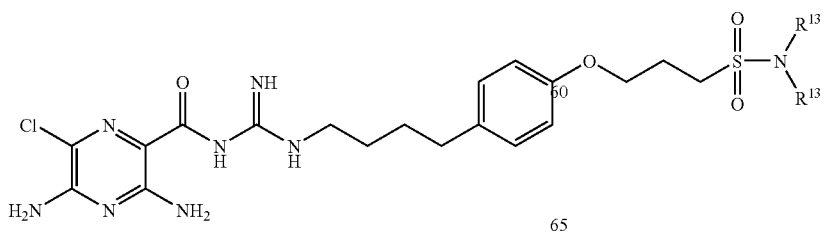

In another preferred embodiment of the present invention the compound of formula (1) is represented by the formula:

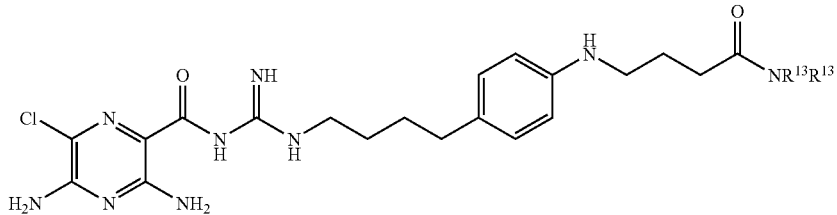

In another preferred embodiment of the present invention the compound of formula (1) is represented by the formula:

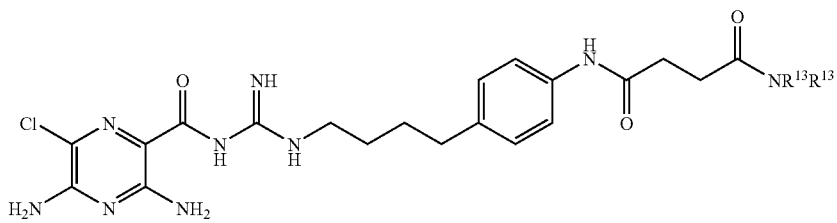

In another preferred embodiment of the present invention the compound of formula (1) is represented by the formula:

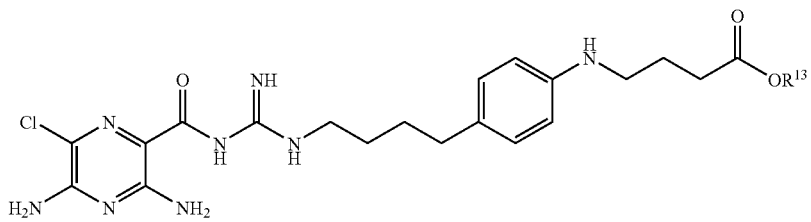

In another preferred embodiment of the present invention the compound of formula (1) is represented by the formula:

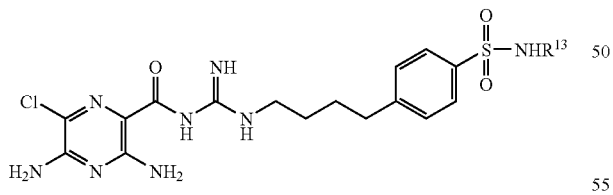

In another preferred embodiment of the present invention the compound of formula (1) is represented by the formula:

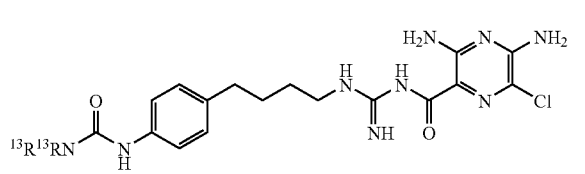

In another preferred embodiment of the present invention the compound of formula (1) is represented by the formula:

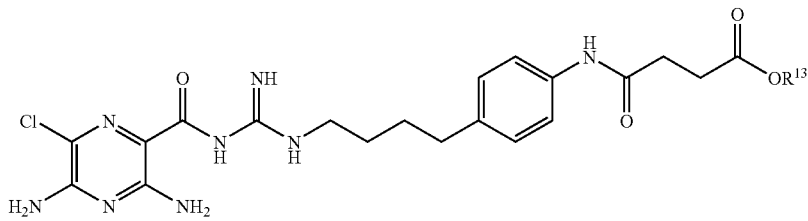

In another preferred embodiment of the present invention the compound of formula (1) is represented by the formula:

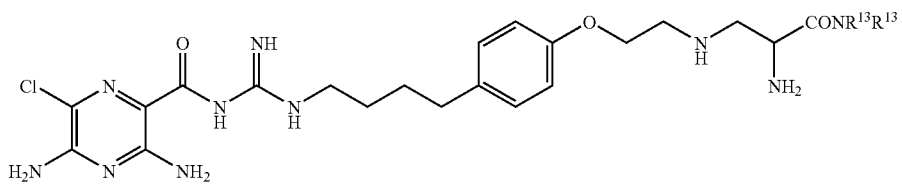

In another preferred embodiment of the present invention the compound of formula (1) is represented by the formula:

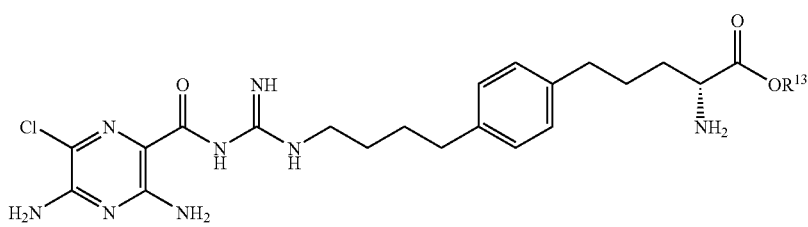

In another preferred embodiment of the present invention the compound of formula (1) is represented by the formula:

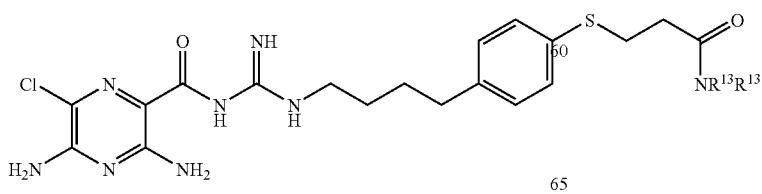

In another preferred embodiment of the present invention the compound of formula (1) is represented by the formula:

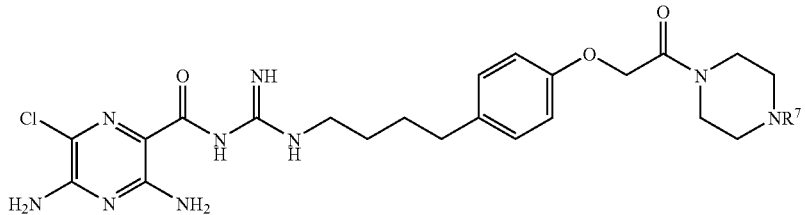

In another preferred embodiment of the present invention the compound of formula (1) is represented by the formula:

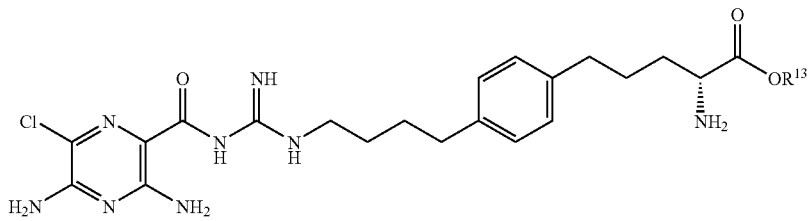

In another preferred embodiment of the present invention the compound of formula (1) is represented by the formula:

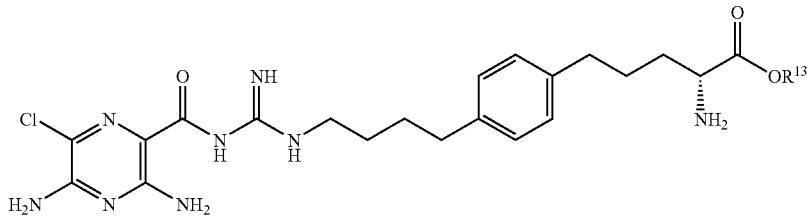

In another preferred embodiment of the present invention the compound of formula (1) is represented by the formula:

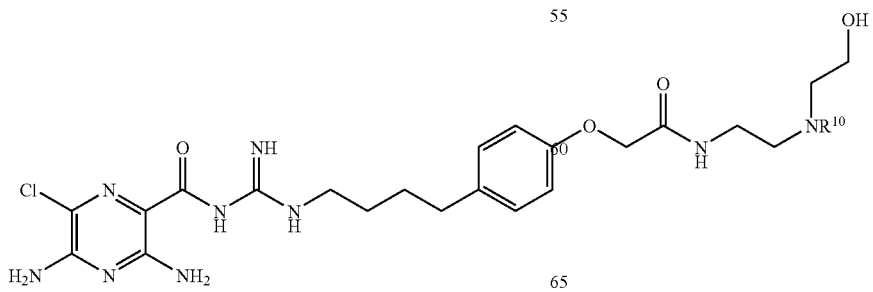

In another preferred embodiment of the present invention the compound of formula (1) is represented by the formula:

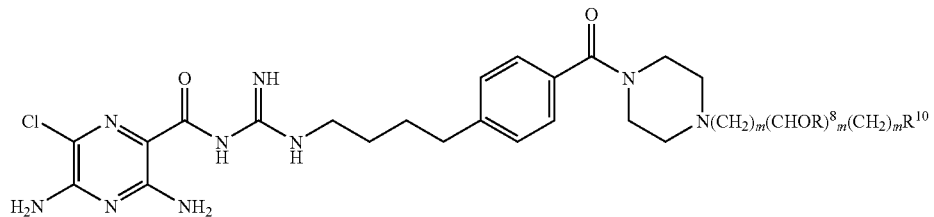

In another preferred embodiment of the present invention the compound of formula (1) is represented by the formula:

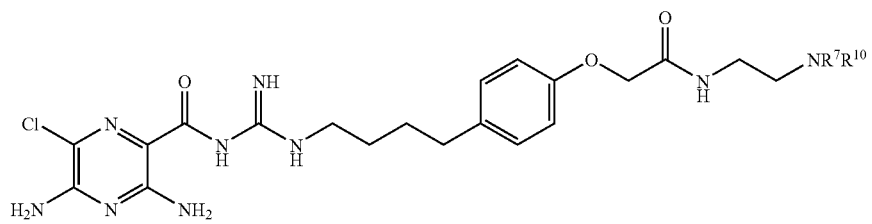

In another preferred embodiment of the present invention the compound of formula (1) is represented by the formula:

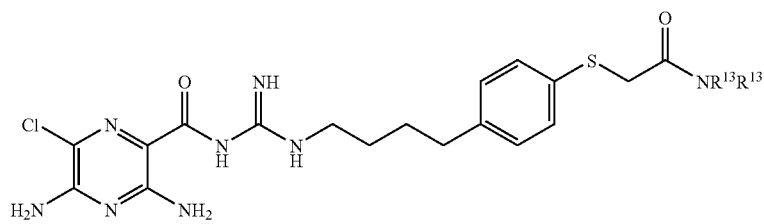

In another preferred embodiment of the present invention the compound of formula (1) is represented by the formula:

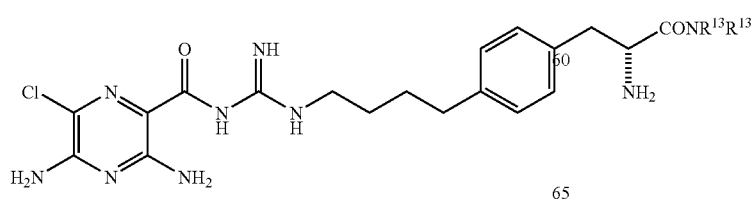

In another preferred embodiment of the present invention the compound of formula (1) is represented by the formula:

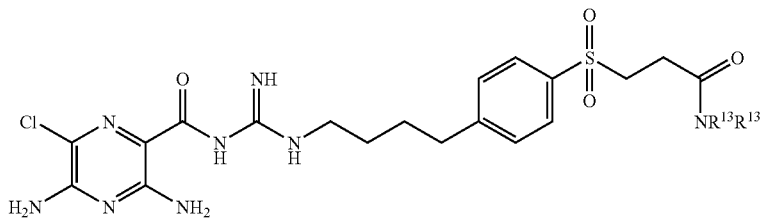

In another preferred embodiment of the present invention the compound of formula (1) is represented by the formula:

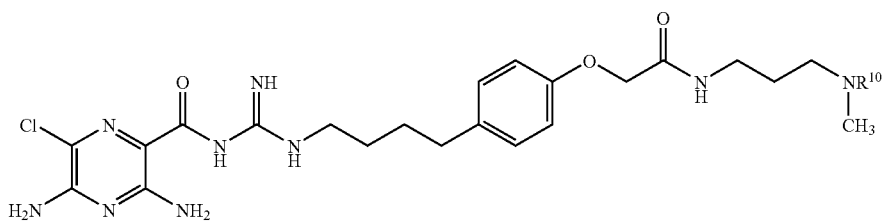

In another preferred embodiment of the present invention the compound of formula (1) is represented by the formula:

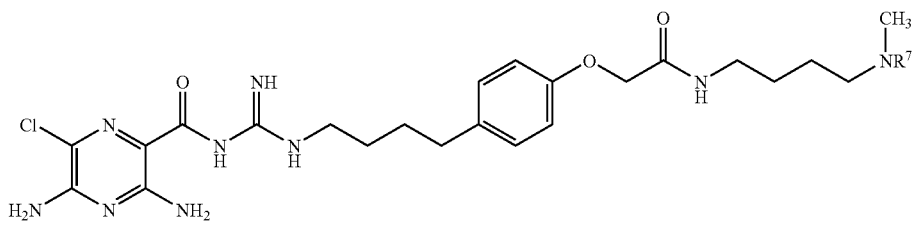

In another preferred embodiment of the present invention the compound of formula (1) is represented by the formula:

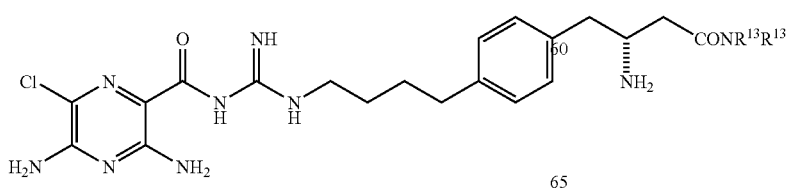

In another preferred embodiment of the present invention the compound of formula (1) is represented by the formula:

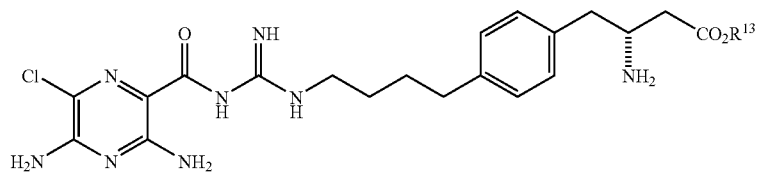

In another preferred embodiment of the present invention the compound of formula (1) is represented by the formula:

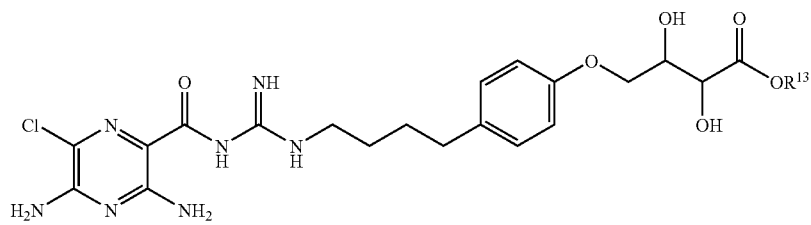

In another preferred embodiment of the present invention the compound of formula (1) is represented by the formula:

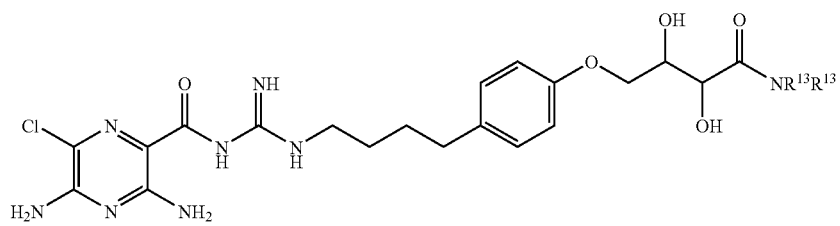

In another preferred embodiment of the present invention the compound of formula (1) is represented by the formula:

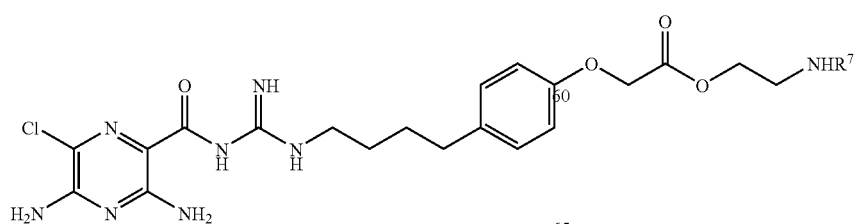

In another preferred embodiment of the present invention the compound of formula (1) is represented by the formula:

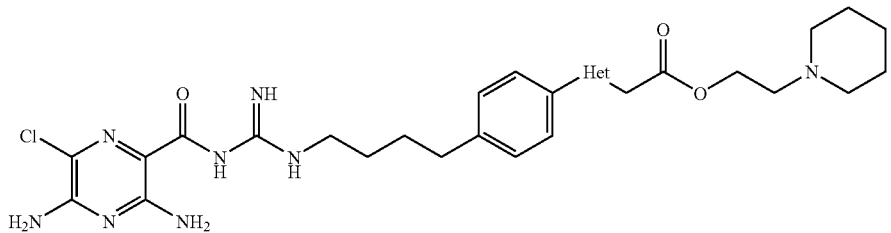

In another preferred embodiment of the present invention the compound of formula (1) is represented by the formula:

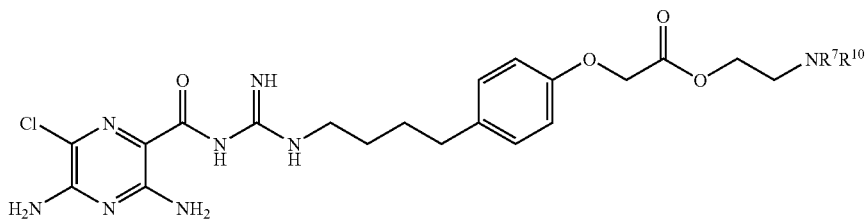

In another preferred embodiment of the present invention the compound of formula (1) is represented by the formula:

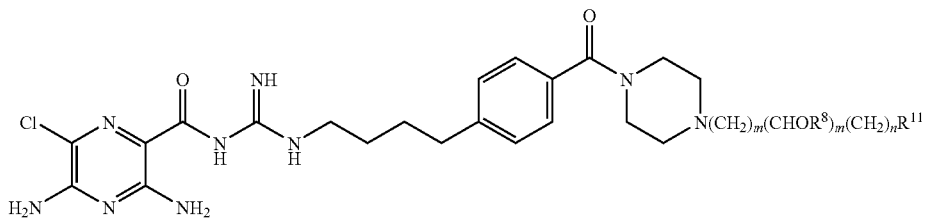

In another preferred embodiment of the present invention the compound of formula (1) is represented by the formula:

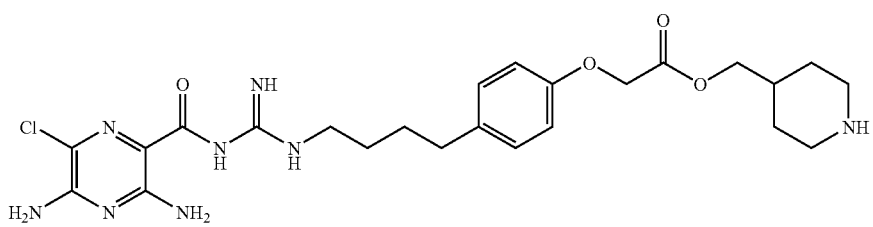

The compounds of formula (1) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formula (I) are embraced by the present invention. All mixtures of such enantiomers and diastereomers are within the scope of the present invention.

Without being limited to any particular theory, it is believed that the compounds of formula (I) function in vivo as sodium channel blockers. By blocking epithelial sodium channels present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., staphylococcus infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genitourethral surfaces, ocular surfaces or surfaces of the eye, the inner ear and the middle ear. For example, the active compounds of the present invention may be administered by any suitable means, including locally/topically, orally, or rectally, in an effective amount.

The compounds of the present invention are also useful for treating a variety of functions relating to the cardiovascular system. Thus, the compounds of the present invention are useful for use as antihypertensive agents. The compounds may also be used to reduce blood pressure and to treat edema. In addition, the compounds of the present invention are also useful for promoting diuresis, natriuresis, and saluresis. The compounds may be used alone or in combination with beta blockers, ACE inhibitors, HMGCoA, reductase inhibitors, calcium channel blockers and other cardiovascular agents to treat hypertension, congestive heart failure and reduce cardiovascular mortality.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. Nos. 6,264,975, 5,656,256, and 5,292,498, each of which is incorporated herein by reference.

Bronchodiloators can also be used in combination with compounds of the present invention. These bronchodilators include, but are not limited to, β-adrenergic agonists including but not limited to epinephrine, isoproterenol, fenoterol, albutereol, terbutalin, pirbuterol, bitolterol, metaproterenol, iosetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 µm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by an suitable means know in the art, such as by nose drops, mists., etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813, 397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^{4}$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{12}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 (19$^{th}$ ed. 1995), incorporated herein by reference. Pharmaceutical formulations suitable for nasal administration may be prepared as described in U.S. Pat. No. 4,389,393 to Schor; U.S. Pat. No. 5,707,644 to Illum; U.S. Pat. No. 4,294,829 to Suzuki; and U.S. Pat. No. 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below:

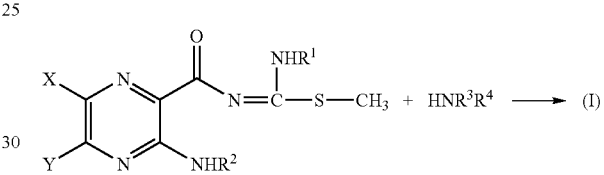

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Other methods useful for the preparation of these compounds, especially for the preparation of the novel HNR$^3$R$^4$ fragment. are described in, for example (Ser. No. 10/367,497), (Ser. No. 10/076,571), (Ser. No. 60/495,725), (Ser. No. 60/495,712) and (Ser. No. 60/495,720), incorporated herein by reference. Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog or sheep airways are seeded onto porous 0.4 micron Snapwell™ Inserts (CoStar), cultured at air-liquid interface (ALI) conditions in hormonally defined media, and assayed for sodium transport activity ($I_{SC}$ in µA/cm$^2$) while bathed in Krebs Bicarbonate Ringer (KBR) in Ussing chambers. All test drug additions are to the lumenal bath with half-log dose addition protocols (from $1 \times 10^{-11}$ M to $3 \times 10^{-5}$ M), and the cumulative change in $I_{SC}$ (inhibition) recorded. All drugs are prepared in dimethyl sulfoxide as stock solutions at a concentration of $1 \times 10^{-2}$ M and stored at $-20°$ C. Six preparations are typically run in parallel; one preparation per run incorporates a positive control. All data from the voltage clamps are collected via a computer interface and analyzed off-line.

Dose-effect relationships for all compounds are considered and analyzed by the Prism 3.0 program. $EC_{50}$ values, maximal effective concentrations are calculated and compared to positive controls.

In Vitro Durability of Sodium Channel Blockers: Surface Liquid Absorption, Transport, and Metabolic Profile The airway bronchial epithelium is an absorptive epithelium (actively absorbs sodium and therefore water from the lumenal to serosal direction. Using a gravimetric (weighing) procedure, the lumenal surface liquid is weighed and changes recorded up to 36 h. An applied starting volume of buffer (modified Krebs-Henseleit Bicarbonate buffer solution) with and without equimolar concentrations of selected novel or commercially available sodium channel blockers are added to the starting buffer, and at selected time points the lumenal surface liquid mass is weighed and the mass recorded in mg. In addition, during the assay, samples are collected from both the surface liquid and serosal compartment, after which the wells re-weighted and weights recorded. The samples collected are analyzed using HPLC and or mass spectrometry, and the concentration of sodium channel blocker calculated, with any conjugate or metabolite noted.

Solubility of Compounds in Water or Sodium Chloride Solution

Compound solubility was measured in water, 0.12 or 0.9% sodium chloride solution at ambient temperature for up to 10 days. Using a UV/Visable Spectrophotometer and applying Beer's Law with the calculated extinction coeffecient of amiloride (18.6 mM, absorbance values at 362 nm taken from D. Mazzo 1986) the free base concentration in solution was calculated at specified time points. All samples were stored for the duration of the experiment in a single/closure system consisting of glass vials with a stopper-top closure. The vials were maintained at ambient temperature, in the dark, and in the upright position. Compound stability was measured using reverse phase high performance liquid chromatography on the final filtered pulled sample (day 10).

Confocal Microscopy Assay of Amiloride Congener Uptake

Virtually all molecules studied fluoresce in the ultraviolet range. This property of these molecules may be used to directly measure cellular update using x—Z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x—Z images are obtained with time and the magnitude of fluorescence accumulating in the cellular compartment is quantitated and plotted as a change in fluorescence versus time.

Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

In Vivo Assay in Sheep

Methods

Animal Preparation: Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 μm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of activity at t—Zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Parn LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paried t-test to identify differences between specific pairs. Significance was accepted when P was less than or equal to 0.05. Slope values (calculated from data collected during the initial 45 minutes after dosing in the t—Zero assessment) for mean MCC curves were calculated using linear least square regression to assess differences in the initial rates during the rapid clearance phase.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. All reagents and solvents were purchased from Aldrich Chemical Corp. and used without further purification. NMR spectra were obtained on either a Bruker WM 360 ($^1$H NMR at 360 MHz and $^{13}$C NMR at 90 MHz) or a Bruker AC 300 ($^1$H NMR at 300 MHz and $^{13}$C NMR at 75 MHz). Flash chromatography was performed on a Flash Elute™ system from Elution Solution (PO Box 5147, Charlottesville, Va. 22905) charged with a 90 g silica gel cartridge (40M FSO-0110-040155, 32-63 μm) at 20 psi (N$_2$). GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: H$_2$ at 40 ml/min., Air at 400 ml/min. Carrier gas: Split Ratio 16:1, N$_2$ flow at 15 ml/min., N$_2$ velocity at 18 cm/sec. The temperature program is 70° C. for 0-3 min, 70-300° C. from 3-10 min, 300° C. from 10-15 min.

HPLC analysis was performed on a Gilson 322 Pump, detector UV/Vis-156 at 360 nm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

Synthesis of 2-(4-{4-[N'-(3,5-diamino-6-chloropyrazine-2-carbonyl)guanidino]-butyl}phenoxy)-N-(3-dimethylaminopropyl)acetamide dimethanesulfonate (PSA 24304)

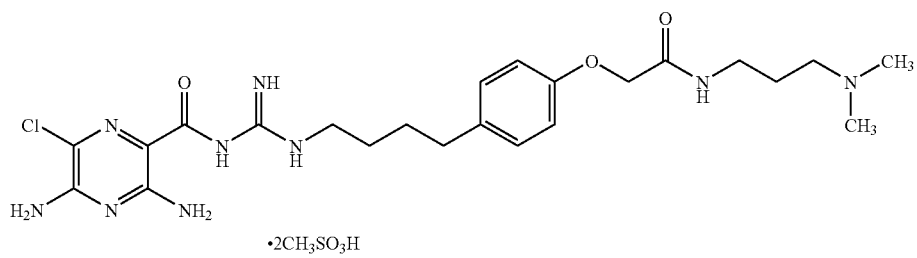

PSA 24304

(4-{4-[(3-Dimethylaminopropylcarbamoyl)methoxy]phenyl}butyl)carbamic acid benzyl ester (3)

A solution of 1 (0.50 g, 1.39 mmol) and CDI (0.25 g, 1.54 mmol) in THF (15 mL) was heated at 40° C. for 1 h. Then 2 (0.15 g, 1.47 mmol) was added into the reaction mixture at that temperature. The resulting solution was slowly cooled down to room temperature and further stirred at the temperature overnight. After that, the solvent was removed under reduced pressure and the residue was purified by Flash™ chromatography (BIOTAGE, Inc) (9:0.9:0.1 dichloromethane/methanol/concentrated ammonium hydroxide, v/v) to provide 3 (0.4 g, 61%) as a white solid. $^1$H NMR (500 MHz, CD$_3$OD) δ 1.48 (m, 2H), 1.64 (m, 2H), 1.72 (m, 2H), 2.14 (s, 6H), 2.27 (m, 2H), 2.56 (m, 2H), 3.10 (m, 2H), 3.29 (m, 3H), 4.41 (s, 2H), 5.09 (s, 2H), 6.85 (d, 2H), 7.09 (d, 2H), 7.31 (m, 5H). m/z (ESI) 442.

2-[4-(4-Aminobutyl)phenoxy]-N-(3-dimethylaminopropyl)acetamide (4)

A suspension of 3 (377 mg, 0.85 mmol) and 10% palladium on carbon (0.30 g, 50% wet) in methanol (15 mL) was stirred at room temperature for 2 h under atmospheric pressure of hydrogen. The mixture was then filtered through a Celite pad and the solvent was evaporated to provide 4 (208 mg, 80%) as a white solid. The crude product was directly used in the next step without purification. $^1$H NMR (300 MHz, CD$_3$OD) δ 1.61 (m, 6H), 2.11 (s, 6H), 2.32 (m, 2H), 2.65 (m, 4H), 3.28 (m, 2H), 4.45 (s, 2H), 6.90 (d, 2H), 7.19 (d, 2H). m/z (ESI) 308.

2-(4-{4-[N'-(3,5-Diamino-6-chloropyrazine-2-carbonyl)guanidino]butyl}phenoxy)-N-(3-dimethylaminopropyl)acetamide (6)

1-(3,5-Diamino-6-chloropyrazine-2-carbony)-2-methylisothiourea hydriodide (292 mg, 0.75 mmol) 5 was added to a solution of compound 4 (200 mg, 0.65 mmol), DIPEA (0.39 mL, 2.25 mmol), and ethanol (5 mL). The reaction mixture was stirred at 65° C. for 3 h. The solvent was removed under reduced pressure and the residue was purified by preparative TLC (80:18:2 dichloromethane/methanol/concentrated ammonium hydroxide, v/v) to provide 6 (190 mg, 56%) as a light yellow solid. $^1$H NMR (300 MHz, CD$_3$OD) δ 1.65 (m, 6H), 2.15 (s, 6H), 2.32 (m, 2H), 2.64 (m, 2H), 3.27 (m, 8H), 4.49 (s, 2H), 6.89 (d, 2H), 7.15 (d, 2H). m/z (ESI) 520.

Methanesulfonic acid (67.2 mg, 0.70 mmol) was added to the solution of 6 (182 mg, 0.35 mmol) in ethanol (4 mL). The resulting solution was stirred at room temperature for 0.5 h; then the solvent was completely evaporated, affording 212 mg (85%) of 7 as a light yellow solid. m.p. 187-190° C. $^1$H NMR (300 MHz, CD$_3$OD) δ 1.65 (m, 4H), 1.90 (m, 2H), 2.67 (m, 8H), 2.85 (s, 6H), 3.15 (m, 2H), 3.40 (m, 4H), 4.49 (s, 2H), 6.89 (d, 2H), 7.15 (d, 2H). m/z (APCI) 520 [C$_{23}$H$_{34}$ClN$_9$O$_3$+H]$^+$.

Scheme 1:
Synthesis of PSA 24304

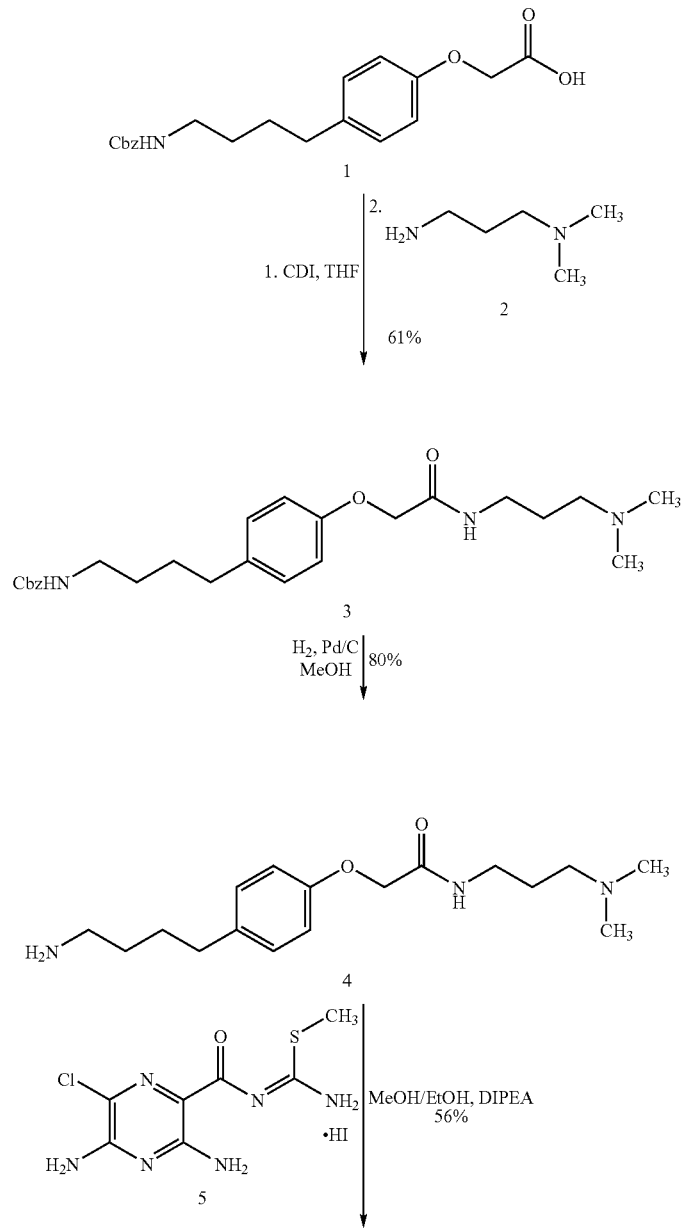

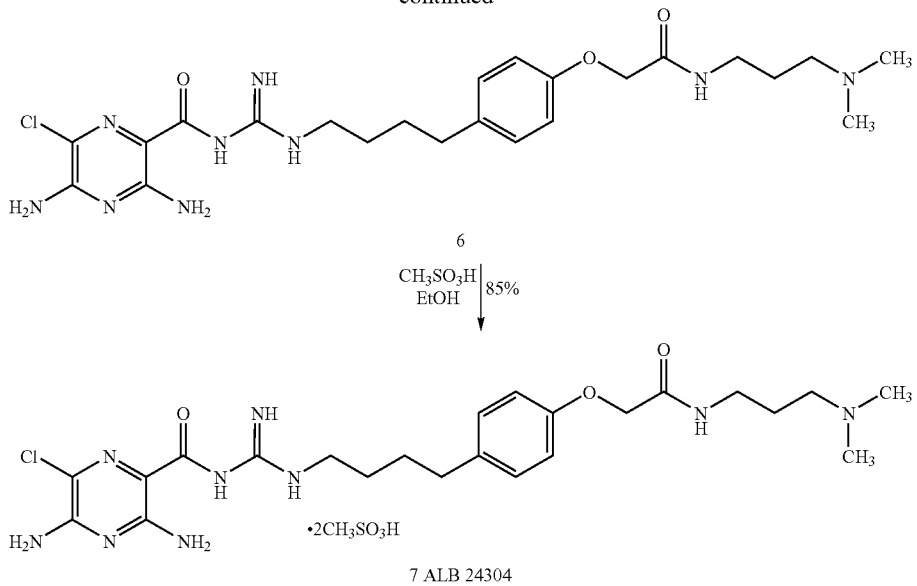

7 ALB 24304

Example 2

Synthesis and Physical Properties of Selected Soluble Amides

Utilizing the procedures exemplified in Example 1 and Scheme 1, the compounds listed in Table 1 were prepared.

TABLE 1

Physical Properties of Selected Amides

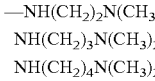

| PSAI # | R | Molecular Formula 2CH$_3$SO$_3$H | Molecular Weight | Melting Point °C. | NMR[1] | HPLC[2] Analysis (%) | MZ[3] |
|---|---|---|---|---|---|---|---|
| 23778 | —NH(CH$_2$)$_2$NH2 | C$_{20}$H$_{28}$ClN$_9$O$_3$ | 670.16 | 105-107° (d) | Consistent | 95.4 | 478 |
| 23185a | —NH(CH$_2$)$_2$N(CH$_3$)$_2$ | C22H32ClN$_9$O$_3$ | 698.22 | 97-99° | Consistent | 97.4 | 506 |
| 24304 | NH(CH$_2$)$_3$N(CH$_3$)$_2$ | C$_{23}$H$_{34}$ClN$_9$O$_3$ | 712.25 | 187-190° | Consistent | 95.8 | 520 |
| 24305 | NH(CH$_2$)$_4$N(CH$_3$)$_2$ | C$_{24}$H$_{36}$ClN$_9$O$_3$ | 726.27 | 188-190° | Consistent | 97.0 | 534 |
| 23450 | NH(CH$_2$)$_2$N(CH$_2$CH$_2$OH)$_2$ | C$_{24}$H$_{36}$ClN$_9$O$_5$ | 758.27 | 87-89° | Consistent | 97.7 | 566 |
| 19913 | —N⟨piperazine⟩NH | C$_{22}$H$_{30}$ClN$_9$O$_3$ | 696.21 | 72-74° | Consistent | 97.9 | 504 |

Notes:
[1] NMR = 500 MHz $^1$H NMR Spectrum (CD$_3$OD).
[2] HPLC—Polarity dC18 Column, Detector @ 200 nM.
[3] M/Z = APCI Mass Spectrum [Free Base + H]$^+$.

Example 3

Solubility of Selected Amides

Table 2 gives the solubility in saline of selected amide bis methane sulfonic acid salts and compares them to the mono addition methane sulfonic acid salt of PSA 9714.

TABLE 2

Solubility of Selected Amides

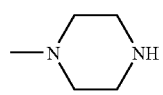

| PSA# | R | $S^1$ | $S^2$ |
|---|---|---|---|
| 9714 | —NH$_2$ | <0.1 mg/ml | <0.1 mg/ml |
| 237778 | —NH(CH$_2$)$_2$NH$_2$ | >5 mg/ml | |
| 23185a | —NH(CH$_2$)$_2$N(CH$_3$)$_2$ | >5 mg/ml | |
| 24304 | —NH(CH$_2$)$_3$N(CH$_3$)$_2$ | >5 mg/ml | |
| 24305 | —NH(CH$_2$)$_4$N(CH$_3$)$_2$ | >5 mg/ml | >5 mg/ml |
| 23450 | NH(CH$_2$)$_2$N(CH$_2$CH$_2$OH)$_2$ | >5 mg/ml | >5 mg/ml |
| 19913 | (piperazinyl) | >5 mg/ml | |

$S^1$ = Solubility in 0.12% NaCl Solution
$S^2$ = Solubility in 0.9% NaCl Solution (normal Saline)

Example 4

Sodium Channel Blocking Activity of Selected Soluble Amides

Utilizing the tests set forth above, Table 3 summaries the ENaC blocking ability of some of the amides of this invention when assayed in canine bronchial epithelium.

TABLE 3

Epithelial Sodium Channel Blocking Activity of Selected Amides

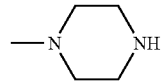

| PSA# | R | IC$_{50}$ (nM) | Fold Amiloride** (PSA4022 = 100) |
|---|---|---|---|
| 9714 | —NH$_2$ | 15.2 + 6.3 (n = 36) | 62 |
| 237778 | —NH(CH$_2$)$_2$NH$_2$ | 5 ± 2 (n = 4) | 146 |
| 23185a | —NH(CH$_2$)$_2$N(CH$_3$)$_2$ | 14 ± 9 (n = 3) | 59 |
| 24304 | —NH(CH$_2$)$_3$N(CH$_3$)$_2$ | 4 ± 2 (n = 7) | 173 |
| 24305 | —NH(CH$_2$)$_4$N(CH$_3$)$_2$ | 6 ± 5 (n = 6) | 152 |
| 23450 | NH(CH$_2$)$_2$N(CH$_2$CH$_2$OH)$_2$ | 18 | 38 |
| 19913 | (piperazinyl) | 9 ± 1 (n = 2) | 98 |

**Relative potency for PSA4022 = 100 using IC$_{50}$ from PSA4022 in same run.

Example 5

N-(3,5-Diamino-6-chloropyrazine-2-carbonyl)-N'-{4-[4-(piperazine-1-carbonyl)phenyl]butyl}guanidine bis-methanesulfonate (PSA23607)

4-(4-Aminobutyl)benzoic acid (8)

A solution of sodium hydroxide (0.69 g, 17.37 mmol) in water (30 mL) was added to a solution of 24 (1.2 g, 5.79 mmol) in methanol (30 mL) and stirred at room temperature for 48 h. Then the solvent was removed under reduced pressure. Water (20 mL) was added and pH was adjusted to 7 with HCl. The white solid precipitate was filtered off, washed with water and dried in vacuum. The crude product 8 (1.39 g) was obtained as a white solid and used for the next step without further purification.

4-(4-Benzyloxycarbonylaminobutyl)benzoic acid (9)

Sodium hydrogencarbonate (0.95 g, 11.32 mmol) was added into a suspension of 30 in THF (120 mL), followed by water (10 mL), affording a clear solution. Benzyl chloroformate (1.21 mL, 8.49 mmol) was then added into the reaction mixture at 0° C. The reaction mixture was then stirred at room temperature overnight. After that, the solvent was removed under reduced pressure. Ethyl acetate (70 mL) was added to the residue and the solution was washed with 2N HCl (2×30 mL) and water (2×50 mL), then dried in vacuum. 1.82 g (98%) of 9 was obtained as a white solid. $^1$H NMR (300 MHz, DMSO-d$_6$) δ 1.11 (m, 2H), 1.28 (m, 2H), 2.33 (m, 2H), 3.02 (m, 2H), 5.01 (m, 2H), 7.15 (m, 7H), 7.93 (d 2H).

N-(3,5-Diamino-6-chloropyrazine-2-carbonyl)-N'-{4-[4-(piperazine-1-carbonyl)phenyl]butyl}guanidine bis-methanesulfonate (PSA23607)

Compound 9 was converted to PSA236507 utilizing the general methods described in Example 1 yielding the desired product, melting point 122-124° C., 500 MHz $^1$H NMR Spectrum (CD$_3$OD) was consistent with assigned structure, HPLC Analysis 98.5% (area percent), Polarity dC18 Column, Detector (220 nm, ESI mass Spectrum m/z 474 [C$_{21}$H$_{28}$ClN$_9$O$_2$+H]$^+$. PSA23607 had an IC$_{50}$ of 12.5±0.5 nM on canine bronchial epithelial and had a solubility of greater than 5 mg/ml in 0.12% saline solution.

Example 6

3-[4-(4-Aminobutyl)phenoxy]-2-tert-butoxycarbonylaminopropionic acid methyl ester (13)

3-[4-(4-Benzyloxycarbonylaminobutyl)phenoxy]-2-(tritylamino)propionic acid methyl ester (10)

Commercially available N-trityl-L-serine methyl ester (1.60 g, 5.34 mmol) was combined with triphenylphosphine (1.28 g, 4.88 mmol) and [4-(4-hydroxyphenyl)butyl]carbamic acid benzyl ester (2.0 g, 6.68 mmol) in benzene (40 mL) at room temperature. Diisopropyl azodicarboxylate (0.958 mL, 4.86 mmol) was added dropwise and the reaction was stirred for 14 days. The solvent was removed under reduced pressure and the residue was purified by column chromatography (silica gel, eluent: 6:1, v/v dichloromethane/ethyl acetate) to provide compound 10 (2.22 g, 51%). $^1$H NMR (300 MHz, CDCl$_3$) δ 7.52 (m, 6H), 7.39-7.14 (m, 14H), 7.06 (d, 2H), 6.79 (d, 2H), 5.09 (s, 2H), 4.72 (m, 1H), 4.24 (m, 1H), 4.01 (m, 1H), 3.72 (m, 1H), 3.22 (s, 3H), 3.18 (m, 2H), 2.88 (d, 1H), 2.57 (m, 2H), 1.66-1.48 (m, 4H). $R_f$=0.91 (5:1 v/v dichloromethane/ethyl acetate).

3-[4-(4-Benzyloxycarbonylaminobutyl)phenoxy]-2-tert-butoxycarbonylamino-propionic acid methyl ester (12)

Compound 10 (2.22 g, 3.45 mmol) was dissolved in a mixture of dichloromethane/water (25 mL/0.5 mL) then trifluoroacetic acid (0.75 mL, 10.0 mmol) was added and the reaction was stirred for 2 h. The solvent was removed under reduced pressure and the residue was dissolved in dichloromethane (25 mL) and treated with triethylamine (0.72 mL, 5.12 mmol) and di-tert-butyl dicarbonate (0.829 g, 3.79 mmol) for 72 h. Removal of the solvents under reduced pressure followed by column chromatography (silica gel, eluent: 9:1, v/v dichloromethane/ethyl acetate) provided compound 12 (0.90 g, 52%). $^1$H NMR (300 MHz, CDCl$_3$) δ 7.34 (m, 5H), 7.07 (d, 2H), 6.79 (d, 2H), 5.50 (d, 1H), 5.10 (s, 2H), 4.68 (m, 2H), 4.38 (m, 1H), 4.17 (m, 1H), 3.77 (s, 3H), 3.20 (m, 2H), 2.57 (m, 2H), 1.67-1.48 (m, 4H), 1.45 (s, 9H). m/z (APCI) 401 [$C_{27}H_{36}N_2O_7$—Boc+H]$^+$.

3-[4-(4-Aminobutyl)phenoxy]-2-tert-butoxycarbonylaminopropionic acid methyl ester (13)

Compound 12 (505 mg, 1.00 mmol) was dissolved in methanol (20 mL) and 10% palladium on carbon (100 mg) was added. The flask was evacuated, filled with hydrogen gas under balloon pressure and stirred overnight. Filtration through celite to remove the catalyst followed by removal of the solvent under reduced pressure provided compound 13 (366 mg, 98%). $^1$H NMR (300 MHz, CDCl$_3$) δ 7.08 (d, 2H), 6.80 (d, 2H), 5.51 (d, 1H), 4.66 (m, 1H), 4.38 (m, 1H), 4.17 (m, 1H), 3.78 (s, 3H), 2.73 (m, 2H), 2.58 (m, 2H), 1.90 (br s, 2H), 1.62 (m, 2H), 1.50 (m, 2H), 1.48 (s, 9H).

Example 7

3-[4-(4-Aminobutyl)phenoxy]-2-tert-butoxycarbonylaminopropionic acid methyl ester (16)

Scheme 2.
Synthesis of Amino Amide Precursor 16

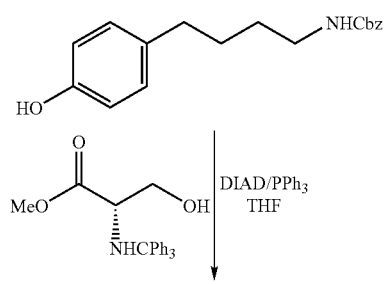

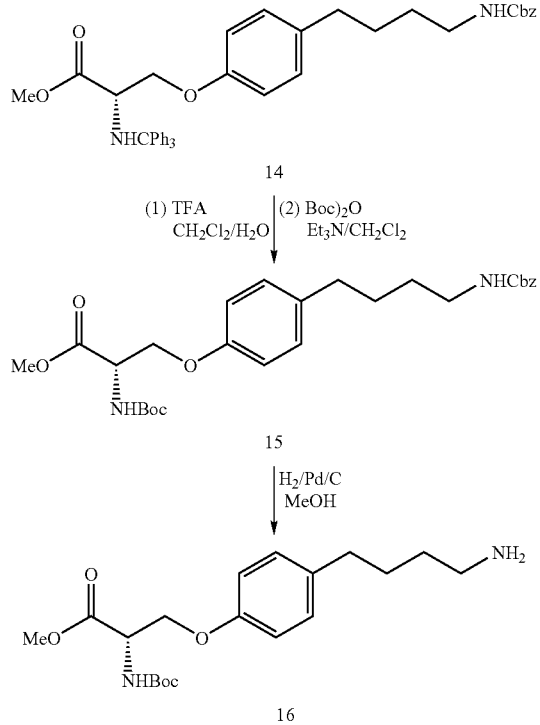

3-[4-(4-Benzyloxycarbonylaminobutyl)phenoxy]-2-(tritylamino)propionic acid methyl ester (14)

Commercially available N-trityl-L-serine methyl ester (1.60 g, 5.34 mmol) was combined with triphenylphosphine (1.28 g, 4.88 mmol) and [4-(4-hydroxyphenyl)butyl]carbamic acid benzyl ester (2.0 g, 6.68 mmol) in benzene (40 mL) at room temperature. Diisopropyl azodicarboxylate (0.958 mL, 4.86 mmol) was added dropwise and the reaction was stirred for 14 days. The solvent was removed under reduced pressure and the residue was purified by column chromatography (silica gel, eluent: δ: 1, v/v dichloromethane/ethyl acetate) to provide compound 141 (2.22 g, 51%). $^1$H NMR (300 MHz, CDCl$_3$) δ 7.52 (m, 6H), 7.39-7.14 (m, 14H), 7.06 (d, 2H), 6.79 (d, 2H), 5.09 (s, 2H), 4.72 (m, 1H), 4.24 (m, 1H), 4.01 (m, 1H), 3.72 (m, 1H), 3.22 (s, 3H), 3.18 (m, 2H), 2.88 (d, 1H), 2.57 (m, 2H), 1.66-1.48 (m, 4H). $R_f$=0.91 (5:1 v/v dichloromethane/ethyl acetate).

3-[4-(4-Benzyloxycarbonylaminobutyl)phenoxy]-2-tert-butoxycarbonylamino-propionic acid methyl ester (15)

Compound 14 (2.22 g, 3.45 mmol) was dissolved in a mixture of dichloromethane/water (25 mL/0.5 mL) then trifluoroacetic acid (0.75 mL, 10.0 mmol) was added and the reaction was stirred for 2 h. The solvent was removed under reduced pressure and the residue was dissolved in dichloromethane (25 mL) and treated with triethylamine (0.72 mL, 5.12 mmol) and di-tert-butyl dicarbonate (0.829 g, 3.79 mmol) for 72 h. Removal of the solvents under reduced pressure followed by column chromatography (silica gel, eluent: 9:1, v/v dichloromethane/ethyl acetate) provided compound 15 (0.90 g, 52%). $^1$H NMR (300 MHz, CDCl$_3$) δ 7.34 (m, 5H), 7.07 (d, 2H), 6.79 (d, 2H), 5.50 (d, 1H), 5.10 (s, 2H), 4.68

(m, 2H), 4.38 (m, 1H), 4.17 (m, 1H), 3.77 (s, 3H), 3.20 (m, 2H), 2.57 (m, 2H), 1.67-1.48 (m, 4H), 1.45 (s, 9H). m/z (APCI) 401 [$C_{27}H_{36}N_2O_7$— Boc+H]$^+$.

3-[4-(4-Aminobutyl)phenoxy]-2-tert-butoxycarbonylaminopropionic acid methyl ester (16)

Compound 15 (505 mg, 1.00 mmol) was dissolved in methanol (20 mL) and 10% palladium on carbon (100 mg) was added. The flask was evacuated, filled with hydrogen gas under balloon pressure and stirred overnight. Filtration through celite to remove the catalyst followed by removal of the solvent under reduced pressure provided compound 16 (366 mg, 98%). $^1$H NMR (300 MHz, CDCl$_3$) δ 7.08 (d, 2H), 6.80 (d, 2H), 5.51 (d, 1H), 4.66 (m, 1H), 4.38 (m, 1H), 4.17 (m, 1H), 3.78 (s, 3H), 2.73 (m, 2H), 2.58 (m, 2H), 1.90 (br s, 2H), 1.62 (m, 2H), 1.50 (m, 2H), 1.48 (s, 9H).

Example 8

{4-[4-(3-tert-Butoxycarbonylamino-3-carbamoylpropoxy)phenyl]butyl}carbamic acid benzyl ester (20)

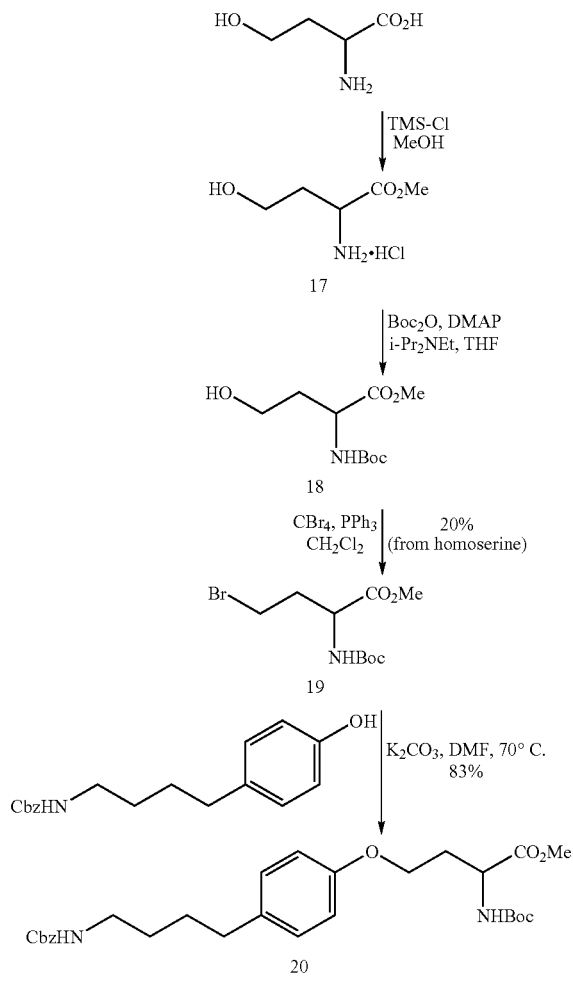

Scheme 3.
Synthesis of Homologus amino amides

2-Amino-4-hydroxybutyric acid methyl ester hydrochloride (17)

A suspension of DL-homoserine (1.00 g, 8.39 mmol) in methanol (40 mL) was placed in an ice bath. Trimethylsilyl chloride (2.34 mL, 18.5 mmol) was added dropwise via syringe. The reaction mixture gradually became homogenous and was further stirred at rt for 14 h, concentrated by rotary evaporation, and further dried under high vacuum. The crude oil thus obtained was used for the next step without further purification. $^1$H NMR (300 MHz, CD$_3$OD) δ 2.00-2.24 (m, 2H), 3.70-3.80 (m, 2H), 3.85 (s, 3H), 4.12-4.22 (m, 1H). m/z (ESI) 134 [$C_5H_{11}NO_3$+H]$^+$.

2-tert-Butoxycarbonylamino-4-hydroxybutyric acid methyl ester (18)

2-Amino-4-hydroxybutyric acid methyl ester hydrochloride (17) was suspended in anhydrous THF (15 mL) and placed in an ice bath. Diisopropylethylamine (2.92 mL, 16.8 mmol) was added via syringe, followed by the addition of DMAP (205 mg, 1.68 mmol) and Boc$_2$O (3.85 g, 17.6 mmol). The mixture was stirred at 0° C. for 10 min and at room temperature for 14 h. Solvent was removed under reduced pressure and residue was taken up by ethyl acetate (100 mL), washed with water (30 mL×2) and brine (40 mL), dried over sodium sulfate, and concentrated. The colorless oil (1.96 g) was used for the next step without further purification. $^1$H NMR (300 MHz, CDCl$_3$) δ 1.45 (s, 9H), 2.05-2.28 (m, 2H), 3.68-3.75 (m, 2H), 3.80 (s, 3H), 4.08-4.15 (m, 1H), 5.30-5.41 (m, 1H). m/z (ESI) 234 [$C_{10}H_{19}NO_5$+H]$^+$.

4-Bromo-2-tert-butoxycarbonylaminobutyric acid methyl ester (19)

A solution of triphenylphosphine (2.20 g, 8.39 mmol) in dry CH$_2$Cl$_2$ (20 mL) was added dropwise via syringe to a solution of N-Boc homoserine methyl ester 18 (8.39 mmol) and carbon tetrabromide (4.18 g, 12.60 mmol) in dry CH$_2$Cl$_2$ (20 mL). The resulting dark solution was stirred at room temperature for 16 h. Hexanes was added and precipitates were removed by suction filtration. The filtrate was concentrated under reduced pressure and subject to flash silica gel column chromatography using ethyl acetate/hexanes (1:10, v/v then 1:6, v/v) to give the desired product 19 as a yellow oil (501 mg, 20% overall yield from homoserine). $^1$H NMR (300 MHz, CDCl$_3$) δ 1.45 (s, 9H), 2.12-2.48 (m, 2H), 3.39-3.47 (m, 2H), 3.78 (s, 3H), 4.33-4.48 (m, 1H), 5.10-5.22 (m, 1H). m/z (ESI) 296 [$C_{10}H_{18}BrNO_4$+H]$^+$.

4-[4-(4-Benzyloxycarbonylaminobutyl)phenoxy]-2-tert-butoxycarbonylamino-butyric acid methyl ester (20)

Potassium carbonate (935 mg, 6.77 mmol) was added in one portion to a solution of 4-[4-(benzyloxycarbonylamino)butyl]phenol (506 mg, 1.69 mmol) and N-Boc bromide 19 (501 mg, 1.69 mmol) in anhydrous DMF (10 mL). The reaction mixture was stirred at 70° C. (oil bath) for 14 h, cooled to room temperature, and diluted with ethyl acetate (100 mL) and hexanes (20 mL). The mixture was washed with water (4×20 mL) and brine (40 mL) and concentrated under reduced pressure. Flash silica gel column chromatography using ethyl acetate/CH$_2$Cl$_2$ (1:25, 1:20, v/v) gave the desired product 20 as a thick yellow oil (718 mg, 83% yield). $^1$H NMR (300 MHz, CDCl$_3$) δ 1.44 (s, 9H), 1.48-1.68 (m, 4H), 2.12-2.38 (m, 2H), 2.48-2.60 (m, 2H), 3.10-3.24 (m, 2H), 3.75 (s, 3H), 3.97-4.06 (m, 2H), 4.41-4.52 (m, 1H), 4.70 (br s, 1H), 5.09 (s, 2H), 5.25-5.37 (m, 1H), 6.70-6.80 (m, 2H), 6.95-7.09 (m, 2H), 7.30-7.38 (m, 5H). m/z (ESI) 515 $[C_{28}H_{38}N_2O_7+H]^+$.

Example 9

3-{2-[4-(4-Benzyloxycarbonylaminobutyl)phenoxy]ethylamino}-2-N,N'-di-(tert-butoxycarbonyl)aminopropionic acid methyl ester (21)

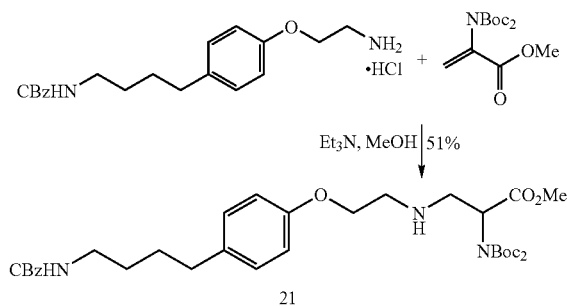

A mixture of {4-[4-(2-aminoethoxy)phenyl]butyl}carbamic acid benzyl ester hydrochloride (141 mg, 0.372 mmol), 2-[N,N'-di(tert-butoxycarbonyl)]aminoacrylic acid methyl ester (102 mg, 0.338 mmol), and triethylamine (0.16 mL, 1.11 mmol) in methanol (3 mL) was stirred at 55° C. (oil bath) for 16 h. It was then cooled to room temperature. The solvent was removed by rotary evaporation. The residue was taken up in ethyl acetate and washed with saturated sodium bicarbonate solution and brine. The organic layer was concentrated in vacuo and purified by flash silica gel column chromatography using ethyl acetate/hexanes (gradient 1:10, 1:6, 1:4, and 1:2, v/v) to give the desired Michael adduct 21 (110 mg, 51% yield). $^1$H NMR (300 MHz, CDCl$_3$) δ 1.42 (s, 9H), 1.43-1.50 (m, 9H), 1.50-1.65 (m, 4H), 2.50-2.60 (m, 2H), 3.12-3.25 (m, 2H), 3.49-3.72 (m, 4H), 3.75 (s, 3H), 3.98-4.10 (m, 2H), 4.45-4.65 (m, 1H), 4.79 (br s, 1H), 5.09 (s, 2H), 5.50 (m, 1H), 6.81 (d, J=8.5 Hz, 2H), 7.06 (d, J=8.5 Hz, 2H), 7.28-7.38 (m, 5H). m/z (ESI) 644 $[C_{34}H_{49}N_3O_9+H]^+$.

Example 10

5-[4-(4-Aminobutyl)phenyl]-2-(R)-tert-butoxycarbonylaminopentynoic acid methyl ester (26)

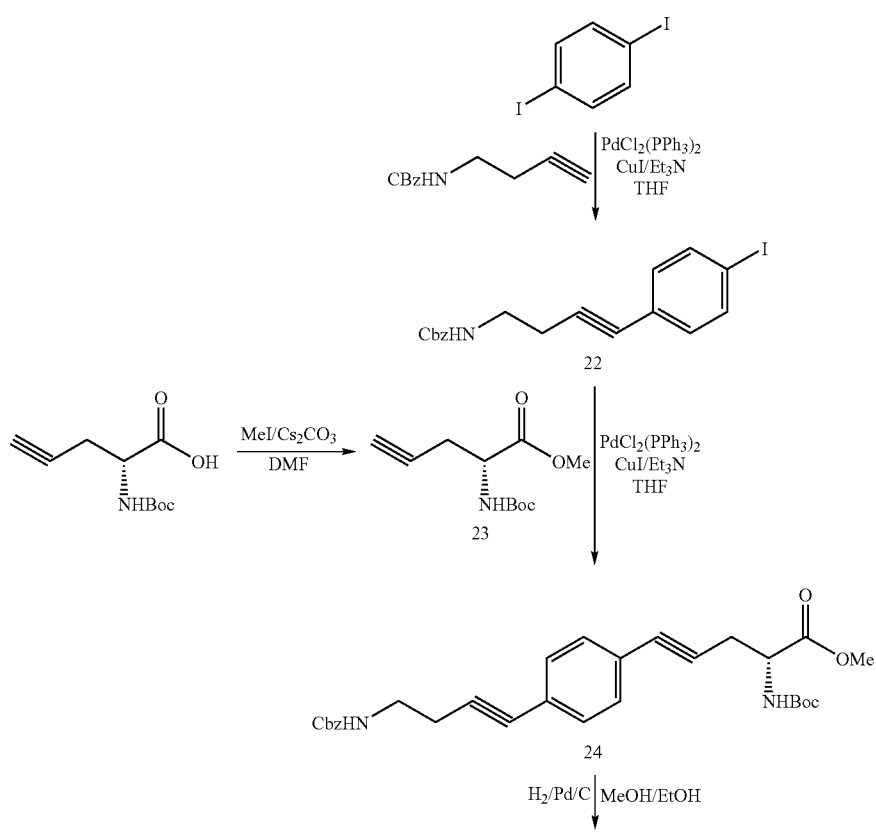

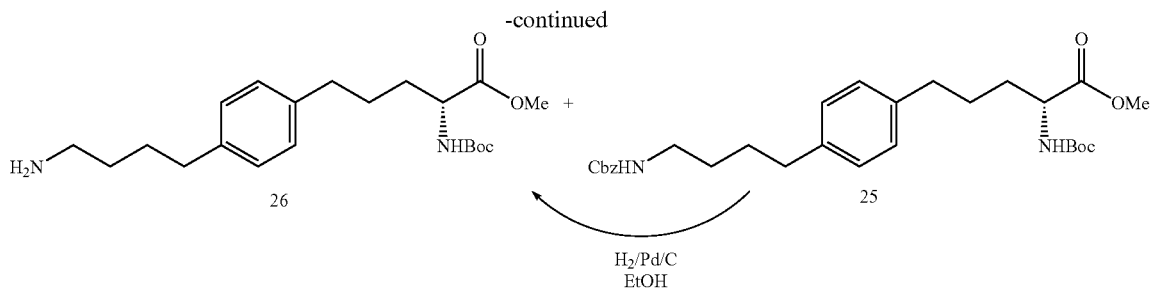

[4-(4-Iodophenyl)but-3-ynyl]carbamic acid benzyl ester (22)

To a mixture of anhydrous THF and triethylamine (24 mL, 2/1, v/v) were sequentially added 1,4-diiodobenzene (2.03 g, 6.15 mmol) and copper (1) iodide (0.094 g, 0.246 mmol). The mixture was stirred at room temperature for 15 min. The flask was then evacuated and re-filled with Argon. The procedure was repeated three more times to ensure no oxygen remained. The catalyst, dichlorobis(triphenylphosphine)palladium(II) (0.173 g, 0.246 mmol) was added into the mixture under Argon protection. The other starting material, but-3-ynylcarbamic acid benzyl ester (0.50 g, 2.46 mmol), dissolved in THF (8 mL) was added dropwise over 6 hours. The newly formed reaction mixture was further stirred at room temperature overnight. The solid in the reaction mixture was vacuum filtered. The filtrate was concentrated. The residue was re-dissolved in dichloromethane and purified by column chromatography, eluting with a mixture of ethyl acetate (0-12%) and hexanes (100-88%) to afford the product 22 (0.852 g, 86%) as an off-white solid. $^1$H NMR (300 MHz, CDCl$_3$): δ 2.61 (t, J=6.4 Hz, 2H), 3.44 (t, J=6.4 Hz, 2H), 5.07 (br s, 1H), 5.12 (s, 2H), 7.10 (d, J=8.3 Hz, 2H), 7.35 (m, 5H), 7.63 (d, J=8.3 Hz, 2H). m/z (APCI) 405 [C$_{18}$H$_{16}$NO$_2$+H]$^+$.

2-(R)-tert-Butoxycarbonylaminopent-4-ynoic acid methyl ester (23)

The commercially available compound, 2-(R)-tert-butoxycarbonylaminopent-4-ynoic acid (0.321 g, 1.50 mmol) was dissolved in anhydrous DMF (5 mL). To the solution was added cesium carbonate (0.54 g, 1.65 mmol) in one portion. The mixture was stirred at room temperature for 45 min before methyl iodide (0.20 mL, 3.00 mmol) was added, and further stirred for three hours. The reaction was quenched with water (10 mL). The organics was extracted with dichloromethane (2×30 mL), washed with water (3×50 mL), and dried over anhydrous sodium sulfate. The solvent was completely removed under vacuum. The residue was further dried under high vacuum over night and used in the next reaction without further purification. The product 23 was obtained as a colorless viscous oil (0.326 g, 95% yield). $^1$H NMR (300 MHz, CDCl$_3$): δ 1.48 (s, 9H), 2.08 (t, J=2.6 Hz, 1H), 2.75 (t, J=6.3 Hz, 2H), 3.78 (s, 3H), 4.46 (m, 1H), 5.32 (br s, 5H).

5-[4-(4-Benzyloxycarbonylaminobut-1-ynyl)phenyl]-2-(R)-tert-butoxycarbonylaminopent-4-ynoic acid methyl ester (24)

Compound 22, [4-(4-iodophenyl)-but-3-ynyl]carbamic acid benzyl ester (0.52 g, 1.283 mmol) was dissolved in a mixture of anhydrous THF and triethylamine (8 mL, 1/1, v/v). To the solution was added copper (I) iodide (0.025 g, 0.128 mmol). The mixture was stirred at room temperature for 15 min. The flask was then evacuated and re-filled with Argon. The procedure was repeated three more times to ensure no oxygen remained. The catalyst, dichlorobis(triphenylphosphine)palladium(II) (0.09 g, 0.128 mmol) was added into the mixture under Argon protection. The mixture was further stirred at room temperature for 30 min. The other starting material 23, 2-tert-butoxycarbonylamino-pent-4-ynoic acid methyl ester (0.32 g, 1.412 mmol), dissolved in THF (4 mL) was added dropwise over 15 min. The newly formed reaction mixture was further stirred overnight at room temperature. The solid in the reaction mixture was vacuum filtered. The filtrate was concentrated. The residue was re-dissolved in dichloromethane and purified by column chromatography, eluting with a mixture of ethyl acetate (0-25%) and hexanes (100-75%) to afford the product 24 (0.64 g, 99%) as a gummy, yellowish solid. $^1$H NMR (300 MHz, CDCl$_3$): δ 1.46 (s, 9H), 2.64 (t, J=6.3 Hz, 2H), 2.95 (t, J=4.1 Hz, 2H), 3.42 (m, 2H), 3.79 (s, 3H), 4.56 (m, 1H), 5.12 (s, 2H), 5.38 (br s, 1H), 7.29 (s, 4H), 7.35 (m, 5H). m/z (APCI) 502 [C$_{29}$H$_{32}$N$_2$O$_6$—H]$^+$.

5-[4-(4-Aminobutyl)phenyl]-2-(R)-tert-butoxycarbonylaminopentynoic acid methyl ester (26)

Compound 24, 5-[4-(4-benzyloxycarbonylaminobut-1-ynyl)phenyl]-2-(R)-tert-butoxycarbonylaminopent-4-ynoic acid methyl ester (0.36 g, 0.713 mmol) was dissolved in a mixture of ethanol and methanol (50 mL, 1/1, v/v) and placed in a Parr shaker bottle. To the solution was added 10% Palladium on carbon (0.20 g, wet) in one portion under Argon protection. The flask was evacuated and re-filled with Argon. The procedure was repeated three more times. The mixture was then stirred at room temperature over night under 35 psi hydrogen atmosphere. The flask was then evacuated and re-filled with nitrogen. The procedure was repeated three times. The catalyst was then filtered under vacuum and washed with ethanol (2×5 mL). The filtrate and washings were combined and concentrated under reduced pressure. The residue was chromatographed over silica gel, eluting with a mixture of methanol (0-12%), ammonium hydroxide (0-1.2%) and dichloromethane (100-86.8%), to afford two products, the desired product 26 (0.045 g, 17%, a colorless, glass-like solid) and its protected form 25 (0.218 m, 60%, a yellowish solid). $^1$H NMR (300 MHz, CD$_3$OD) for compound 26: δ 1.43 (s, 9H), 1.63-1.76 (m, 8H), 2.58-2.64 (m, 4H), 2.79 (t, J=7.0 Hz, 2H), 3.69 (s, 3H), 4.10 (m, 1H), 7.09 (s, 4H). m/z (APCI) for compound 7: 379 [C$_{12}$H$_{34}$N$_2$O$_4$+H]$^+$.

$^1$H NMR (300 MHz, CD$_3$OD) for compound 25: δ 1.42 (s, 9H), 1.61-1.78 (m, 8H), 2.54-2.68 (m, 4H), 2.92 (t, J=7.0 Hz, 2H), 3.14 (t, J=6.9 Hz, 2H), 3.70 (s, 3H), 4.13 (m, 1H), 5.18 (s, 2H), 7.08 (s, 4H), 7.35 (m, 5H).

The compound 25 was resubmitted to hydrogenation to remove the benzyloxycarbonyl protecting group. The procedure was performed as follows: the compound 25 (0.218 g, 0.425 mmol) was dissolved in ethanol (10 mL). The solution was purged with nitrogen both before and after the palladium catalyst (0.10 g, 10% on charcoal, 50% wet) was added, and subjected to hydrogenation for two hours under atmospheric hydrogen. The catalyst was vacuum filtered and washed with ethanol (2×5 mL). The filtrate and washings were combined and concentrated under vacuum. The residue was chromatographed over silica gel, eluting with a mixture of methanol (0-14%), ammonium hydroxide (0-1.4%) and dichloromethane (100-84.6%), to afford the compound 26 (0.131 g, 81%).

Example 11

4-[4-(4-tert-Butoxycarbonylaminobutyl)phenylamino]butyric acid ethyl ester (27)

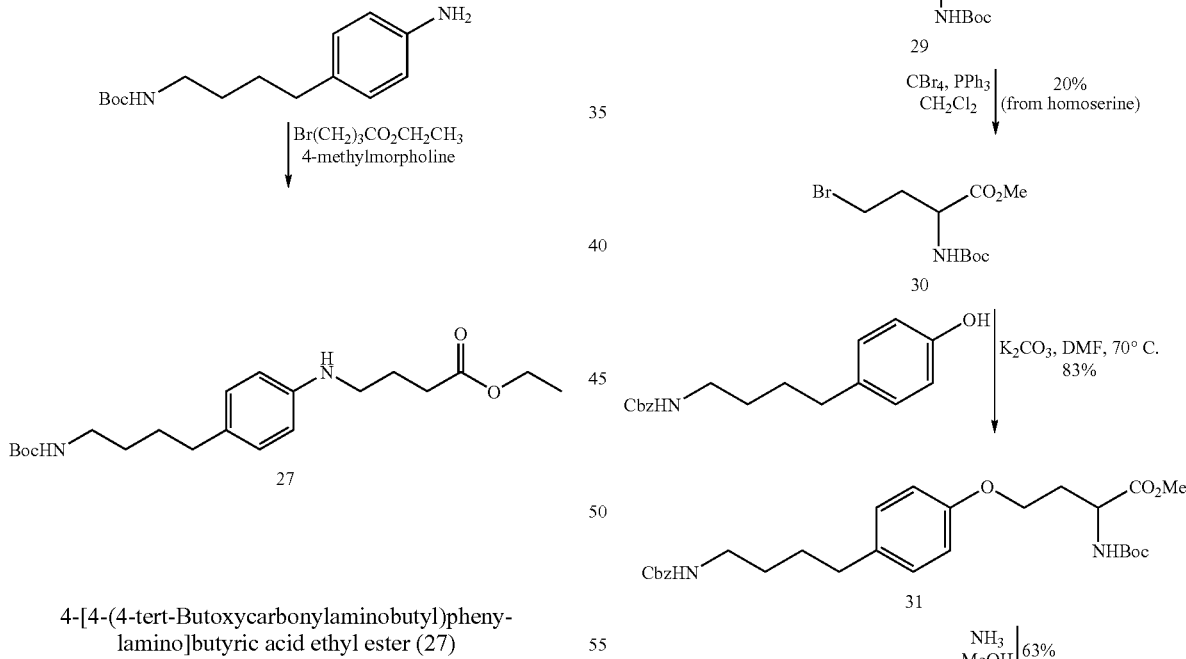

4-[4-(4-tert-Butoxycarbonylaminobutyl)phenylamino]butyric acid ethyl ester (27)

A solution of [4-(4-aminophenyl)butyl]carbamic acid tert-butyl ester (1.7 g, 6.43 mmol), 4-bromo-n-butyric acid ethyl ester (1.88 g, 9.64 mmol), 4-methylmorpholine (1.0 mL, 9.64 mmol), and DMF (10 mL) was stirred at 85° C. for 3 hours under a nitrogen atmosphere. The solvent was evaporated in vacuo. The residue was purified by flash chromatography (silica gel, 4:1, hexanes/ethyl acetate, v/v) to provide 27 (0.44 g, 18%) as a colorless oil. $^1$H NMR (300 MHz, CDCl$_3$) δ 1.23 (t, 3H), 1.47 (s, 9H), 1.55 (m, 4H), 1.96 (m, 2H), 2.43 (t, 2H), 2.51 (t, 2H), 3.19 (m, 4H), 4.14 (q, 2H), 6.54 (d, 2H), 7.00 (d, 2H). m/z (ESI) 379.

Example 12

Synthesis of Amino Amides

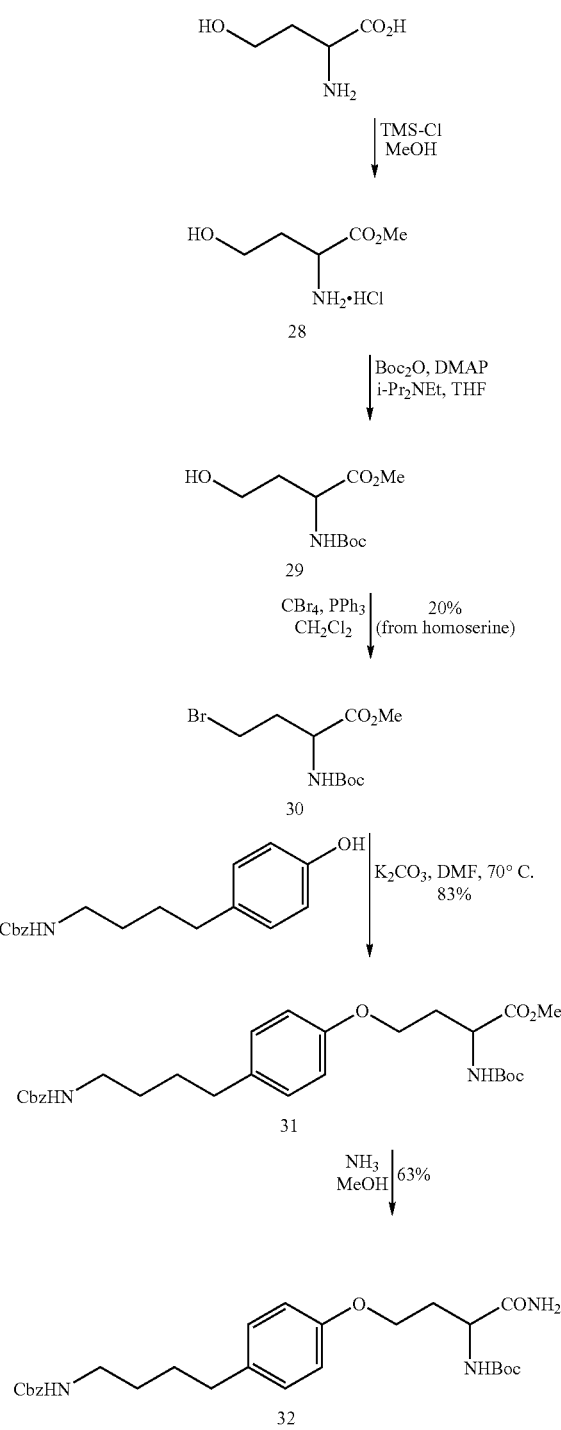

Synthesis of {3-[4-(4-Aminobutyl)phenoxy]-1-carbamoylpropyl}carbamic acid tert-butyl ester (32)

2-Amino-4-hydroxybutyric acid methyl ester hydrochloride (28)

A suspension of DL-homoserine (1.00 g, 8.39 mmol) in methanol (40 mL) was placed in an ice bath. Trimethylsilyl chloride (2.34 mL, 18.5 mmol) was added dropwise via syringe. The reaction mixture gradually became homogenous and was further stirred at rt for 14 h, concentrated by rotary evaporation, and further dried under high vacuum. The crude oil thus obtained was used for the next step without further purification. $^1$H NMR (300 MHz, CD$_3$OD) δ 2.00-2.24 (m, 2H), 3.70-3.80 (m, 2H), 3.85 (s, 3H), 4.12-4.22 (m, 1H). m/z (ESI) 134 [C$_5$H$_{11}$NO$_3$+H]$^+$.

2-tert-Butoxycarbonylamino-4-hydroxybutyric acid methyl ester (29)

2-Amino-4-hydroxybutyric acid methyl ester hydrochloride (28) was suspended in anhydrous THF (15 mL) and placed in an ice bath. Diisopropylethylamine (2.92 mL, 16.8 mmol) was added via syringe, followed by the addition of DMAP (205 mg, 1.68 mmol) and Boc$_2$O (3.85 g, 17.6 mmol). The mixture was stirred at 0° C. for 10 min and at room temperature for 14 h. Solvent was removed under reduced pressure and residue was taken up by ethyl acetate (100 mL), washed with water (30 mL×2) and brine (40 mL), dried over sodium sulfate, and concentrated. The colorless oil (1.96 g) was used for the next step without further purification. $^1$H NMR (300 MHz, CDCl$_3$) δ 1.45 (s, 9H), 2.05-2.28 (m, 2H), 3.68-3.75 (m, 2H), 3.80 (s, 3H), 4.08-4.15 (m, 1H), 5.30-5.41 (m, 1H). m/z (ESI) 234 [C$_{10}$H$_{19}$NO$_5$+H]$^+$.

4-Bromo-2-tert-butoxycarbonylaminobutyric acid methyl ester (30)

A solution of triphenylphosphine (2.20 g, 8.39 mmol) in dry CH$_2$Cl$_2$ (20 mL) was added dropwise via syringe to a solution of N-Boc homoserine methyl ester 29 (8.39 mmol) and carbon tetrabromide (4.18 g, 12.60 mmol) in dry CH$_2$Cl$_2$ (20 mL). The resulting dark solution was stirred at room temperature for 16 h. Hexanes was added and precipitates were removed by suction filtration. The filtrate was concentrated under reduced pressure and subject to flash silica gel column chromatography using ethyl acetate/hexanes (1:10, v/v then 1:6, v/v) to give the desired product 30 as a yellow oil (501 mg, 20% overall yield from homoserine). $^1$H NMR (300 MHz, CDCl$_3$) δ 1.45 (s, 9H), 2.12-2.48 (m, 2H), 3.39-3.47 (m, 2H), 3.78 (s, 3H), 4.33-4.48 (m, 1H), 5.10-5.22 (m, 1H). m/z (ESI) 296 [C$_{10}$H$_{18}$BrNO$_4$+H]$^+$.

4-[4-(4-Benzyloxycarbonylaminobutyl)phenoxy]-2-tert-butoxycarbonylamino-butyric acid methyl ester (31)

Potassium carbonate (935 mg, 6.77 mmol) was added in one portion to a solution of 4-[4-(benzyloxycarbonylamino)butyl]phenol (506 mg, 1.69 mmol) and N-Boc bromide 30 (501 mg, 1.69 mmol) in anhydrous DMF (10 mL). The reaction mixture was stirred at 70° C. (oil bath) for 14 h, cooled to room temperature, and diluted with ethyl acetate (100 mL) and hexanes (20 mL). The mixture was washed with water (4×20 mL) and brine (40 mL) and concentrated under reduced pressure. Flash silica gel column chromatography using ethyl acetate/CH$_2$Cl$_2$ (1:25, 1:20, v/v) gave the desired product 31 as a thick yellow oil (718 mg, 83% yield). $^1$H NMR (300 MHz, CDCl$_3$) δ 1.44 (s, 9H), 1.48-1.68 (m, 4H), 2.12-2.38 (m, 2H), 2.48-2.60 (m, 2H), 3.10-3.24 (m, 2H), 3.75 (s, 3H), 3.97-4.06 (m, 2H), 4.41-4.52 (m, 1H), 4.70 (br s, 1H), 5.09 (s, 2H), 5.25-5.37 (m, 1H), 6.70-6.80 (m, 2H), 6.95-7.09 (m, 2H), 7.30-7.38 (m, 5H). m/z (ESI) 515 [C$_{28}$H$_{38}$N$_2$O$_7$+H]$^+$.

{4-[4-(3-tert-Butoxycarbonylamino-3-carbamoylpropoxy)phenyl]butyl}carbamic acid benzyl ester (32)

Ammonia (7 M in methanol, 20 mL) was added to a solution of N-Boc methyl ester 31 (718 mg, 1.40 mmol) in methanol (5 mL) and the mixture was stirred at room temperature in a sealed tube for 40 h. The mixture was concentrated by rotary evaporation and purified by flash silica gel column chromatography using methanol/dichloromethane (1:30, 1:20, v/v) to give the desired amide 32 as a white solid (436 mg, 63% yield). $^1$H NMR (300 MHz, CDCl$_3$) δ 1.45 (s, 9H), 1.48-1.68 (m, 4H), 2.09-2.32 (m, 2H), 2.48-2.61 (m, 2H), 3.08-3.25 (m, 2H), 3.97-4.20 (m, 2H), 4.30-4.45 (m, 1H), 4.75 (br s, 1H), 5.09 (s, 2H), 5.48-5.58 (m, 1H), 5.62 (br s, 1H), 6.38 (br s, 1H), 6.75-6.85 (m, 2H), 6.99-7.10 (m, 2H), 7.28-7.40 (m, 5H). m/z (ESI) 500 [C$_{27}$H$_{37}$N$_3$O$_6$+H]$^+$.

Example 13

[4-(4-Benzyloxycarbonylaminobutyl)phenoxy]acetic acid ethyl ester (33)

Scheme 8.
Synthesis of 33

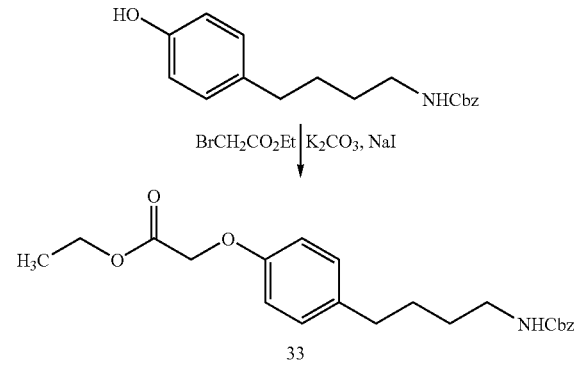

Synthesis of [4-(4-Benzyloxycarbonylaminobutyl)phenoxy]acetic acid ethyl ester (33)

A solution of [4-(4-hydroxyphenyl)butyl]carbamic acid benzyl ester (2.0 g, 6.7 mmol), potassium carbonate (1.0 g, 7.3 mmol), sodium iodide (0.4 g, 2.7 mmol), and DMF (10 mL) was stirred for 30 minutes. A solution of ethyl bromoacetate (0.8 mL, 7.4 mmol) in DMF (10 mL) was added dropwise to the reaction. The reaction was further stirred at room temperature for 3 days, and then poured into water (200 mL). The product was extracted with ethyl acetate. The organic layer was dried over sodium sulfate and concentrated in vacuo. The residue was purified by flash chromatography (silica gel, 1:5 ethyl acetate/hexanes, v/v) to provide the desired product 33 (2.3 g, 89%) as a white solid. $^1$H NMR (300 MHz, CDCl$_3$) δ 1.34 (t, 3H), 1.57 (m, 4H), 2.56 (t, 2H), 3.20 (q, 2H), 4.25 (q, 2H), 4.59 (s, 2H), 5.10 (s, 2H), 6.85 (d, 2H), 7.06 (d, 2H), 7.38 (m, 5H).

Example 14

Synthesis of Thia Amides

Scheme 9.
Synthesis of Thia Amide Precursors

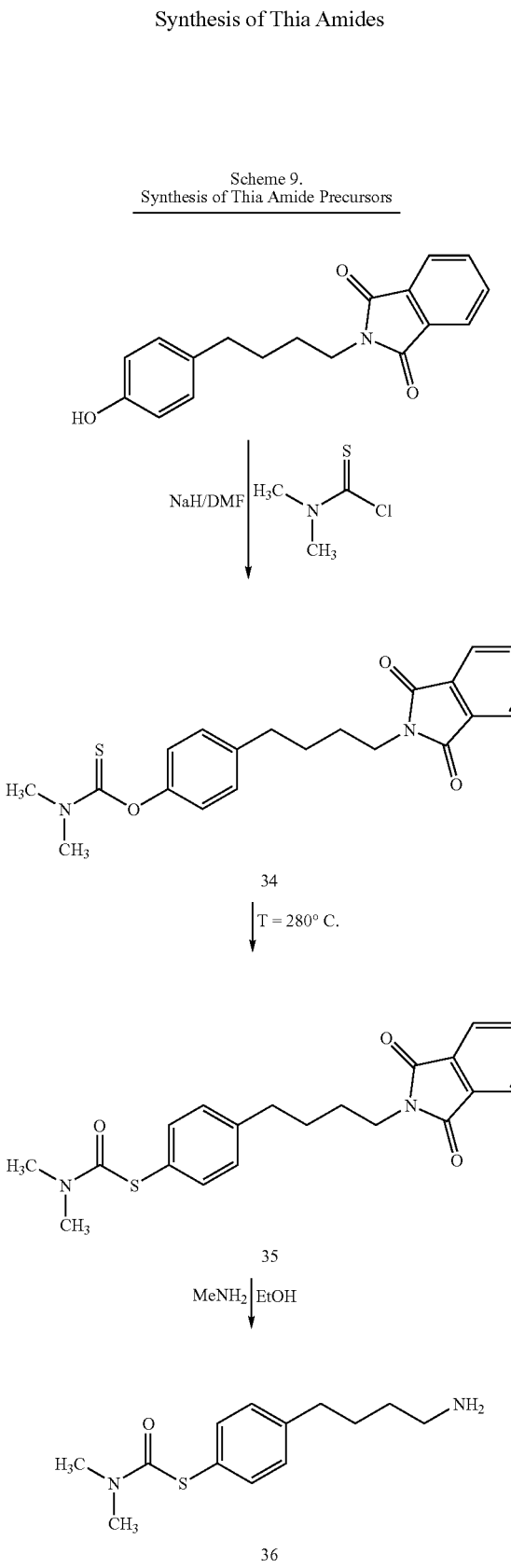

Scheme 14.
Synthesis of Thia Amides

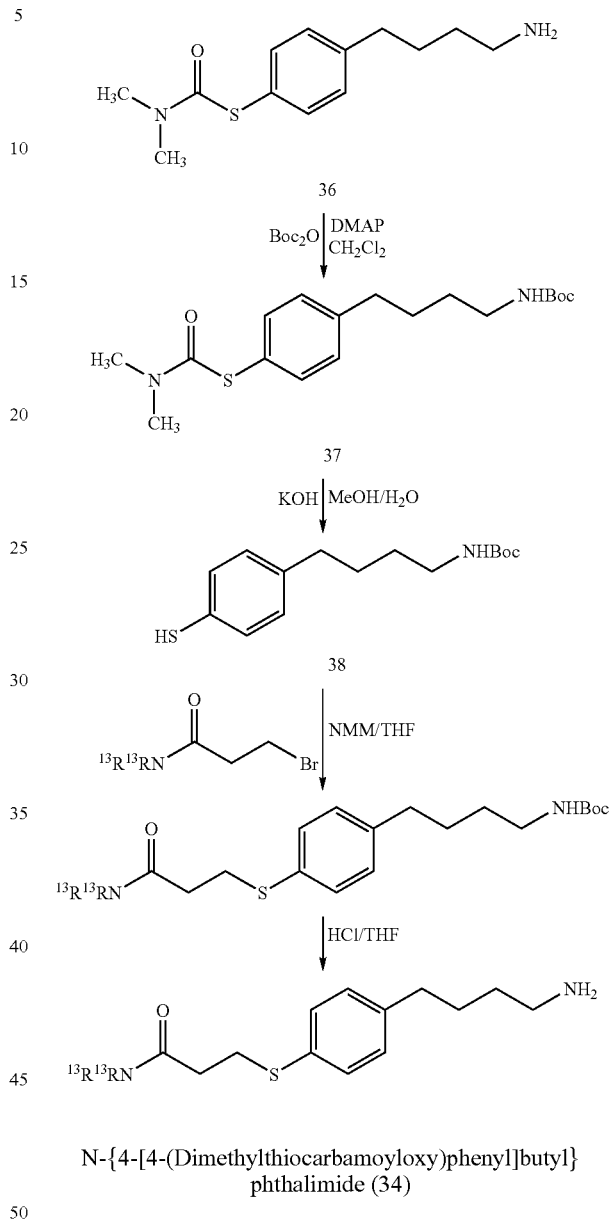

N-{4-[4-(Dimethylthiocarbamoyloxy)phenyl]butyl} phthalimide (34)

A suspension of sodium hydride in mineral oil (0.44 g of 60%) in anhydrous DMF (10 mL) was cooled to 0° C. N-[4-(4-hydroxyphenyl)butyl]phthalimide (2.95 g, 10 mmol) dissolved in dry DMF (15 ml) was added into the mixture which was then stirred for 30 min at 0° C. and allowed to warm to room temperature over 1 h. To the mixture was added portionwise N,N-dimethylthiocarbamoyl chloride (1.35 g, 11 mmol) dissolved in DMF (10 ml). The newly formed mixture was stirred at room temperature overnight, then at 50° C. for 1 h, and was cooled back to room temperature, at which point methanol (10 mL) was added into the mixture. The solvent was removed under reduced pressure. The residue was purified by flash chromatography over silica gel (dichloromethane/hexane/ethyl acetate, 10:1:0.2, v/v) to give N-{4-[4-(dimethylthiocarbamoyloxy)phenyl]butyl}phthalimide 34 (2.27 g, 59%) as a slightly yellow solid. $^1$H NMR (300 MHz, CDCl$_3$) δ 1.72 (m, 4H), 2.66 (m, 2H), 3.33 (s, 3H), 3.45

(s, 3H), 3.70 (m, 2H), 6.96 (d, 2H), 7.18 (d, 2H), 7.71 (m, 2H), 7.84 (m, 2H). m/z (ESI) 383 [$C_{21}H_{22}N_2O_3S+H$]+.

N-{4-[4-(Dimethylcarbamoylthio)phenyl]butyl}phthalimide (35)

N-{4{4-[(Dimethylhiocarbamoyloxy)phenyl]butyl}phthalimide 34

(2.1 g, 5.4 mmol) was placed in preheated sand bath at 230° C. The temperature was raised to 280° C. and the melted compound was kept at this temperature for 2 h in argon atmosphere. The mixture was cooled and the residue was purified by flash chromatography over silica gel (dichloromethane/hexane/ethyl acetate, 10:1:0.2, v/v) to give 35 (1.2 g, 57%) as a white powder. $^1$H NMR (300 MHz, CDCl$_3$) δ 1.70 (m, 4H), 2.66 (t, 2H), 3.05 (br s, 3H), 3.71 (t, 2H), 6.96 (d, 2H), 7.19 (d, 2H), 7.38 (d, 2H), 7.70 (m, 2H), 7.83 (m, 2H). m/z (ESI) 383 [$C_{21}H_{22}N_2O_3S+H$]+.

{4-[4-(Dimethylcarbamoylthio)phenyl]butylamine (36)

Phthalimide 35 (1.1 g, 2.8 mmol) was dissolved in a solution containing 6.6% methylamine in ethanol (100 mL) and allowed to stir at room temperature overnight. The solvent was removed under reduced pressure and the residue was purified by flash chromatotography (silica gel, chloroform/methanol/ammonium hydroxide, 10:1:0.1, v/v) to afford the free amine 36 (0.31 g, 42%) as a white powder. $^1$H NMR (300 MHz, CD$_3$OD) δ 1.51 (m, 2H), 1.65 (m, 2H), 2.66 (m, 4H), 3.02 (m, 6H), 7.23 (d, 2H), 7.35 (d, 2H).

N-tert-Butoxycarbonyl-4-[4-(dimethylcarbamoylthio)phenyl]butylamine (37)

Di-tert-butyldicarbonate (0.35 g, 1.6 mmol) was added to a solution of 36 (0.31 g, 1.22 mmol), 4-Dimethylaminopyridine (DMAP), and dichloromethane (50 mL). The mixture was stirred at room temperature for 26 h. The solvent was removed under reduced pressure and the residue was purified by flash chromatography over silica gel (hexane/ethyl acetate, 3:1, v/v) to give 36 (0.36 g, 83%) as a white powder. $^1$H NMR (300 MHz, CDCl$_3$) δ 1.44 (s, 9H), 1.51 (m, 2H) 1.64 (m, 2H), 3.08 (m, 8H), 4.48 (br s, 1H), 7.18 (d, 2H), 7.39 (d, 2H).

N-[4-(4-Mercaptophenyl)butyl]carbamic acid tert-butyl ester (38)

N-tert-Butoxycarbonyl-4-[4-(dimethylcarbamoylthio)phenyl]butylamine 37 (0.35 g, 1.02 mmol) was dissolved in MeOH (8 mL). KOH (0.19 g, 3.4 mmol) dissolved in water (2 ml) was added. The mixture was stirred under reflux for 6 h and cooled to room temperature. The solvent was removed under reduced pressure. The residue was dissolved in water and acidified with 5% aqueous HCl to pH ~5. The solvent was removed again under reduced pressure and the residue was purified by flash chromatography over silica gel (hexane/ethyl acetate, 3:1, v/v) to give the desired thiophenol 38 (0.13 g, 45%) as a clear oil. $^1$H NMR (300 MHz, CDCl$_3$) δ 1.43 (s, 9H), 1.49 (m, 2H) 1.59 (m, 2H), 2.57 (t, 2H), 3.12 (m, 2H), 3.38 (s, 1H), 4.47 (br s, 1H), 7.04 (d, 2H), 7.19 (d, 2H).

Example 15

4-(4-Carboxymethylphenyl)butylamine (41)

Methanesulfonic acid 4-(4-carboxymethylphenyl)butyl ester (39)

Compound 39 was prepared according to the published procedure. $^1$H NMR (300 MHz, CDCl$_3$) δ 1.75 (m, 4H), 2.78 (m, 2H), 3.12 (s, 3H), 3.88 (s, 3H), 4.22 (m, 2H), 7.28 (d, 2H), 7.98 (d, 2H)

4-(4-Carboxymethylphenyl)butylazide (7). Typical procedure C

Compound 39 (6 g, 0.02 mol) was dissolved in 80 ml of dry DMF then sodium azide (1.8 g, 0.027 mol) was added. The suspension was stirred at 80° C. (oil bath) for 3 h. The solvent was then removed at reduced pressure and the residual oil was treated with CH$_2$Cl$_2$ (100 mL). The resulting solution was washed with water (2×100 mL), brine and dried over magnesium sulfate. The solvent was removed under reduced pressure then the residue was redissolved in a 1:1 mixture of ethyl acetate/hexanes (200 mL) and passed through a pad of silica gel. The solvent was removed under reduced pressure to give 4.1 g (85%) of 7 as clear oil. $^1$H NMR (300 MHz, CDCl$_3$) δ 1.68 (m, 4H), 2.22 (t, 2H), 3.29 (t, 3H), 3.92 (s, 3H), 7.28 (d, 2H), 7.98 (d, 2H).

4-(4-Carboxymethylphenyl)butylamine (41)

Azide 40 (1.7 g, 7.2 mmol) and triphenylphosphine (1.9 g, 7.2 mmol) were dissolved in a 10% solution of water in THF (66 mL) and stirred overnight at 25° C. Then more triphenylphosphine (0.8 g, 3 mmol) was added and the heating was continued at 60° C. (oil bath) for 6 h. The solvent was removed under reduced pressure and the residue was treated with 2M HCl (100 mL) and extracted with ethyl acetate (2×50 mL). The water fraction was collected and ammonium hydroxide was added until the pH reached approximately 13. The mixture was extracted with ethyl acetate (2×100 mL) then the organic fraction was washed with brine, water and dried with sodium sulfate. Ethyl acetate was removed under reduced pressure to give 0.8 g (53%) of amine 41.

Example 16

Synthesis of [4-(4-Aminobutyl)phenoxy]acetic acid ethyl ester (43)

[4-(4-Benzyloxycarbonylaminobutyl)phenoxy]acetic acid ethyl ester (42)

Sodium hydride (60% dispersion in mineral oil) (0.24 g, 10.05 mmol) was added to a cold (0° C.) solution of 4-(4-hydroxyphenyl)butylamine (2 g, 6.68 mmol) in THF (150 mL) under nitrogen atmosphere. The reaction mixture was allowed to warm up to room temperature over 0.5 h with stirring, then ethyl bromoacetate (0.96 mL, 8.02 mmol) and tetrabutylammonium iodide (0.25 g, 0.67 mmol) was sequentially added. The reaction was further stirred at room temperature overnight. Silica gel (25 mL) was added into the mixture and the solvent was evaporated. The impregnated silica gel was subjected to column chromatography purification (silica gel, 5:1 hexanes/ethyl acetate). 2.42 g (94%) of 42 was obtained as a white solid. I H NMR (300 MHz, CDCl$_3$) δ 1.30 (t, 3H), 1.57 (m, 4H), 2.58 (m, 2H), 3.20 (m, 2H), 4.28 (m, 2H), 4.58 (s, 2H), 4.74 (br s, 1H), 5.10 (br s, 2H), 6.82 (m, 2H), 7.08 (m, 2H), 7.38 (br s, 5H).

[4-(4-Aminobutyl)phenoxy]acetic acid ethyl ester (43)

A suspension of 42 (1.11 g, 2.88 mmol) and 10% palladium on carbon (0.40 g, wet) in methanol (50 mL) was stirred at room temperature for 2 h under atmospheric pressure of hydrogen. The mixture was then filtered through a silica gel pad. The solvent was evaporated to provide 43 (0.64 g, 88%) as a white solid. $^1$H NMR (300 MHz, DMSO-d$_6$) δ 1.21 (m, 3H), 1.30-1.63 (m, 6H), 3.13 (m, 2H), 4.17 (m, 2H), 4.72 (br s, 2H), 6.84 (m, 2H), 7.10 (m, 2H).

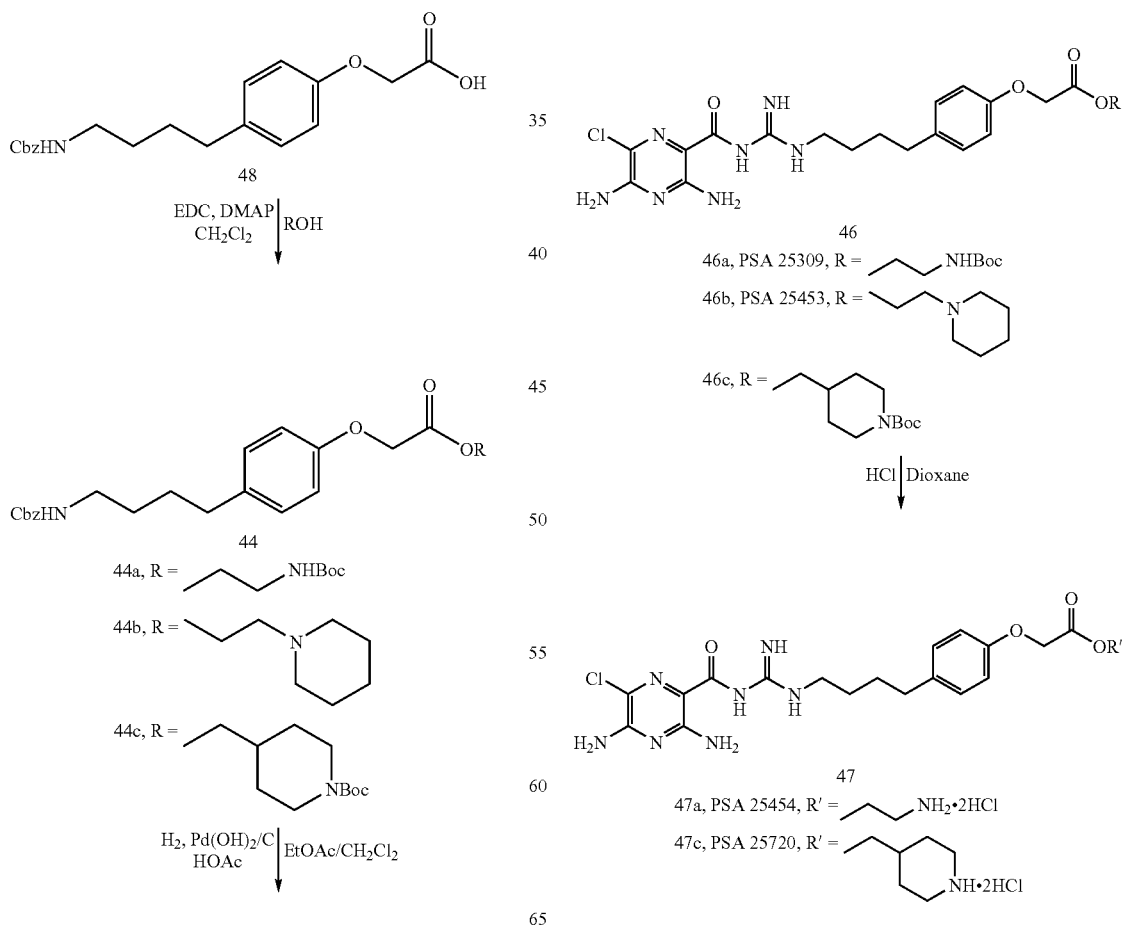

Example 17

Synthesis of (4-{4-[N'-(3,5-diamino-6-chloropyrazine-2-carbonyl)guanidino]butyl}-phenoxy)acetic acid 2-aminoethyl ester dihydrochloride (PSA 25454)

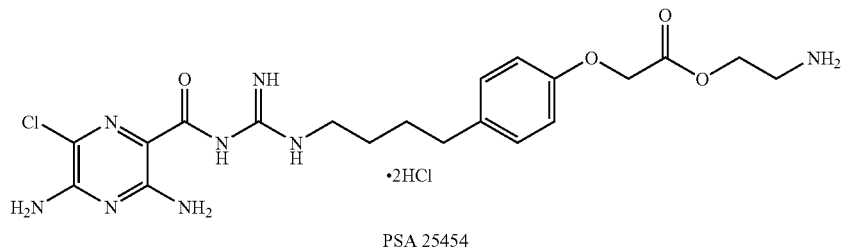

PSA 25454

[4-(4-Benzyloxycarbonylaminobutyl)phenoxy]acetic acid 2-tert-butoxycarbonylamino-ethyl ester (44a)

[4-(4-Benzyloxycarbonylaminobutyl)phenoxy]acetic acid 48 (240 mg, 0.67 mmol) was dissolved in anhydrous CH$_2$Cl$_2$ (6 mL). To the solution was added DMAP (98 mg, 0.80 mmol), followed by EDC-HCl (154 mg, 0.81 mmol). The reaction mixture was stirred at room temperature for 15 min. (2-Hydroxyethyl)carbamic acid tert-butyl ester (0.21 mL, 1.34 mmol) was then added and the stirring was continued for 16 h. Solvent was removed by rotary evaporation. The residue was subjected to flash silica gel column chromatography eluting with ethyl acetate/dichloromethane (1:20, 1:15, and 1:10, v/v) to give the desired ester 44a as a colorless oil (162 mg, 48% yield). $^1$H NMR (300 MHz, CDCl$_3$) δ 1.35-1.65 (m, 4H), 1.44 (s, 9H), 2.45-2.58 (m, 2H), 3.10-3.22 (m, 2H), 3.25-3.42 (m, 2H), 4.18-4.28 (m, 2H), 4.62 (s, 2H), 4.70 (br s, 1H), 4.84 (br s, 1H), 5.08 (s, 2H), 6.81 (d, 2H), 7.07 (d, 2H), 7.25-7.38 (m, 5H). m/z (ESI) 501 [C$_{27}$H$_{36}$N$_2$O$_7$+H]$^+$.

[4-(4-Aminobutyl)phenoxy]acetic acid 2-tert-butoxycarbonylaminoethyl ester ethyl acetate (45a)

A solution of [4-(4-benzyloxycarbonylaminobutyl)phenoxy]acetic acid 2-tert-butoxycarbonylaminoethyl ester 44a (162 mg, 0.32 mmol) and acetic acid (3 drops) in ethyl acetate (3 mL) and dichloromethane (6 mL) was stirred at room temperature for 16 h under hydrogen atmosphere in the presence of palladium hydroxide on activated charcoal (80 mg, 60% wet). The catalyst was removed by suction filtration and the liquid filtrate was concentrated in vacuo to give [4-(4-aminobutyl)phenoxy]acetic acid 2-tert-butoxycarbonylaminoethyl ester ethyl acetate 45a as an off-white solid (100 mg, 84% yield) which was used directly without purification. m/z (ESI) 367 [C$_{19}$H$_{30}$N$_2$O$_5$+H]$^+$.

(4-{4-[N'-(3,5-Diamino-6-chloropyrazine-2-carbonyl)guanidino]butyl}phenoxy)acetic acid 2-tert-butoxycarbonylaminoethyl ester (46a, PSA 25309)

A solution of [4-(4-aminobutyl)phenoxy]acetic acid 2-tert-butoxycarbonylaminoethyl ester ethyl acetate 45a (50 mg, 0.27 mmol) and triethylamine (0.27 mL, 1.53 mmol) in anhydrous THF (4 mL) was stirred at 55° C. (oil bath) for 15 min. To the solution was added 1-(3,5-diamino-6-chloropyrazine-2-carbonyl)-2-methylisothiourea hydriodide (130 mg, 0.34 mmol) in two portions during a period of 15 min. The reaction mixture was stirred at 55° C. for 1 h and cooled to room temperature. The mixture was concentrated by rotary evaporation. The crude residue was purified by flash silica gel column chromatography eluting with dichloromethane/methanol/concentrated ammonium hydroxide (200:10:0, 200:10:1, and 150:10:1, v/v) to give (4-{4-[N'-(3,5-diamino-6-chloropyrazine-2-carbonyl)guanidino]butyl} phenoxy) acetic acid 2-tert-butoxycarbonylaminoethyl ester 46a (PSA 25309) as a yellow solid (60 mg, 76% yield). An analytical pure sample was obtained by semi-preparative HPLC purification (acetonitrile/water). mp 80-82° C. $^1$H NMR (300 MHz, CD$_3$OD) δ 1.45 (s, 9H), 1.60-1.78 (m, 4H), 2.56-2.66 (m, 2H), 3.30-3.38 (m, 4H), 4.15-4.21 (m, 2H), 4.64 (s, 2H), 6.81 (d, 2H), 7.10 (d, 2H). m/z (ESI) 579 [C$_{25}$H$_{35}$ClN$_8$O$_6$+H]$^+$.

(4-{4-[N'-(3,5-Diamino-6-chloropyrazine-2-carbonyl)guanidino]butyl}phenoxy)acetic acid 2-aminoethyl ester dihydrochloride (47a, PSA 25454)

(4-{4-[N'-(3,5-Diamino-6-chloropyrazine-2-carbonyl)guanidino]butyl}phenoxy)acetic acid 2-tert-butoxycarbonylaminoethyl ester 46a (24 mg, 0.041 mmol) was treated with HCl (4 N in dioxane, 1 mL, 4 mmol) at room temperature for 14 h. The reaction mixture was concentrated in vacuo and the residue was purified by semi-preparative HPLC method (acetonitrile/water) to afford the desired product 47a (PSA 25454, 7 mg, 31%) as a yellow solid. mp 66-68° C. $^1$H NMR (500 MHz, CD$_3$OD) δ 1.65-1.76 (m, 4H), 2.60-2.68 (m, 2H), 3.25-3.31 (m, 2H), 3.33-3.39 (m, 2H), 4.40-4.45 (m, 2H), 4.75 (s, 2H), 6.86 (d, 2H), 7.11 (d, 2H). m/z (APCI) 479 [C$_{20}$H$_{27}$ClN$_8$O$_4$$^+$H]$^+$.

Example 18

Synthesis of (4-{4-[N'-(3,5-diamino-6-chloropyrazine-2-carbonyl)guanidino]butyl}-phenoxy)acetic acid 2-piperidin-1-yl-ethyl ester (PSA 25453)

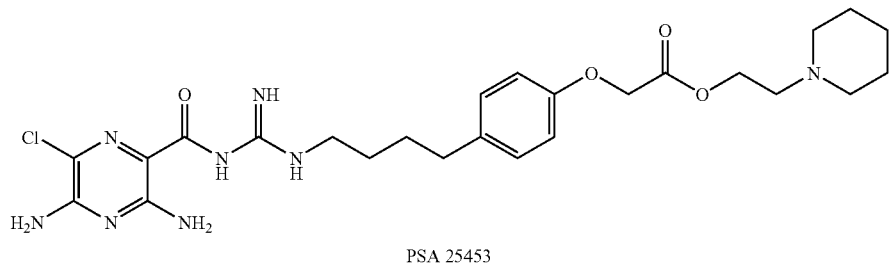

PSA 25453

[4-(4-Benzyloxycarbonylaminobutyl)phenoxy]acetic acid 2-piperidin-1-yl-ethyl ester (44b)

Following the same procedure for the synthesis of compound 44a, compound 49b was synthesized from compound 48 in 60% yield as a colorless oil. $^1$H NMR (300 MHz, CDCl$_3$) δ 1.33-1.68 (m, 10H), 2.30-2.45 (m, 4H), 2.50-2.65 (m, 4H), 3.10-3.25 (m, 2H), 4.28-4.35 (m, 2H), 4.60 (s, 2H), 4.75 (br s, 1H), 5.08 (s, 2H), 6.80 (d, 2H), 7.05 (d, 2H), 7.28-7.38 (m, 5H). m/z (ESI) 469 [C$_{27}$H$_{36}$N$_2$O$_5$+H]$^+$.

[4-(4-Aminobutyl)phenoxy]acetic acid 2-piperidin-1-yl-ethyl ester ethyl acetate (45b)

Following the same procedure for the synthesis of compound 45a, compound 45b was synthesized from compound 44b in 80% yield as an off-white solid, and used directly without purification. m/z (ESI) 335 [C$_{19}$H$_{30}$N$_2$O$_3$+H]$^+$.

(4-{4-[N'-(3,5-Diamino-6-chloropyrazine-2-carbonyl)guanidino]butyl}phenoxy)acetic acid 2-piperidin-1-yl-ethyl ester (46b, PSA 25453)

Following the same procedure for the synthesis of compound 46a, compound 46b was synthesized from compound 45b. One fifth of the crude reaction mixture, after concentration under vacuum, was purified by semi-preparative HPLC method (acetonitrile/water) to afford pure 46b (PSA 25453) as a yellow solid. mp 60-62° C. $^1$H NMR (500 MHz, DMSO-d$_6$) δ 1.30-1.80 (m, 10H), 2.50-2.60 (m, 2H), 2.88-2.98 (m, 2H), 3.25-3.35 (m, 2H), 3.35-3.48 (m, 4H), 4.42-4.48 (m, 2H), 4.78 (s, 2H), 6.88 (d, 2H), 7.12 (d, 2H), 7.42 (s, 2H), 8.75 (s, 1H), 8.90 (s, 1H), 9.15 (s, 1H), 9.65 (s, 1H), 10.45 (s, 1H). m/z (ESI) 547 [C$_{25}$H$_{35}$ClN$_8$O$_4$+H]$^+$.

Example 19

Synthesis of (4-{4-[N'-(3,5-diamino-6-chloropyrazine-2-carbonyl)guanidino]butyl}-phenoxy)acetic acid piperidin-4-yl-methyl ester dihydrochloride (PSA 25720)

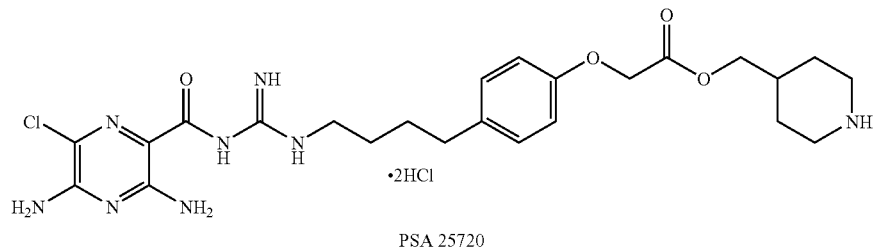

PSA 25720

4-{2-[4-(4-Benzyloxycarbonylaminobutyl)phenoxy]acetoxymethyl}piperidine-1-carboxylic acid tert-butyl ester (44c)

Following the same procedure for the synthesis of compound 44a, compound 44c (a colorless oil) was synthesized in 71% yield by the reaction of compound 48 with 4-hydroxymethylpiperidine-1-carboxylic acid tert-butyl ester, synthesis of which is described below. $^1$H NMR (300 MHz, CDCl$_3$) δ 1.05-1.20 (m, 2H), 1.45 (s, 9H), 1.50-1.65 (m, 6H), 1.70-1.88 (m, 1H), 2.50-2.75 (m, 4H), 3.12-3.26 (m, 2H), 4.00-4.15 (m, 4H), 4.60 (s, 2H), 4.88 (br s, 1H), 5.08 (s, 2H), 6.80 (d, 2H), 7.08 (d, 2H), 7.30-7.48 (m, 5H). m/z (ESI) 555 [C$_{31}$H$_{42}$N$_2$O$_7$+H]$^+$.

Synthesis of 4-hydroxymethylpiperidine-1-carboxylic acid tert-butyl ester

To a solution of piperidin-4-yl-methanol (2.59 g, 22.5 mmol) in 1,4-dioxane (60 mL) was added aqueous sodium hydroxide (1 N, 35 mL). The mixture was chilled in an ice bath. To the chilled mixture was added Boc$_2$O (7.36 g, 33.7 mmol) in one portion. The reaction mixture was stirred at 0° C. for 30 min and at room temperature for 16 h, and concentrated under vacuum to about one-third of its original volume. The remaining mixture was diluted with water and dichloromethane. Layers were separated and the aqueous layer was further extracted with dichloromethane. The combined organics were concentrated under vacuum and purified by flash silica gel column chromatography eluting with ethyl acetate/hexanes (1:10, 1:4, and 1:1, v/v) to give 4-hydroxymethylpiperidine-1-carboxylic acid tert-butyl ester (4.71 g, 97% yield) as a white solid. $^1$H NMR (300 MHz, CDCl$_3$) δ 1.10-1.20 (m, 2H), 1.30 (t, 1H), 1.47 (s, 9H), 1.60-1.69 (m, 1H), 1.69-1.75 (m, 2H), 2.65-2.75 (m, 2H), 3.48-3.52 (m, 2H), 4.05-4.18 (m, 2H). m/z (ESI) 216 [C$_{11}$H$_{21}$NO$_3$+H]$^+$.

4-{2-[4-(4-Aminobutyl)phenoxy]acetoxymethyl}piperidine-1-carboxylic acid tert-butyl ester ethyl acetate (45c)

Following the same procedure for the synthesis of compound 45a, compound 45c was synthesized from compound 44c in 99% yield as an off-white solid, and used directly without purification. m/z (ESI) 421 [C$_{23}$H$_{36}$N$_2$O$_5$+H]$^+$.

4-[2-(4-{4-[N'-(3,5-Diamino-6-chloropyrazine-2-carbonyl)guanidino]butyl}phenoxy)-acetoxymethyl]piperidine-1-carboxylic acid tert-butyl ester (46c)

Following the same procedure for the synthesis of compound 46a, compound 46c was synthesized from compound 45c. One-third of the crude reaction mixture, after concentration under vacuum, was purified by semi-preparative HPLC method (acetonitrile/water) to give 46c as a yellow solid. m/z (ESI) 633 [C$_{29}$H$_{41}$ClN$_8$O$_6$+H]$^+$.

(4-{4-[N'-(3,5-Diamino-6-chloropyrazine-2-carbonyl)guanidino]butyl}phenoxy)acetic acid piperidin-4-yl-methyl ester dihydrochloride (47c, PSA 25720)

Following the same procedure for the synthesis of compound 47a, compound 47c (PSA 25720) was synthesized from compound 46c in 39% yield as a yellow solid. mp 100-102° C.

$^1$H NMR (500 MHz, DMSO-d$_6$) δ 1.30-1.45 (m, 2H), 1.50-1.65 (m, 4H), 1.72-1.80 (m, 2H), 1.88-1.98 (m, 1H), 2.52-2.60 (m, 2H), 2.78-2.88 (m, 2H), 3.20-3.29 (m, 2H), 4.00 (d, 2H), 4.75 (s, 2H), 6.85 (d, 2H), 7.12 (d, 2H), 7.40 (br s, 2H), 8.80 (br s, 3H), 9.20 (br s, 2H). m/z (APCI) 533 [C$_{24}$H$_{33}$ClN$_8$O$_4$$^+$H]$^+$.

Example 20

Sodium Channel Blocking Activity of Selected Soluble Esters

Utilizing the tests set forth above, Table 4 summaries the ENaC blocking ability of some of the Esters of this invention when assayed in canine bronchial epithelium.

TABLE 4

Epithelial Sodium Channel Blocking Activity of Selected Esters

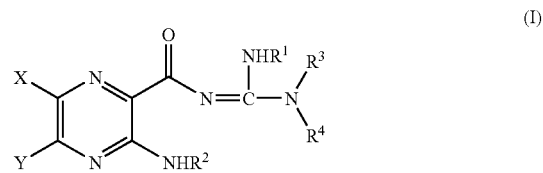

•2 CH$_3$SO$_3$H

| PSA# | IC$_{50}$ (nM) | Fold Amiloride** (PSA4022 = 100) |
|---|---|---|
| 25309 | 4 | 119 |
| 25453 | 19 ± 16 (n = 5) | 38 |
| 25454 | 12 ± 2 (n = 6) | 44 |
| 25720 | 3 ± 0 (n = 4) | 189 |

**Relative potency for PSA4022 = 100 using 1C$_{50}$ from PSA4022 in same run.

Obviously, numerous modifications and variations of the present invention are possible in light of the above teachings. It is therefore to be understood that within the scope of the appended claims, the invention may be practiced otherwise than as specifically described herein.

REFERENCES

1. Rappoport, D. A.; Hassid, Z.; *J. Amer. Chem. Soc.,* 1951, 73, 5524-5525, incorporated herein by reference.

The invention claimed is:
1. A pyrazinoylguanidine compound represented by formula (I):

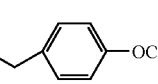

wherein
X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;
Y is hydrogen, hydroxyl, mercapto, lower alkoxy, lower alkyl-thio, halogen, lower alkyl, unsubstituted or substituted mononuclear aryl, or —N(R$^2$)$_2$;
R$^1$ is hydrogen or lower alkyl;
each R$^2$ is, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

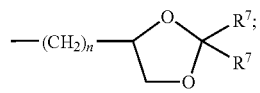

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

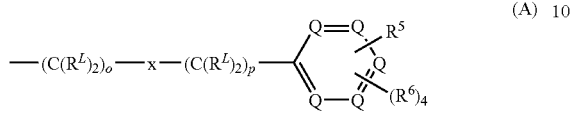

wherein
each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucose,

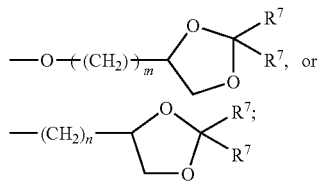

wherein when two $-CH_2OR^8$ groups are located 1,2- or 1,3- with respect to each other the $R^8$ groups may be joined to form a cyclic mono- or di-substituted 1,3-dioxane or 1,3-dioxolane;
each o is, independently, an integer from 0 to 10;
each p is an integer from 0 to 10;
with the proviso that the sum of o and p in each contiguous chain is from 1 to 10;
each x is, independently, O, $NR^{10}$, $C(=O)$, CHOH, $C(=N-R^{10})$, $CHNR^7R^{10}$, or represents a single bond;
each $R^5$ is, independently, $-(CH_2)_n-CO_2R^{13}$, Het-$(CH_2)_m-CO_2R^{13}$, $-(CH_2)_n-Z_g-CO_2R^{13}$, Het-$(CH_2)_m-Z_g-CO_2R^{13}$, $-(CH_2)_n-NR^{10}-(CH_2)_m(CHOR^8)_n-CO_2R^{13}$, Het-$(CH_2)_m-NR^{10}-(CH_2)_m(CHOR^8)_n-CO_2R^{13}$, $-(CH_2)_n-(CHOR^8)_m-CO_2R^{13}$, Het-$(CH_2)_m-(CHOR^8)_m-CO_2R^{13}$, $-(CH_2)_n-(CHOR^8)_mZ_g-CO_2R^{13}$, Het-$(CH_2)_n-(CHOR^8)_m-Z_g-CO_2R^{13}$, $-(CH_2)_n-Z_g-(CH_2)_m-CO_2R^{13}$, $-(CH_2)_n-Z_g(CHOR^8)_m-Z_g-CO_2R^{13}$, HET-$(CH_2)_n-Z_g-(CHOR^8)_m-Z_g-Z_g-CO_2R^{13}$, $-(CH_2)_n-Z_g-(CHOR^8)_m-Z_g-CO_2R^{13}$, $-(CH_2)_n-CONH-C(=NR^{13})-NR^{13}R^{13}$, Het-$(CH_2)_n-CO-NH-C(=NR^{13})-NR^{13}R^{13}$, $-(CH_2)_n-Z_g-CONH-C(=NR^{13})-NR^{13}R^{13}$, Het-$(CH_2)_n-Z_g-CONH-C(=NR^{13})-NR^{13}R^{13}$, $-(CH_2)_n-NR^{10}-(CH_2)_m(CHOR^8)_n-CONH-C(=NR^{13})-NR^{13}R^{13}$, Het-$(CH_2)_n-NR^{10}-(CH_2)_m(CHOR^8)_n-CONH-C(=NR^{13})-NR^{13}R^{13}$, $-(CH_2)_n-(CHOR^8)_m-CONH-C(=NR^{13})-NR^{13}R^{13}$, Het-$(CH_2)_n-(CHOR^8)_m-CONH-C(=NR^{13})-NR^{13}R^{13}$, $-(CH_2)_n-(CHOR^8)_m-Z_g-CONH-C(=NR^{13})-NR^{13}R^{13}$, Het-$(CH_2)_n-(CHOR^8)_m-Z_g-CONH-C(=NR^{13})-NR^{13}R^{13}$, $-(CH_2)_n-Z_g-(CH_2)_m-CONH-C(=NR^{13})-NR^{13}R^{13}$, Het-$(CH_2)_n-Z_g-(CH_2)_m-CONH-C(=NR^{13})-NR^{13}R^{13}$, $-(CH_2)_n-Z_g-(CHOR^8)_m-Z_g-CONH-C(=NR^{13})-NR^{13}R^{13}$, Het-$(CH_2)_n-Z_g-(CHOR^8)_m-Z_g-CONH-C(=NR^{13})-NR^{13}R^{13}$, $-(CH_2)_n-CONR^7-CONR^{13}R^{13}$, Het-$(CH_2)_n-CONR^7-CONR^{13}R^{13}$, $-(CH_2)_n-Z_g-CONR^7-CONR^{13}R^{13}$, $-(CH_2)_n-Z_g-CONR^7-CONR^{13}R^{13}$, $-(CH_2)_n-NR^{10}-(CH_2)_m(CHOR^8)_n-CONR^7-CONR^{13}R^{13}$, Het-$(CH_2)_n-NR^{10}-(CH_2)_m(CHOR^8)_n-CONR^7-CONR^{13}R^{13}$, $-(CH_2)_n-(CHOR^8)_m-CONR^7-CONR^{13}R^{13}$, Het-$(CH_2)_n-(CHOR^8)_m-CONR^{13}-CONR^{13}R^{13}$, $-(CH_2)_n-(CHOR^8)_m-Z_g-CONR^7-CONR^{13}R^{13}$, Het-$(CH_2)_n-(CHOR^8)_m-Z_g-CNR^7-CONR^{13}R^{13}$, $-(CH_2)_n-Z_g-(CH_2)_mCONR^7-CONR^{13}R^{13}$, Het-$(CH_2)_n-Z_g-(CH_2)_mCONR^7-CONR^{13}R^{13}$, $-(CH_2)_n-Z_g(CHOR^8)_m-Z_g-CONR^7-CONR^{13}R^{13}$, Het-$(CH_2)_n-Z_g-(CHOR^8)_m-Z_g-CONR^7-CONR^{13}R^{13}$, $-(CH_2)_n-CONR^7SO_2NR^{13}R^{13}$, Het-$(CH_2)_m-CONR^7SO_2NR^{13}R_{13}$, $-(CH_2)_n-Z_g-CONR^7SO_2NR^{13}R^{13}$, Het-$(CH_2)_m-Z_g-CONR^7SO_2NR^{13}R^{13}$, $-(CH_2)_n-NR^{10}-(CH_2)_m(CHOR^8)_n-CONR^7SO_2NR^{13}R^{13}$, Het-$(CH_2)_m-NR^{10}-(CH_2)_m(CHOR^8)_n-CONR^7SO_2NR^{13}R^{13}$, $-(CH_2)_n-(CHOR^8)_m-CONR^7SO_2NR^{13}R^{13}$, Het-$(CH_2)_m-(CHOR^8)_m-CONR^7SO_2NR^{13}R^{13}$, $(CH_2)_n-(CHOR^8)_m-Z_g-CONR^7SO_2NR^{13}R^{13}$, Het-$(CH_2)_n-(CHOR^8)_m-Z_g-CONR^7SO_2NR^{13}R^{13}$, $-(CH_2)_n-Z_g-(CH_2)_mCONR^7SO_2NR^{13}R^{13}$, Het-$(CH_2)_n-Z_g-(CH_2)_mCONR^7SO_2NR^{13}R^{13}$, $-(CH_2)_n-Z_g-(CHOR^8)_m-Z_g-CONR^7SO_2NR^{13}R^{13}$, Het-$(CH_2)_n-Z_g-(CHOR^8)_n-Z_g-CONR^7SO_2NR^{13}R^{13}$, $-(CH_2)_n-SO_2NR^{13}R^{13}$, Het-$(CH_2)_m-SO_2NR^{13}R^{13}$, $-(CH_2)_n-Z_g-SO_2NR^{13}R^{13}$, Het-$(CH_2)_m-Z_g-SO_2NR^{13}R^{13}$, $-(CH_2)_m-NR^{10}-(CH_2)_m(CHOR^8)_n-SO_2NR^{13}R^{13}$, Het-$(CH_2)_m-NR^{10}-(CH_2)_m(CHOR^8)-SO_2NR^{13}R^{13}$, $-(CH_2)_m-(CHOR^8)_m-SO_2NR^{13}R^{13}$, Het-$(CH_2)_m-(CHOR^8)_m-SO_2NR^{13}R^{13}$, $-(CH_2)_n-(CHOR^8)_m-Z_g-SO_2NR^{13}R^{13}$, Het-$(CH_2)_n-(CHOR^8)_m-Z_g-SO_2NR^{13}R^{13}$, $(CH_2)_n-Z_g-(CH_2)_mSO_2NR^{13}R^{13}$, Het-$(CH_2)_n-Z_g-(CH_2)_mSO_2NR^{13}R^{13}$, $-(CH_2)_n-Z_g-(CHOR^8)_m-Z_g-SO_2NR^{13}R^{13}$, Het-$(CH_2)_n-Z_g-(CHOR^8)_m-Z_g-SO_2NR^{10}-(CH_2)_m-CONR^{13}R^{13}$, Het-$(CH_2)_n-CONR^{13}R^{13}$, $-(CH_2)_n-Z_g-CONR^{13}R^{13}$, Het-$(CH_2)_m-Z^g-CONR^{13}R^{13}$, $-(CH_2)_n-NR^{10}-(CH_2)_m(CHOR^8)_n-CONR^{13}R^{13}$, Het-$(CH_2)_m-NR^{10}-(CH_2)_m(CHOR^8)_n-CONR^{13}R^{13}$, $-(CH_2)_n-(CHOR^8)_m-CONR^{13}R^{13}$, $-(CH_2)_m-(CHOR^8)_m-CONR^{13}R^{13}$, $-(CH_2)_n-(CHOR^8)_m-Z_g-CONR^{13}R^{13}$, Het-$(CH_2)_n-(CHOR^8)_m-Z_g-CONR^{13}R^{13}$, $-(CH_2)_n-Z^g-(CH_2)_mCONR^{13}R^{13}$, Het-$(CH_2)_n-Z^g-(CH_2)_m CONR^{13}R^{13}$, $-(CH_2)_n-Z^g-(CHOR^8)_m-Z^g-CONR^{13}R^{13}$, Het-$(CH_2)_n-(CHOR^8)_m-Z_g-CONR^{13}R^{13}$, $-(CH_2)_n-CONR^7COR^{13}$, Het-$(CH_2)_m-CONR^7COR^{13}$, $-(CH_2)_n-Z_g-CONR^7COR^{13}$, Het-$(CH_2)_m-Z_g-CONR^7COR^{13}$, $-(CH_2)_n-NR^{10}-(CH_2)_m(CHOR^8)_n-CONR^7COR^{13}$, Het-$(CH_2)_m-NR^{10}-(CH_2)_m$ (CHOR⁸)ₙ—CONR⁷COR¹³, —(CH₂)ₙ—(CHOR⁸)ₘ—CONR⁷COR¹³, Het-(CH₂)ₘ—(CHOR⁸)ₘ—CONR⁷COR¹³, —(CH₂)ₙ—(CHOR⁸)ₘ—Z_g—CONR⁷COR¹³, Het-(CH₂)ₙ—(CHOR⁸)ₘ—Z_g—CONR⁷COR¹³, —(CH₂)ₙ—Z_g—(CH₂)ₘCONR⁷COR¹³, —(CH₂)ₙ—Z_g—(CH₂)ₘCONR⁷COR¹³, Het-(CH₂)ₙ—Z_g—(CHOR⁸)ₘ—Z_g—CONR⁷COR¹³, —(CH₂)ₙ—CONR⁷CO₂R¹³, —(CH₂)ₙ—Z_g—CONR⁷CO₂R¹³, Het-(CH₂)ₘ—Z_g—CONR⁷CO₂R¹³, —(CH₂)ₙ—NR¹⁰—(CH₂)ₘ(CHOR⁸)ₙ—CONR⁷CO₂R¹³, Het-(CH₂)ₘ—NR¹⁰—(CH₂)ₘ(CHOR⁸)ₙ—CO NR⁷CO₂R¹³, —(CH₂)ₙ—(CHOR⁸)ₘ—CONR⁷CO₂R¹³, Het-(CH₂)ₘ—(CHOR⁸)ₘ—CONR⁷CO₂R¹³, —(CH₂)ₙ—(CHOR⁸)ₘ—Z_g—CONR⁷CO₂R¹³, Het-(CH₂)ₘ—(CHOR⁸)ₘ—Z_g—CONR⁷CO₂R¹³, —(CH₂)ₙ—Z_g—(CH₂)ₘCONR⁷CO₂R¹³, Het-(CH₂)ₘ—Z_g—(CH₂)ₘCONR⁷CO₂R¹³, —(CH₂)ₙ—Z_g—(CHOR⁸)ₘ—Z_g—CONR⁷CO₂R¹³, Het-(CH₂)ₙ—Z_g—(CHOR⁸)ₘ—Z_g—CONR⁷CO₂R¹³, —(CH₂)ₙ—NH—C(=NR¹³)—NR¹³R¹³, Het-(CH₂)ₘ—NH—C(=NR¹³)—NR¹³R¹³, —(CH₂)ₙ—Z_g—NH—C(=NR¹³)—NR¹³R¹³, Het-(CH₂)ₘ—Z_g—NH—C(=NR¹³)—NR¹³R¹³, —(CH₂)ₙ—NR¹⁰—(CH₂)ₘ(CHOR⁸)ₙ—NH—C(=NR¹³)—NR¹³R¹³, Het-(CH₂)ₘ—NR¹⁰—(CH₂)ₘ(CHOR⁸)ₙ—NH—C(=NR¹³)—NR¹³R¹³, —(CH₂)ₙ—(CHOR⁸)ₘ—NH—C(=NR¹³)—NR¹³R¹³, Het-(CH₂)ₘ—(CHOR⁸)ₘ—NH—C(=NR¹³)—NR¹³R¹³, —(CH₂)ₙ—(CHOR⁸)ₘ—Z_g—NH—C(=NR¹³)—NR¹³R¹³, Het-(CH₂)ₙ—(CHOR⁸)ₘ—Z_g—NH—C(=NR¹³)—NR¹³R¹³, —(CH₂)ₙ—Z_g—(CH₂)ₘNH—C(=NR¹³)—NR¹³R¹³, Het-(CH₂)ₘ—Z_g—(CH₂)ₘ—NH—C(=NR¹³)—NR¹³R¹³, —(CH₂)ₙ—Z_n—(CHOR⁸)ₘ—Z_g—NH—C(=NR¹³)—NR¹³R¹³, Het-(CH₂)ₙ—Z_g—(CHOR⁸)ₘ—Z_g—NH—C(=NR¹³)—NR¹³R¹³, —(CH₂)ₘ—C(=NH)—NR¹³R¹³, Het-(CH₂)ₙ—Z_g—C(=NH)—NR¹³R¹³, —(CH₂)ₘ—Z_g—C(=NH)—NR¹³R¹³, Het-(CH₂)ₘ—Z_g—C(=NH)—NR¹³R¹³, —(CH₂)ₙ—NR¹⁰—(CH₂)ₘ(CHOR⁸)ₙ—C(=NR¹³)—NR¹³R¹³, Het-(CH₂)ₘ—NR¹⁰—(CH₂)ₘ(CHOR⁸)ₙ—C(=NR¹³)—NR¹³R¹³, —(CH₂)ₙ—(CHOR⁸)ₘ—C(=NR¹³)—NR¹³R¹³, Het-(CH₂)ₘ—(CHOR⁸)ₘ—C(=NR¹³)—NR¹³R¹³, —(CH₂)ₙ—(CHOR⁸)ₘ—Z_g—C(=NR¹³)—NR¹³R¹³, Het-(CH₂)ₙ—(CHOR⁸)ₘ—Z_g—C(=NR¹³)—NR¹³R¹³, —(CH₂)ₘ—Z_g—(CH₂)ₘ—C(=NHC(=NR¹³)—NR¹³R¹³, Het-(CH₂)ₙ—Z_g—(CH₂)ₘ—C(=NR¹³)—NR¹³R¹³, —(CH₂)ₙ—Z_g—(CHOR⁸)ₘ—Z_g-C(=NR¹³)—NR¹³R¹³, Het-(CH₂)ₙ—Z_g—(CHOR⁸)ₘ—Z_g—C(=NR¹³)—NR¹³R¹³;

wherein when two —CH₂OR⁸ groups are located 1,2- or 1,3- with respect to each other the R⁸ groups may be joined to form a cyclic mono- or di-substituted 1,3-dioxane or 1,3-dioxolane;

each R⁶ is, independently, —R⁵, —R⁷, —OR⁸, —N(R⁷)₂, —(CH₂)ₘ—OR⁸, —O—(CH₂)ₘ—OR⁸, —(CH₂)ₙ—NR⁷R¹⁰, —O—(CH₂)ₘ—NR⁷R¹⁰, —(CH₂)ₙ(CHOR⁸)(CHOR⁸)ₙ—CH₂OR⁸, —O—(CH₂)ₘ(CHOR⁸)(CHOR⁸)ₙ—CH₂OR⁸, —(CH₂CH₂O)ₘ—R⁸, —O—(CH₂CH₂O)ₘ—R⁸, —(CH₂CH₂O)ₘ—CH₂CH₂NR⁷R¹⁰, —O—(CH₂CH₂O)ₘ—CH₂CH₂NR⁷R¹⁰, —(CH₂)ₙ—C(=O)NR⁷R¹⁰, —O—(CH₂)ₘ—C(=O)NR⁷R¹⁰, —(CH₂)ₙ-(Z)_g—R⁷, —O—(CH₂)ₘ-(Z)_g—R⁷, —(CH₂)ₙ—NR¹⁰—CH₂(CHOR⁸)(CHOR⁸)ₙ—CH₂OR⁸, —O—(CH₂)ₘ—NR¹⁰—CH₂(CHOR⁸)

(CHOR⁸)ₙ—CH₂OR⁸, —(CH₂)ₙ—CO₂R⁷, —O(CH₂)ₘ—CO₂R⁷, —OSO₃H, —O—glucose,

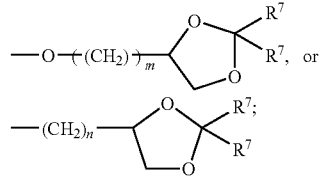

wherein when two R⁶ are —OR¹¹ and are located adjacent to each other on a phenyl ring, the alkyl moieties of the two R⁶ may be bonded together to form a methylenedioxy group, and wherein when two —CH₂OR⁸ groups are located 1,2- or 1,3- with respect to each other the R⁸ groups may be joined to form a cyclic mono- or di-substituted 1,3-dioxane or 1,3-dioxolane;

each R⁷ is, independently, hydrogen lower alkyl, phenyl, or substituted phenyl;

each R⁸ is, independently, hydrogen, lower alkyl, —C(=O)—R¹¹, 2-tetrahydropyranyl,

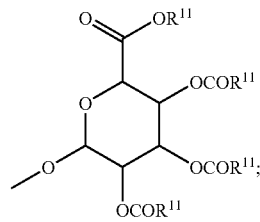

each R⁹ is, independently, —CO₂R⁷, —CON(R⁷)₂, —SO₂CH₃, or —C(=O)R⁷;

each R¹⁰ is, independently, —H, —SO₂CH₃, —CO₂R⁷, —C(=O)NR⁷R⁹, —C(=O)R⁷, or —(CH₂)ₘ—(CHOH)ₙ—CH₂OH;

each Z is, independently, CHOH, C(=O), —(CH₂)ₙ—, CHNR⁷R¹⁰, C=NR¹⁰, or NR¹⁰;

each R¹¹ is, independently, lower alkyl;

each R¹² is independently, —SO₂CH₃, —CO₂R⁷, —C(=O)NR⁷R⁹, —C(=O)R⁷, or CH₂—(CHOH)ₙ—CH₂OH;

each R¹³ is, independently, hydrogen, R⁷, R¹⁰, —(CH₂)ₘ—NR⁷R¹⁰, —(CH₂)ₘ—NR⁷R⁷,

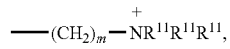

—(CH₂)ₘ—(CHOR⁸)ₘ—(CH₂)ₘNR⁷R¹⁰, —(CH₂)ₘ—NR¹⁰R¹⁰, —(CH₂)ₘ—(CHOR⁸)ₘ—(CH₂)mNR⁷R⁷,

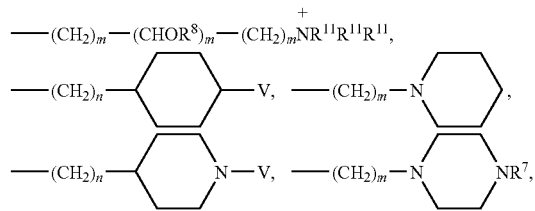

-continued

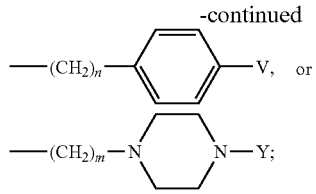

with the proviso that at least one $R^{13}$ must be a group other than hydrogen, $R^7$, or $R^{10}$;
with the additional proviso that $NR^{13}R^{13}$ can be joined on itself to form a ring comprising one of the following:

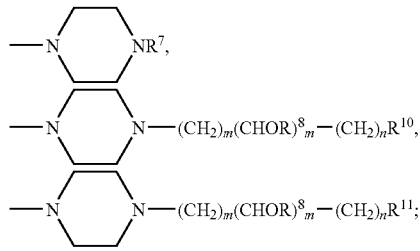

each Het is independently, $-NR^7$, $-NR^{10}$, $-S-$, $-SO-$, $-SO_2-$; $-O-$, $-SO_2NH-$, $-NHSO_2-$, $-NR^7CO-$, or $-CONR^7-$;
each g is, independently, an integer from 1 to 6;
each m is, independently, an integer from 1 to 7;
each n is, independently, an integer from 0 to 7;
each Q is, independently, $C-R^5$, $C-R^6$, or a nitrogen atom, wherein at most three Q in a ring are nitrogen atom;
each V is, independently, $-(CH_2)_m-NR^7R^{10}$, $-(CH_2)_m-NR^7R^7$, $-(CH_2)_m-N^+R^{11}R^{11}R^{11}$, $-(CH_2)_n-(CHOR^8)_m-(CH_2)_mNR^7R^{10}$, $-(CH_2)_n-NR^{10}R^{10}$, $-(CH_2)_n-(CHOR^8)_m-(CH_2)_mNR^7R^7$, or $-(CH_2)_n-(CHOR^8)_m-(CH_2)_mN^+R^{11}R^{11}R^{11}$,
with the proviso that when V is attached directly to a nitrogen atom, then V can also be, independently, $R^7$, $R^{10}$, or $(R^{11})_2$;
wherein when two $-CH_2OR^8$ groups are located 1,2- or 1,3- with respect to each other the $R^8$ groups may be joined to form a cyclic mono- or di-substituted 1,3-dioxane or 1,3-dioxolane;
or a stereoisomer thereof;
or a pharmaceutically acceptable salt thereof.

2. The compound of claim 1 or pharmaceutically acceptable salt thereof, wherein Y is $-NH_2$, $R^2$ is hydrogen, $R^1$ is hydrogen, X is chlorine, $R^3$ is hydrogen and each $R^1$ is hydrogen.

3. The compound of claim 1 or pharmaceutically acceptable salt thereof, wherein o is 4.

4. The compound of claim 1 or pharmaceutically acceptable salt thereof, wherein p is 0.

5. The compound of claim 1 or pharmaceutically acceptable salt thereof, wherein x represents a single bond.

6. The compound of claim 1 or pharmaceutically acceptable salt thereof, wherein each $R^6$ is hydrogen.

7. The compound of claim 1 or pharmaceutically acceptable salt thereof, wherein each $R^5$ is, independently, $-(CH_2)_n-CO_2R^{13}$, Het-$(CH_2)_m-CO_2R^{13}$, $-(CH_2)_n-Z_g-CO_2R^{13}$, Het-$(CH_2)_m-Z_g-CO_2R^{13}$, $-(CH_2)_n-NR^{10}-(CH_2)_m(CHOR^8)_n-CO_2R^{13}$, Het-$(CH_2)_m-NR^{10}-(CH_2)_m(CHOR^8)_n-CO_2R^{13}$, $-(CH_2)_n-(CHOR^8)_m-CO_2R^{13}$, Het -$(CH_2)_m-(CHOR^8)_m-CO_2R^{13}$, $-(CH_2)_n-(CHOR^8)_mZ_g-CO_2R^{13}$, Het-$(CH_2)_n-(CHOR^8)_m-Z_g-CO_2 R^{13}$, $-(CH_2)_n-Z_g-(CH^2)^m-CO_2R^{13}$, $-(CH_2)_n-Z_g-(CH^2)^m-CO_2 R^{13}$, $-(CH_2)_n-Z_g(CHOR^8)_mZ_g-CO_2R^{13}$, or Het-$(CH_2)_n-Z_g-(CHOR^8)_m-Z_g-CO_2 R^{13}$.

8. The compound of claim 1 or pharmaceutically acceptable salt thereof, wherein each $R^5$ is, independently, $-(CH_2)_n-CONH-C(=NR^{13})-NR^{13}R^{13}$, Het-$(CH_2)_n-CO-NH-C(=NR^{13})-NR^{13}R^{13}$, $-(CH_2)_n-Z_g-CONH-C(=NR^{13})-NR^{13}R^{13}$, Het-$(CH_2)_n-Z_g-CONH-C(=NR^{13})-NR^{13}R^{13}$, $-(CH_2)_n-NR^{13}R^{13}$, $-(CH_2)_n-NR^{10}-(CH_2)_m(CHOR^8)_n-CONH-C(=NR^{13})-NR^{13}R^{13}$, Het-$(CH_2)_n-NR^{10}-(CH_2)_m(CHOR^8)_n-CONH-C(=NR^{13})-NR^{13}R^{13}$, $-(CH_2)_n-(CHOR^8)_m-CONH-C(=NR^{13})-NR^{13}R^{13}$, Het-$(CH_2)_n-(CHOR^8)_m-CONH-C(=NR^{13})-NR^{13}R^{13}$, $-(CH_2)_n-(CHOR^8)_m-Z_g-CONH-C(=NR^{13})-NR^{13}R^{13}$, Het-$(CH_2)_n-(CHOR^8)_m-Z_g-(CH_2)_m-CONH-C(=NR^{13})-NR^{13}R^{13}$, $-(CH_2)_n-Z_g-(CHOR^8)_m-Z_g-CONH-C(=NR^{13})-NR^{13}R^{13}$ or Het-$(CH_2)_n-Z_g-(CHOR^8)_m-Z_g-CONH-C(=NR^{13})-NR^{13}R^{13}$.

9. The compound of claim 1 or pharmaceutically acceptable salt thereof, wherein each $R^5$ is, independently, $-(CH_2)_n-CONR^7-CONR^{13}R^{13}$, Het $(CH_2)_n-CONR^7-CONR^{13}R^{13}$, $-(CH_2)_nZ_g-CONR^7-CONR^{13}R^{13}$, $-(CH_2)_n-Z_g-CONR^7-CONR^{13}R^{13}$, $-(CH_2)_n-NR^{10}-(CH_2)_m(CHOR^8)_n-CONR^7-CONR^{13}R^{13}$, Het-$(CH_2)_n-NR^{10}-(CH_2)_m(CHOR^8)_n-CONR^7-CONR^{13}R^{13}$, $-(CH_2)_n-(CHOR^8)_m-CONR^7-CONR^{13}R^{13}$, Het-$(CH_2)_n-(CHOR^8)_m-CONR^7-CONR^{13}R^{13}$, $-(CH_2)_n-(CHOR^8)_m-Z_g-CONR^7-CONR^{13}R^{13}$, Het-$(CH_2)_n-(CHOR^8)_m-Z_g-CNR^7-CONR^{13}R^{13}$, $-(CH_2)_n-Z_g-(CH_2)_mCONR^7-CONR^{13}R^{13}$, Het-(CH2)$_n$-$(CH_2)_mCONR^7-CONR^{13}R^{13}$, $-(CH_2)_n-Z_g(CHOR^8)_m-Z_g-CONR^7-CONR^{13}R^{13}$, or Het-$(CH_2)_n-Z_g(CHOR^8)_m-Z_g-CONR^7-CONR^{13}$.

10. The compound of claim 1 or pharmaceutically acceptable salt thereof, wherein each $R^5$ is, independently, $-(CH_2)_n-CONR^7SO_2NR^{13}R^{13}$, Het -$(CH_2)_m-CONR^7SO_2NR^{13}R^{13}$, $-(CH_2)_n-Z_g-CONR^7SO_2NR^{13}R^{13}$, Het-$(CH_2)_m-Z_g-CONR^7SO_2NR^{13}R^{13}$, $-(CH_2)_n-NR^{10}-(CH_2)_m(CHOR^8)_n-CONR^7SO_2NR^{13}R^{13}$, Het-$(CH_2)_m-NR^{10}-(CH_2)_m(CHOR^8)_n-CONR^7SO_2NR^{13}$, $-(CH_2)_n-(CHOR^8)_m-CONR^7SO_2NR^{13}R^{13}$, Het-$(CH_2)_m-(CHOR^8)_m-CONR^7SO_2NR^{13}R^{13}$, $-(CH_2)_n-(CHOR^8)_m-Z_g-CONR^7SO_2NR^{13}R^{13}$, Het-$(CH_2)_n-(CHOR^8)_m-Z_g-CONR^7SO_2NR^{13}R^{13}$, $-(CH_2)_n-Z_g-(CH_2)_mCONR^7SO_2NR^{13}R^{13}$, Het-$(CH_2)_n-Z_g-(CH_2)_mCONR^7SO_2NR^{13}R^{13}$, $-(CH_2)_n-Z_g-(CHOR^8)_m-Z_g-CONR^7SO_2NR^{13}R^{13}$, or Het-$(CH^2)_n-Z_g-(CHOR^8)_m-Z_g-CONR^7SO_2NR^{13}R^{13}$.

11. The compound of claim 1 or pharmaceutically acceptable salt thereof, wherein each $R^5$ is, independently, $-(CH_2)_n-SO_2NR^{13}R^{13}$, Het-$(CH_2)_m-SO_2NR^{13}R^{13}$, $-(CH_2)_n-Z_g-SO_2NR^{13}R^{13}$, Het-$(CH_2)_m-Z_g-SO_2NR^{13}R^{13}$, $-(CH_2)_n-NR^{10}-(CH_2)_m(CHOR^8)_n-SO_2NR^{13}R^{13}$, Het-$(CH_2)_m-NR^{10}-(CH_2)_m(CHOR^8)_n-SO_2NR^{13}R^{13}$, $-(CH_2)_n-(CHOR^8)_m-SO_2NR^{13}R^{13}$, Het-$(CH^2)_m-(CHOR^8)_m-SO_2NR^{13}R^{13}$, $-(CH_2)_n-(CHOR^8)_m-Z_g-SO_2NR^{13}R^{13}$, Het-$(CH_2)_n-(CHOR^8)_m-Z_g-SO_2NR^{13}R^{13}$, $-(CH_2)_n-Z_g-(CH_2)_mSO_2NR^{13}R^{13}$, Het-$(CH_2)_n-Z_g-(CH_2)_mSO_2NR^{13}R^{13}$, $-(CH_2)_n-Z_g-(CHOR^8)_m-Z_g-SO_2NR^{13}R^{13}$, or Het-$(CH_2)_n-Z_g-(CHOR^8)_m-Z_g-SO_2NR^{13}R^{13}$.

12. The compound of claim 1 or pharmaceutically acceptable salt thereof, wherein each $R^5$ is, independently, $-(CH_2)_n-CONR^{13}R^{13}$, Het-$(CH_2)_m-CONR^{13}R^{13}$, $-(CH_2)_n-Z_g-CONR^{13}R^{13}$, Het-$(CH_2)_m-Z_g-CONR^{13}R^{13}$, $-(CH_2)_n-NR^{10}-(CH_2)_m(CHOR^8)_n-CONR^{13}R^{13}$, Het-$(CH_2)_m-NR^{10}-(CH_2)_m(CHOR^8)_n-CONR^{13}R^{13}$, $-(CH_2)_n-(CHOR^8)_m-CONR^{13}R^{13}$, Het-$(CH_2)_m-(CHOR^8)_m-CONR^{13}R^{13}$, $-(CH_2)_n-(CHOR^8)_m-Z_g-CONR^{13}R^{13}$, Het-$(CH_2)_n(CHOR^8)_m-Z_g-CONR^{13}R^{13}$, $-(CH_2)_n-Z_g-(CH_2)_mCONR^{13}R^{13}$, Het-$(CH_2)_n-Z_g-(CH_2)_mCONR^{13}R^{13}$, $-(CH_2)_n-Z_g-(CHOR^8)_m-Z_g-CONR^{13}R^{13}$, or Het-$(CH_2)_n-Z_g-(CHOR^8)_m-Z_g-CONR^{13}R^{13}$.

13. The compound of claim 1 or pharmaceutically acceptable salt thereof, wherein each $R^5$ is, independently, $-(CH_2)_n-CONR^7COR^{13}$, Het-$(CH_2)_m-CONR^7COR^{13}$, $-(CH_2)_n-Z_g-CONR^7COR^{13}$, Het-$(CH_2)_m-Z_g-CONR^7COR^{13}$, $-(CH_2)_n-NR^{10}-(CH_2)_m(CHOR^8)_n-CONR^7COR^{13}$, Het-$(CH_2)_m-NR^{10}-(CH_2)_m(CHOR^8)_n-CONR^7COR^{13}$, $-(CH_2)_n-(CHOR^8)_m-CONR^7COR^{13}$, Het-$(CH_2)_m-(CHOR^8)_m-CONR^7COR^{13}$, $-(CH_2)_n-(CHOR^8)_m-Z_g-CONR^7COR^{13}$, Het-$(CH_2)_m-(CHOR^8)_m-Z_g-CONR^7COR^{13}$, $-(CH_2)_n-Z_g-(CH_2)_mCONR^7COR^{13}$, $-(CH_2)_n-Z_g-(CH_2)_mCONR^7COR^{13}$, or Het-$(CH_2)_n-Z_g-(CHOR^8)_m-Z_g-CONR^7COR^{13}$.

14. The compound of claim 1 or pharmaceutically acceptable salt thereof, wherein each $R^5$ is, independently, $-(CH_2)_n-CONR^7CO_2R^{13}$, $-(CH_2)_n-Z_g-CONR^7CO_2R^{13}$, Het-$(CH_2)_m-Z_g-CONR^7CO_2R^{13}$, $-(CH_2)_n-NR^{10}-(CH_2)_m(CHOR^8)_n-CONR^7CO_2R^{13}$, Het-$(CH_2)_m-NR^{10}(CH_2)_m(CHOR^8)_n-CO\ NR^7CO_2R^{13}$, $-(CH_2)_n-(CHOR^8)_m-CONR^7CO_2R^{13}$, Het-$(CH_2)_m-(CHOR^8)_m-CONR^7CO_2R^{13}$, $-(CH_2)_n-(CHOR^8)_m-Z_g-CONR^7CO_2R^{13}$, Het-$(CH_2)_n-(CHOR^8)_m-Z_g-CONR^7CO_2R^{13}$, $-(CH_2)_n-Z_g-(CH_2)_mCONR^7CO_2R^{13}$, Het-$(CH_2)_n-Z_g-(CH_2)_mCONR^7CO_2R^{13}$, $-(CH^2)_n-Z_g-(CHOR^8)_m-Z_g-CONR^7CO_2R^{13}$, or Het-$(CH_2)_n-Z_g-(CHOR^8)_m-Z_g-CONR^7CO_2R^{13}$.

15. The compound of claim 1 or pharmaceutically acceptable salt thereof, wherein each $R^5$ is, independently, $-(CH_2)_n-NH-C(=NR^{13})-NR^{13}R^{13}$, Het-$(CH_2)_m-NH-C(=NR^{13})-NR^{13}R^{13}$, $-(CH_2)_n-Z_g-NH-C(=NR^{13})-NR^{13}R^{13}$, Het-$(CH_2)_m-Z_g-NH-C(=NR^{13})-NR^{13}R^{13}$, $-(CH_2)_n-NR^{10}-(CH_2)_m(CHOR^8)_n-NH-C(=NR^{13})-NR^{13}R^{13}$, Het-$(CH_2)_m-NR^{10}-(CH_2)_m(CHOR^8)_n-NH-C(=NR^{13})-NR^{13}R^{13}$, $-(CH_2)_n-(CHOR^8)_m-NH-C(=NR^{13})-NR^{13}R^{13}$, Het-$(CH_2)_m-(CHOR^8)_m-NH-C(=NR^{13})-NR^{13}R^{13}$, $-(CH_2)_n-(CHOR^8)_m-Z_g-NH-C(=NR^{13})-NR^{13}R^{13}$, Het-$(CH_2)_n-(CHOR^8)_m-Z_g-NH-C(=NR^{13})-NR^{13}R^{13}$, $-(CH_2)_n-Z_g-(CH_2)_mNH-C(=NR^{13})-NR^{13}R^{13}$, Het-$(CH_2)_n-Z_g-(CH^2)_mNH-C(=NR^{13})-NR^{13}R^{13}$, $-(CH_2)_n-Z_g-(CHOR^8)_m-Z_g-NH-C(=NR^{13})-NR^{13}R^{13}$, Het-$(CH_2)_n-Z_g-(CHOR^8)_m-Z_g-NH-C(=NR_{13})-NR^{13}R^{13}$, $-(CH_2)_n-C(=NR^{13})-NR^{13}R^{13}$, Het-$(CH_2)_m-C(=NH)-NR^{13}R^{13}$, $-(CH_2)_n-Z_g-C(=NH)-NR^{13}R^{13}$, Het-$(CH_2)_m-Z_g-C(=NH)-NR^{13}R^{13}$, or $-(CH_2)_n-NR^{10}-(CH_2)_m(CHOR^8)_n-C(=NR^{13})-NR^{13}R^{13}$.

16. The compound of claim 1 or pharmaceutically acceptable salt thereof, wherein each $R^5$ is, independently, $-(CH_2)_n-C(=NR^{13})-NR^{13}R^{13}$, Het-$(CH_2)_m-C(=NH)-NR^{13}R^{13}$, $-(CH_2)_n-Z_g-C(=NH)-NR^{13}R^{13}$, Het-$(CH_2)_m-Z_g-C(=NH)-NR^{13}R^{13}$, $-(CH_2)_n-NR^{10}-(CH_2)_m(CHOR^8)_n-C(=NR^{13})-NR^{13}R^{13}$, Het-$(CH_2)_m-NR^{10}-(CH_2)_m(CHOR^8)_n-C(=NR^{13})-NR^{13}R^{13}$, $-(CH_2)_n-(CHOR^8)_m-C(=NR^{13})-NR^{13}R^{13}$, Het-$(CH_2)_m-(CHOR^8)_m-C(=NR^{13})-NR^{13}R^{13}$, $-(CH_2)_n-(CHOR^8)_m-Z_g-C(=NR^{13})-NR^{13}R^{13}$, Het-$(CH_2)_n-(CHOR^8)_m-Z_g-C(=NR^{13})-NR^{13}R^{13}$, $-(CH_2)_n-Z_g-(CH_2)_m-C(=NR^{13})-NR^{13}R^{13}$, Het-$(CH_2)_n-Z_g-(CH_2)_m-C(=N\ R^{13})-NR^{13}R^{13}$, $-(CH_2)_n-Z_g-(CHOR^8)_m-Z_g-C(=NR^{13})-NR^{13}R^{13}$, or Het-$(CH_2)_n-Z_g-(CHOR^8)_m-Z_g-C(=NR^{13})-NR^{13}R^{13}$.

17. The compound of claim 1, which is in the form of a pharmaceutically acceptable salt.

18. A pharmaceutical composition, comprising the compound of claim 1 or pharmaceutically acceptable salt thereof and a pharmaceutically acceptable carrier.

* * * * *